(12) United States Patent
Fischer et al.

(10) Patent No.: US 8,575,150 B2
(45) Date of Patent: Nov. 5, 2013

(54) TRIAZOLE DERIVATIVES FOR TREATMENT OF ALZHEIMER'S DISEASE

(75) Inventors: Christian Fischer, Natick, MA (US); Joey Methot, Westwood, MA (US); Hua Zhou, Acton, MA (US); Adam J. Schell, Newton, MA (US); Benito Munoz, Cambridge, MA (US); Alexey A. Rivkin, Boston, MA (US); Sean P. Ahearn, Somerville, MA (US); Stephanie Chichetti, Brooklyn, NY (US); Rachel N. MacCoss, Brookline, MA (US); Sam Kattar, Arlington, MA (US); Matthew Christopher, Brookline, MA (US); Chaomin Li, Boston, MA (US); Andrew Rosenau, Cambridge, MA (US); William Colby Brown, Cleveland Heights, OH (US)

(73) Assignee: Merck Sharp & Dohme Corp., Rahway, NJ (US)

( * ) Notice: Subject to any disclaimer, the term of this patent is extended or adjusted under 35 U.S.C. 154(b) by 68 days.

(21) Appl. No.: 13/139,830

(22) PCT Filed: Dec. 7, 2009

(86) PCT No.: PCT/US2009/066914
§ 371 (c)(1),
(2), (4) Date: Oct. 13, 2011

(87) PCT Pub. No.: WO2010/071741
PCT Pub. Date: Jun. 24, 2010

(65) Prior Publication Data
US 2012/0022044 A1    Jan. 26, 2012

Related U.S. Application Data

(60) Provisional application No. 61/122,948, filed on Dec. 16, 2008.

(51) Int. Cl.
*C07D 249/14*    (2006.01)
*A61K 31/4196*    (2006.01)

(52) U.S. Cl.
USPC .................................. 514/212.07; 540/523

(58) Field of Classification Search
USPC .................................. 540/523; 514/212.07
See application file for complete search history.

(56) References Cited

U.S. PATENT DOCUMENTS 8,242,150 B2 *    8/2012    Fischer et al. .............. 514/359
2007/0117798 A1    5/2007    Kimura et al.

FOREIGN PATENT DOCUMENTS

WO    WO 2004/110350    12/2004
WO    WO 2010/071741    6/2010

OTHER PUBLICATIONS

PCT International Search Report dated Dec. 23, 2004, mailed on Feb. 5, 2010 for related International Application No. PCT/US2009/066906.
PCT International Search Report dated Jan. 17, 2010, mailed on Jan. 27, 2010 for related International Application No. PCT/US2009/066914.

* cited by examiner

*Primary Examiner* — Bruck Kifle
(74) *Attorney, Agent, or Firm* — Susan L. Hess; John C. Todaro

(57) ABSTRACT

According to the invention there is provided a compound of formula I or a pharmaceutically acceptable salt or hydrate thereof; wherein the variables are as defined herein. The compounds selectively attenuate the production of Aβ42 and hence are useful in treatment of Alzheimer's disease and related conditions.

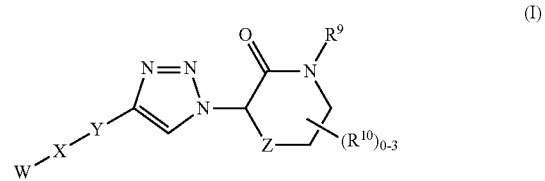

8 Claims, No Drawings

TRIAZOLE DERIVATIVES FOR TREATMENT OF ALZHEIMER'S DISEASE

CROSS REFERENCE TO RELATED APPLICATIONS

This application is the national stage application under 35 U.S.C. 371 of International Patent Application No. PCT/US2009/066914, filed in the U.S. Receiving Office on Dec. 7, 2009, which claims the benefit of U.S. Provisional Application No. 61/122,948, filed Dec. 16, 2008. Each of the aforementioned PCT and Provisional applications is incorporated by reference in its entirety as if fully set forth herein.

This invention relates to compounds for use in therapeutic treatment of the human body. In particular, it provides triazole derivatives useful for treating diseases associated with the deposition of β-amyloid peptide in the brain, such as Alzheimer's disease, or of preventing or delaying the onset of dementia associated with such diseases.

Alzheimer's disease (AD) is the most prevalent form of dementia. Its diagnosis is described in the Diagnostic and Statistical Manual of Mental Disorders, 4$^{th}$ ed., published by the American Psychiatric Association (DSM-IV). It is a neurodegenerative disorder, clinically characterized by progressive loss of memory and general cognitive function, and pathologically characterized by the deposition of extracellular proteinaceous plaques in the cortical and associative brain regions of sufferers. These plaques mainly comprise fibrillar aggregates of β-amyloid peptide (Aβ). Aβ is formed from amyloid precursor protein (APP) via separate intracellular proteolytic events involving the enzymes β-secretase and γ-secretase. Variability in the site of the proteolysis mediated by γ-secretase results in Aβ of varying chain length, e.g. Aβ(1-38), Aβ(1-40) and Aβ(1-42). N-terminal truncations such as Aβ(4-42) are also found in the brain, possibly as a result of variability in the site of proteolysis mediated by β-secretase. For the sake of convenience, expressions such as "Aβ(1-40)" and "Aβ(1-42)" as used herein are inclusive of such N-terminal truncated variants. After secretion into the extracellular medium, Aβ forms initially-soluble aggregates which are widely believed to be the key neurotoxic agents in AD (see Gong et al, *PNAS,* 100 (2003), 10417-22), and which ultimately result in the insoluble deposits and dense neuritic plaques which are the pathological characteristics of AD.

Other dementing conditions associated with deposition of Aβ in the brain include cerebral amyloid angiopathy, hereditary cerebral haemorrhage with amyloidosis, Dutch-type (HCHWA-D), multi-infarct dementia, dementia pugilistica and Down syndrome.

Various interventions in the plaque-forming process have been proposed as therapeutic treatments for Aβ (see, for example, Hardy and Selkoe, *Science,* 297 (2002), 353-6). One such method of treatment that has been proposed is that of blocking or attenuating the production of Aβ for example by inhibition of β- or γ-secretase. It has also been reported that inhibition of glycogen synthase kinase-3 (GSK-3), in particular inhibition of GSK-3α, can block the production of Aβ (see Thiel et al, *Nature,* 423 (2003), 435-9). Other proposed methods of treatment include administering a compound which blocks the aggregation of Aβ, and administering an antibody which selectively binds to Aβ.

However, recent reports (Pearson and Peers, *J. Physiol.,* 575.1 (2006), 5-10) suggest that Aβ may exert important physiological effects independent of its role in AD, implying that blocking its production may lead to undesirable side effects. Furthermore, γ-secretase is known to act on several different substrates apart from APP (e.g. notch), and so inhibition thereof may also lead to unwanted side effects. There is therefore an interest in methods of treating AD that do not suppress completely the production of Aβ, and do not inhibit the action of γ-secretase.

One such proposed treatment involves modulation of the action of γ-secretase so as to selectively attenuate the production of Aβ(1-42). This results in preferential secretion of the shorter chain isoforms of Aβ, which are believed to have a reduced propensity for self-aggregation and plaque formation, and hence are more easily cleared from the brain, and/or are less neurotoxic. Compounds showing this effect include certain non-steroidal antiinflammatory drugs (NSAIDs) and their analogues (see WO 01/78721 and US 2002/0128319 and Weggen et al *Nature,* 414 (2001) 212-16; Morihara et al, *J. Neurochem.,* 83 (2002), 1009-12; and Takahashi et al, *J. Biol. Chem.,* 278 (2003), 18644-70). Compounds which modulate the activity of PPARα and/or PPARδ are also reported to have the effect of lowering Aβ(1-42) (WO 02/100836). NSAID derivatives capable of releasing nitric oxide have been reported to show improved anti-neuroinflammatory effects and/or to reduce intracerebral Aβ deposition in animal models (WO 02/092072; Jantzen et al, *J Neuroscience,* 22 (2002), 226-54). US 2002/0015941 teaches that agents which potentiate capacitative calcium entry activity can lower Aβ(1-42).

Further classes of compounds capable of selectively attenuating Aβ(1-42) production are disclosed in WO 2005/054193, WO 2005/013985, WO 2006/008558, WO 2005/108362, WO 2006/043064. WO 2007/054739, WO 2007/110667, WO 2007/116228, WO 2007/125364, WO 2008/097538, WO 2008/099210 and WO 2008/100412.

US 2006/0004013 and WO 2006/046575 disclose cinnamide derivatives which inhibit production of Aβ. The compounds are said to reduce the production of both Aβ(1-40) and Aβ(1-42). Related cinnamide derivatives are disclosed in US 2007/0117798, US 2007/0219181, WO 2007/135969 and WO 2007/135970.

Further compounds which are claimed to modulate Aβ levels are disclosed in WO 2004/110350.

The compounds of the present invention selectively attenuate production of Aβ(1-42).

According to the invention there is provided a compound of formula I:

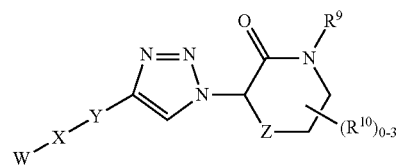

or a pharmaceutically acceptable salt or hydrate thereof; wherein:

W represents phenyl or 5- or 6-membered heteroaryl, any of which is optionally fused to a further 5- or 6-membered carbocyclic or heterocyclic ring, W optionally bearing up to 3 R$^1$ substituents; or when X is a bond W may represent CN and when X is CO, W may represent a piperazin-1-yl or piperidin-1-yl ring;

each R$^1$ independently represents halogen, OH, amino, CF$_3$, C$_{1-4}$alkylamino, di(C$_{1-4}$alkyl)amino, C$_{2-6}$acylamino, N—C$_{1-4}$alkoxycarbamoyl, C$_{1-6}$alkoxy, C$_{1-6}$alkylcarbonyl, or C$_{1-6}$alkyl which is optionally substituted with OH or C$_{1-4}$alkoxy;

X represents a bond, $(CH_2)_nO$, $(CH_2)_nNH$, CO or $(CH_2)_n$NHCO where each n is 0 or 1;

Y represents a phenyl or 5- or 6-membered heteroaryl ring which optionally bears up to 3 $R^2$ substituents; or when X is a bond and W is not CN, Y may represent C≡C or a $C_{3-6}$cycloalkyl ring; or when X is a bond or CO, Y may represent piperidin-4-yl;

or the moiety W-X-Y may represent a fused-ring system consisting of 2 or 3 fused rings each of which is independently 5- or 6-membered and at least one of which is aromatic, said fused-ring system optionally bearing up to 3 $R^2$ substituents;

with the proviso that if X is a bond and W represents an imidazole, triazole or pyrazole ring which is linked to Y through N, then Y does not represent

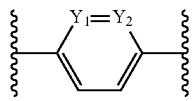

where Y1 and Y2 each independently represents N or $CR^2$;

each $R^2$ independently represents halogen, CN, OH, $C_{1-6}$alkyl, or $C_{1-6}$alkoxy, said alkyl and alkoxy optionally having up to 3 fluorine substituents or a cyclopropyl substituent;

Z represents $CH_2$, $CH_2$—$CH_2$, O, S, NH, $CH_2$—O, $CH_2$—S or $CH_2$—NH;

$R^9$ represent H, $C_{1-6}$alkyl, $C_{2-6}$alkenyl, polyfluoro$C_{1-4}$alkyl, $C_{3-6}$cycloalkyl, $C_{3-6}$cycloalkyl$C_{1-4}$alkyl, $C_{1-4}$alkoxy$C_{1-4}$alkyl, amino$C_{1-4}$alkyl, $C_{1-4}$alkylcarbonyl, polyfluoro$C_{1-4}$alkylcarbonyl, $C_{1-4}$alkylsulfonyl, phenyl, phenylsulfonyl, benzoyl, benzyl, naphthylmethyl or pyridylmethyl, where said phenyl and the aromatic portions of said phenylsulfonyl, benzoyl, benzyl, naphthylmethyl and pyridylmethyl optionally bear up to 3 substituents selected from halogen, $C_{1-4}$alkyl, $C_{1-4}$alkoxy and $CF_3$;

each $R^{10}$ independently represents halogen, OH, $C_{1-4}$alkyl, $C_{2-4}$alkenyl, polyfluoro$C_{1-4}$alkyl, $C_{3-6}$cycloalkyl, $C_{3-6}$cycloalkyl$C_{1-4}$alkyl, $C_{1-4}$alkoxy, $C_{1-4}$alkoxy$C_{1-4}$alkyl, polyfluoro$C_{1-4}$alkoxy, $C_{1-4}$alkylcarbonyl, polyfluoro$C_{1-4}$alkylcarbonyl, $C_{1-4}$alkoxycarbonyl, $C_{1-4}$alkylthio, $C_{1-4}$alkylsulfonyl, $SO_2NR_2$, $CONR_2$ or $NR_2$ where each R is independently H or $C_{1-4}$alkyl or the two R groups together with the nitrogen to which they are attached complete a ring selected from azetidine, pyrrolidine, piperidine, piperazine and morpholine; or phenyl or benzyl either of which optionally is substituted with halogen, $C_{1-4}$alkyl, $C_{1-4}$alkoxy or $CF_3$;

or two $R^{10}$ groups attached to adjacent ring positions optionally complete a fused benzene, naphthalene, cyclopentane, cyclohexane, pyridine, thiophene or furan ring which optionally bears up to 2 substituents independently selected from halogen, $NO_2$, CN, OH, phenyl, $C_{1-4}$alkyl, $C_{2-4}$alkenyl, polyfluoro$C_{1-4}$alkyl, $C_{3-4}$cycloalkyl, $C_{3-6}$cycloalkyl$C_{1-4}$alkyl, $C_{1-4}$alkoxy, $C_{1-4}$alkoxy$C_{1-4}$alkyl, polyfluoro$C_{1-4}$alkoxy, $C_{1-4}$alkylcarbonyl, polyfluoro$C_{1-4}$alkylcarbonyl, $C_{1-4}$alkoxycarbonyl, $C_{1-4}$alkylthio, $C_{1-4}$alkylsulfonyl, $SO_2NR_2$, $CONR_2$ or $NR_2$ where each R is independently H or $C_{1-4}$alkyl;

or two $R^{10}$ groups attached to non-adjacent ring positions optionally complete a $CH_2$ or $CH_2CH_2$ bridge.

Where a variable occurs more than once in formula I, the identity taken by said variable at any particular occurrence is independent of the identity taken at any other occurrence.

As used herein, the expression "$C_{1-4}$alkyl" where x is an integer greater than 1 refers to straight-chained and branched alkyl groups wherein the number of constituent carbon atoms is in the range 1 to x. Particular alkyl groups are methyl, ethyl, n-propyl, isopropyl and t-butyl. Derived expressions such as "$C_{2-6}$alkenyl", "hydroxy$C_{1-6}$alkyl", "heteroaryl$C_{1-6}$alkyl", "$C_{2-6}$alkynyl" and "$C_{1-6}$alkoxy" are to be construed in an analogous manner.

The expressions "polyfluoroalkyl" and "polyfluoroalkoxy" refer to alkyl and alkoxy groups respectively in which one or more of the hydrogen atoms is replaced by fluorine, and includes embodiments of such groups in which all the hydrogens are replaced by fluorine. Examples thus include $CH_2F$, $CHF_2$, $CF_3$, $CF_2CF_3$, $CH_2CF_3$ and $OCF_3$.

The expression "$C_{3-4}$cycloalkyl" where x is an integer greater than 3 refers to saturated cyclic hydrocarbon groups containing from 3 to x ring carbons. Where the value of x so permits, polycyclic systems containing fused rings and/or bridged bicyclic structures are included. Examples include cyclopropyl, cyclobutyl, cyclopentyl, cyclohexyl, decahydronaphthyl, bicyclo[2.2.2]octyl and adamantyl. "$C_{3-4}$cycloalkenyl" similarly refers to nonaromatic unsaturated cyclic hydrocarbon groups, such as cyclopentenyl and cyclohexenyl.

The term "heterocyclic" refers to ring systems in which at least one ring atom is selected from N, O and S, the remaining ring atoms being carbon. Unless indicated otherwise, the term includes both saturated and unsaturated systems, including aromatic systems. Heterocyclic groups may be bonded via a ring carbon or a ring nitrogen, unless otherwise indicated. "Heteroaryl" refers to a heterocyclic ring that is aromatic.

The term "halogen" as used herein includes fluorine, chlorine, bromine and iodine, of which fluorine and chlorine, and in particular fluorine, are preferred unless otherwise indicated.

For use in medicine, the compounds of formula I may be in the form of pharmaceutically acceptable salts. Other salts may, however, be useful in the preparation of the compounds of formula I or of their pharmaceutically acceptable salts. Suitable pharmaceutically acceptable salts of the compounds of this invention include acid addition salts which may, for example, be formed by mixing a solution of the compound according to the invention with a solution of a pharmaceutically acceptable acid such as hydrochloric acid, sulfuric acid, methanesulfonic acid, benzenesulfonic acid, fumaric acid, maleic acid, succinic acid, acetic acid, benzoic acid, oxalic acid, citric acid, tartaric acid, carbonic acid or phosphoric acid. Alternatively, a pharmaceutically acceptable salt may be formed by neutralisation of a carboxylic acid group with a suitable base. Examples of pharmaceutically acceptable salts thus formed include alkali metal salts such as sodium or potassium salts; ammonium salts; alkaline earth metal salts such as calcium or magnesium salts; and salts formed with suitable organic bases, such as amine salts (including pyridinium salts) and quaternary ammonium salts.

It is to be understood that all the stereoisomeric forms encompassed by formula I, both optical and geometrical, fall within the scope of the invention, singly or as mixtures in any proportion.

Where a structure in accordance with formula I is capable of existing in tautomeric keto and enol forms, both of said forms fall within the scope of the invention, singly or as mixtures in any proportion.

In formula I, X is a linking group selected from a bond, $(CH_2)_nO$, $(CH_2)_nNH$, CO and $(CH_2)_nNHCO$ where each n is 0 or 1; or X together with W and Y forms a fused ring system as described hereinafter. For the avoidance of doubt, when X represents $CH_2O$, $CH_2NH$ or $CH_2NHCO$, W is attached to the $CH_2$ group. In a particular embodiment X represents a bond, O or NH, and more particularly X is a bond.

In one embodiment W represents phenyl or 5- or 6-membered heteroaryl, any of which is optionally fused to a further 5- or 6-membered carbocyclic or heterocyclic ring, and optionally bears up to 3 $R^1$ substituents. When W represents a heteroaryl ring, said ring typically comprises up to 3 heteroatoms selected from N, O and S. When W comprises an additional fused ring, said fused ring typically contains 0, 1 or 2 heteroatoms selected from N, O and S. In one sub-embodiment, W represents phenyl or a fused derivative thereof such as naphthalene, tetrahydronaphthalene, quinoline or methylenedioxyphenyl. In an alternative sub-embodiment W represents 6-membered heteroaryl such as pyridine, pyridazine or pyrimidine, or a fused derivative thereof such as quinoline. In a further sub-embodiment W represents 5-membered heteroaryl such as pyrrole, furan, thiophene, pyrazole, imidazole, oxazole, isoxazole, thiazole, isothiazole, triazole, oxadiazole or thiadiazole, or (where such fusion is feasible) the benzo- or pyrido-fused analogues thereof. In all of the aforementioned sub-embodiments, W optionally bears up to 3 (preferably up to 2) $R^1$ substituents where each $R^1$ independently represents halogen (e.g. F or Cl), OH, amino, $CF_3$, $C_{1-4}$alkylamino (e.g. methylamino), di($C_{1-4}$alkyl)amino (e.g. dimethylamino), $C_{2-6}$acylamino (e.g. acetylamino), N—$C_{1-4}$alkoxycarbamoyl (e.g. N-methoxycarbamoyl), $C_{1-6}$alkoxy (e.g. methoxy or ethoxy), $C_{1-6}$alkylcarbonyl (e.g. acetyl), or $C_{1-6}$alkyl which is optionally substituted with OH or $C_{1-4}$alkoxy (e.g. methyl, ethyl, isopropyl or hydroxymethyl). If two or more substituents are present, preferably not more than one of them is other than halogen, methoxy or $C_{1-6}$alkyl.

Specific identities for W include pyrid-4-yl, 3-methylpyrid-4-yl, 3-ethylpyrid-4-yl, 3-isopropylpyrid-4-yl, 3-(trifluoromethyl)pyrid-4-yl, 3-(hydroxymethyl)pyrid-4-yl, 3-methoxypyrid-4-yl, 3-fluoropyrid-4-yl, 3-chloropyrid-4-yl, 2-fluoropyrid-4-yl, 2-methoxypyrid-4-yl, 3,5-difluoropyrid-4-yl, 3,5-dimethylpyrid-4-yl, pyrid-3-yl, 4-methylpyrid-3-yl, 2-methylpyrid-3-yl, 4-acetylaminopyrid-3-yl, pyrimidin-4-yl, pyrimidin-5-yl, 2-methoxypyrimidin-5-yl, pyridazin-5-yl, phenyl, 3-methoxyphenyl, 3-acetylaminophenyl, 3-aminophenyl, 3-methyl-4-methoxyphenyl, 4-hydroxyphenyl, 4-methoxyphenyl, 4-ethoxyphenyl, 4-ethylphenyl, 3,4-dimethoxyphenyl, 2,4-dimethoxyphenyl, 3,4-methylenedioxyphenyl, quinolin-6-yl, oxazol-5-yl, isoxazol-4-yl, 5-methyl-1,3,4-oxadiazol-2-yl, 5-methyl-1,2,4-oxadiazol-3-yl, 3-methyl-1,2,4-oxadiazol-5-yl, thiazol-2-yl, 2,4-dimethylthiazol-5-yl, 1H-indol-5-yl, benzfuran-5-yl, 2,3-dihydrobenzofuran-5-yl, 5-acetylthiophen-2-yl, 1H-pyrazol-3-yl and 2-methyl-1H-pyrazol-4-yl.

In an alternative embodiment, when X represents a bond W may represent CN, and when X represents CO, W may represent a piperidin-1-yl or piperazin-1-yl ring, e.g. 4-methylpiperazin-1-yl.

In one embodiment Y represents a phenyl or 5- or 6-membered heteroaryl ring which optionally bears up to 3 (preferably up to 2) $R^2$ substituents. Suitable 6-membered heteroaryl rings include pyridine and pyrimidine, and suitable 5-membered heteroaryl rings include thiophene, furan, thiazole and imidazole. In the case of phenyl and 6-membered heteroaryl rings, the attachment points typically are in the 1, 3 or 1,4 configuration (in particular 1,4), and in the case of 5-membered heteroaryl rings, the attachment points preferably are in the 1,3 configuration. Each $R^2$ independently represents halogen, CN, OH, $C_{1-6}$alkyl or $C_{1-6}$alkoxy, said alkyl and alkoxy optionally having up to 3 fluorine substituents or a cyclopropyl substituent. Suitable identities for $R^2$ include F, Cl, CN, methyl, methoxy, 2,2,2-trifluoroethoxy and cyclopropylmethoxy, in particular F, Cl, methyl and methoxy. Very suitably, Y is a phenyl ring bearing a methoxy substituent ortho to the attachment point of W-X.

In an alternative embodiment, when X is a bond and W is not CN, Y may represent or a $C_{3-6}$cycloalkyl ring (in particular cyclopropyl); or when X is a bond or CO, Y may represent piperidin-4-yl.

In a particular embodiment, W represents 4-pyridyl which optionally bears up to 2 substituents selected from F, Cl, $CF_3$, $C_{1-4}$alkyl, and $C_{1-4}$alkoxy, X is a bond, and Y represents 1,4-phenylene which optionally bears up to 2 substituents selected from F, Cl, $CF_3$, $C_{1-4}$alkyl, and $C_{1-4}$alkoxy.

In an alternative embodiment the moiety W-X-Y represents a fused-ring system consisting of 2 or 3 fused rings each of which is independently 5- or 6-membered and at least one of which is aromatic, said fused-ring system optionally bearing up to 3 (preferably up to 2) $R^2$ substituents. Suitable fused ring systems include quinoline, benzopyrazole, 1H-pyrrolo[2,3-c]pyridine, 4H-imidazo[2,1-c]-1,4-benzoxazine and [1]benzofuro[3,2-c]pyridine. Specific examples of groups represented by W-X-Y within this embodiment include:

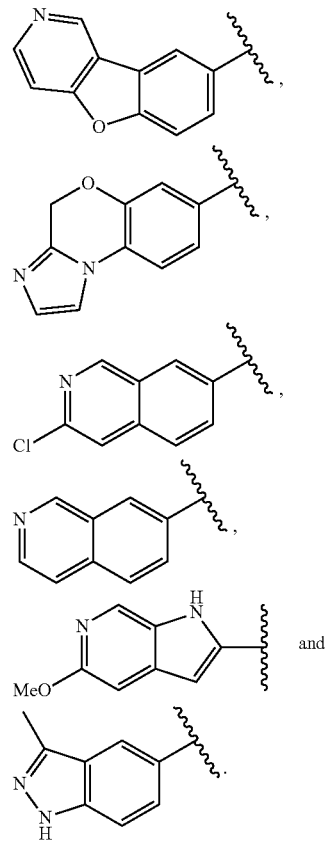

In formula I Z represents $CH_2$, $CH_2$—$CH_2$, O, S, NH, $CH_2$—O, $CH_2$—S or $CH_2$—NH. In a particular embodiment Z represents $CH_2$—$CH_2$.

Preferred identities for $R^9$ include H, $C_{1-4}$alkyl (including methyl, ethyl, isopropyl, t-butyl and 2,2-dimethylpropyl), polyfluoro$C_{1-4}$alkyl (including 2-fluoroethyl, 2,2-difluoroethyl and 2,2,2-trifluoroethyl), $C_{3-6}$cycloalkyl (including cyclohexyl and cyclopentyl), $C_{3-6}$cycloalkyl$C_{1-4}$alkyl (including cyclopropylmethyl), $C_{1-4}$alkoxy$C_{1-4}$alkyl (including ethoxymethyl), amino$C_{1-4}$alkyl (including 2-aminoethyl), $C_{2-4}$alkenyl (including 2-methylprop-2-en-1-yl), cyclohex-2- en-1-yl, phenyl, benzyl, p-toluenesulfonyl, 2-pyridylmethyl, 3-pyridylmethyl and 4-pyridylmethyl. In a particular embodiment $R^9$ represents 2,2,2-trifluoroethyl.

Groups represented by $R^{10}$ and fused rings formed by two adjacent $R^{10}$ groups may be attached at any available position, including positions contained within Z and the position to which the triazole ring is attached.

Preferred identities for $R^{10}$ include $C_{1-4}$alkyl (especially methyl), polyfluoro$C_{1-4}$alkyl (especially $CF_3$), benzyl, phenyl and cyclohexyl. When more than one $R^{10}$ is present, preferably at least one $R^{10}$ is alkyl or two $R^{10}$ groups complete a ring as described above. Examples of fused rings completed by two $R^{10}$ groups include benzene, naphthalene, cyclopentane, cyclohexane, pyridine, thiophene and furan, any of which is optionally substituted as indicated above. Preferred substituents include halogen, $NO_2$, $C_{1-4}$alkyl, phenyl, polyfluoro$C_{1-4}$alkyl, $C_{1-4}$alkoxy and polyfluoro$C_{1-4}$alkoxy. Preferably not more than one phenyl or $NO_2$ substituent is present.

In a particular embodiment of this subset, two $R^{10}$ groups complete a fused benzene ring optionally substituted with phenyl or $NO_2$ or with up to 2 substituents selected from halogen, $C_{1-4}$alkyl, polyfluoro$C_{1-4}$alkyl, $C_{1-4}$alkoxy and polyfluoro$C_{1-4}$alkoxy. Within this embodiment, Z very suitably represents $CH_2CH_2$.

A subset of the compounds of the invention consists of the compounds of formula II:

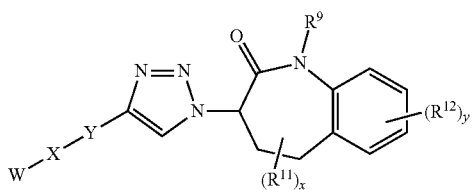

and the pharmaceutically acceptable salts or hydrates thereof; wherein x is 0, 1 or 2;
y is 0, 1 or 2;
$R^{11}$ represents methyl or phenyl with the proviso that x is not 2 when $R^{11}$ is phenyl,
each $R^{12}$ is independently selected from phenyl, $NO_2$ halogen, $C_{1-4}$alkyl, polyfluoro$C_{1-4}$alkyl, $C_{1-4}$-alkoxy and polyfluoro$C_{1-4}$alkoxy with the provision that not more than one $R^{12}$ represents phenyl or $NO_2$;
and $R^9$, W, X and Y have the same definitions and preferred identities as before.

When x is 2, the methyl groups may be attached at the same or different positions. In a particular embodiment x is 0.

Preferred identities for $R^{12}$ include halogen (especially F, Cl and Br), methyl, methoxy, $CF_3$, and $OCF_3$. In a particular embodiment y is 0 or y is 1 and $R^{12}$ is a fluorine substituent in the 6-position of the benzazepinone system.

Triazoles of formula I may be prepared by reaction of an azide of formula (1) with an alkyne of formula (2):

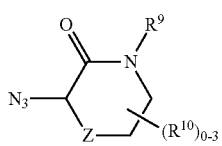

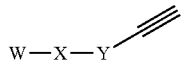

where Z, $R^9$, $R^{10}$, W, X and Y have the same meanings as before. The reaction takes place at ambient temperature in aqueous ethanol or DMF in the presence of copper(II) sulphate and sodium ascorbate.

Azides (1) may be prepared from the corresponding halides by reaction with sodium azide in ethanol or DMF. Procedures for the preparation of azides (1) are disclosed in WO 92/16524 and *J. Med. Chem.* 28, 1511 (1985).

Compounds (2) in which X is a bond and Y is an aryl ring may be prepared by Suzuki coupling of boronic acid derivatives (3a) with aryl halides (4a):

or by analogous coupling of boronic acid derivatives (4b) with halides (3b):

where each R independently represents H or $C_{1-6}$alkyl, or the two R groups complete a cyclic boronate ester such as pinacolate, Hal represents halogen (in particular iodine) and W and Y have the same meanings as before. The reaction takes place under standard Suzuki conditions, e.g. in a mixture of water, toluene and methanol with microwave heating in the presence of alkali metal carbonate and a triarylphosphine —Pd(0) catalyst.

Corresponding compounds (2) in which X is $(CH_2)_n NH$ are obtainable by coupling of amines (5):

with halides (4a), where W and n have the same meanings as before. The reaction takes place under Buchwald-Hartwig conditions, e.g. in a solvent such as DMF or t-amyl alcohol in the presence of strong base and a Pd-phosphine catalyst with microwave heating.

Similarly, compounds (2) in which X is $(CH_2)_n O$ are obtainable by coupling of hydroxyl compounds (6):

with halides (4a), where W and n have the same meanings as before. The reaction takes place with heating in the presence of cesium carbonate and cuprous chloride.

Corresponding compounds (2) in which X is $(CH_2)_n NHCO$ are obtainable by reaction of amines (5), halides (4a) and molybdenum hexacarbonyl, where W and n have the same meanings as before. The reaction takes place with heating in the presence of strong base (e.g. DBU), and a Pd-phosphine catalyst system.

In an alternative route to the compounds of formula I, alkynes (4a) or (4b) are reacted with azides (1) to form the triazole ring, followed by coupling with (3a), (3b), (5) or (6) as appropriate by the methods outlined above.

Compounds of formula I in which Y is C≡C may be obtained by reaction of an azide (1) with 4-(triethylsilanyl) butane-1,3-diyne to give the corresponding triazole, followed by removal of the silyl protecting group and coupling with a halide (3b).

Compounds of formula I in which Y is 4-piperidyl may be obtained by reaction of an azide (1) with N—BOC-4-ethynylpiperidine to form the triazole, followed by removal of the BOC protecting group and coupling with a halide (3b) or with and acid chloride W—COCl, where W has the same meaning as before.

Where they are not commercially-available, the alkynes (4a) and (4b) may be obtained form the corresponding aldehydes by reaction with dimethyl (1-diazo-2-oxopropyl)phosphonate, e.g. in anhydrous methanol in the presence of anhydrous potassium carbonate. Alternatively, they may be obtained from the corresponding bromides by reaction with tributyl(ethynyl)tin or trimethylsilylacetylene in the presence of $Pd(PPh)_4$.

It will be readily apparent to those skilled in the art that individual compounds in accordance with formula I may be converted to further compounds of formula I using the normal techniques of organic synthesis such as oxidation, reduction, alkylation, condensation and coupling. For example, a compound of formula I in which $R^9$ is H may be N-alkylated, N-acylated or N-sulfonylated by conventional techniques to provide the corresponding compounds in which $R^9$ is other than H. As an example there may be cited the treatment of a compound of formula I in which $R^9$ is H with strong base (such as sodium hydride or caesium carbonate) followed by trifluoroethyl triflate to provide the N-trifluoroethyl derivative. Similar procedures may be carried out on intermediates such as the compounds (1).

Where they are not themselves commercially available, the starting materials for the synthetic schemes described above are available by straightforward chemical modifications of commercially available materials.

Certain compounds according to the invention may exist as optical isomers due to the presence of one or more chiral centres or because of the overall asymmetry of the molecule. Such compounds may be prepared in racemic form, or individual enantiomers may be prepared either by enantiospecific synthesis or by resolution. The novel compounds may, for example, be resolved into their component enantiomers by standard techniques such as preparative HPLC, or the formation of diastereomeric pairs by salt formation with an optically active acid, such as di-p-toluoyl-D-tartaric acid and/or di-p-toluoyl-L-tartaric acid, followed by fractional crystallisation and regeneration of the free base. The novel compounds may also be resolved by formation of diastereomeric esters or amides, followed by chromatographic separation and removal of the chiral auxiliary. Alternatively, racemic intermediates in the preparation of compounds of formula I may be resolved by the aforementioned techniques, and the desired enantiomer used in subsequent steps.

In the compounds of generic Formulas I and II, the atoms may exhibit their natural isotopic abundances, or one or more of the atoms may be artificially enriched in a particular isotope having the same atomic number, but an atomic mass or mass number different from the atomic mass or mass number predominantly found in nature. The present invention is meant to include all suitable isotopic variations of the compounds of generic Formulas I and II. For example, different isotopic forms of hydrogen (H) include protium ($^1H$) and deuterium ($^2H$). Protium is the predominant hydrogen isotope found in nature. Enriching for deuterium may afford certain therapeutic advantages, such as increasing in vivo half-life or reducing dosage requirements, or may provide a compound useful as a standard for characterization of biological samples. Isotopically-enriched compounds within generic Formulas I and II can be prepared without undue experimentation by conventional techniques well known to those skilled in the art or by processes analogous to those described in the Schemes and Examples herein using appropriate isotopically-enriched reagents and/or intermediates.

During any of the above synthetic sequences it may be necessary and/or desirable to protect sensitive or reactive groups on any of the molecules concerned. This may be achieved by means of conventional protecting groups, such as those described in Protective Groups in Organic Chemistry, ed. J. F. W. McOmie, Plenum Press, 1973; and T. W. Greene & P. G. M. Wuts, Protective Groups in Organic Synthesis, John Wiley & Sons, $3^{rd}$ ed., 1999. The protecting groups may be removed at a convenient subsequent stage using methods known from the art.

The compounds of the invention have the useful property of modifying the action of γ-secretase on amyloid precursor protein so as to selectively reduce the formation of the 1-42 isoform of Aβ, and hence find use in the development of treatments for diseases mediated by Aβ(1-42), in particular diseases involving deposition of β-amyloid in the brain.

According to a further aspect of the invention there is provided the use of a compound according to formula I as defined above, or a pharmaceutically acceptable salt or hydrate thereof, for the manufacture of a medicament for treatment or prevention of a disease associated with the deposition of β-amyloid in the brain.

The disease associated with deposition of Aβ in the brain is typically Alzheimer's disease (AD), cerebral amyloid angiopathy, HCHWA-D, multi-infarct dementia, dementia pugilistica or Down syndrome, preferably AD.

In a further aspect, the invention provides the use of a compound of Formula I as defined above, or a pharmaceutically acceptable salt or hydrate thereof, in the manufacture of a medicament for treating, preventing or delaying the onset of dementia associated with Alzheimer's disease, cerebral amyloid angiopathy, HCHWA-D, multi-infarct dementia, dementia pugilistica or Down syndrome.

The invention also provides a method of treating or preventing a disease associated with deposition of Aβ in the brain comprising administering to a patient in need thereof a therapeutically effective amount of a compound of Formula I as defined above or a pharmaceutically acceptable salt or hydrate thereof.

In a further aspect, the invention provides a method of treating, preventing or delaying the onset of dementia associated with Alzheimer's disease, cerebral amyloid angiopathy, HCHWA-D, multi-infarct dementia, dementia pugilistica or Down syndrome comprising administering to a patient in need thereof a therapeutically effective amount of a compound of Formula I as defined above or a pharmaceutically acceptable salt or hydrate thereof.

The compounds of Formula I modulate the action of γ-secretase so as to selectively attenuate production of the (1-42) isoform of Aβ without significantly lowering production of the shorter chain isoforms such as Aβ(1-40). This results in secretion of Aβ which has less tendency to self-aggregate and form insoluble deposits, is more easily cleared from the brain, and/or is less neurotoxic. Therefore, a further aspect of the invention provides a method for retarding, arresting or preventing the accumulation of Aβ in the brain comprising administering to a subject in need thereof a therapeutically effective amount of a compound of Formula I as defined above or a pharmaceutically acceptable salt thereof.

Because the compounds of formula I modulate the activity of γ-secretase, as opposed to suppressing said activity, it is believed that the therapeutic benefits described above will be obtained with a reduced risk of side effects, e.g. those that might arise from a disruption of other signalling pathways (e.g. Notch) which are controlled by γ-secretase.

In one embodiment of the invention, the compound of Formula I is administered to a patient suffering from AD, cerebral amyloid angiopathy, HCHWA-D, multi-infarct dementia, dementia pugilistica or Down syndrome, preferably AD.

In an alternative embodiment of the invention, the compound of Formula I is administered to a patient suffering from mild cognitive impairment or age-related cognitive decline. A favourable outcome of such treatment is prevention or delay of the onset of AD. Age-related cognitive decline and mild cognitive impairment (MCI) are conditions in which a memory deficit is present, but other diagnostic criteria for dementia are absent (Santacruz and Swagerty, *American Family Physician*, 63 (2001), 703-13). (See also "The ICD-10 Classification of Mental and Behavioural Disorders", Geneva: World Health Organisation, 1992, 64-5). As used herein, "age-related cognitive decline" implies a decline of at least six months' duration in at least one of: memory and learning; attention and concentration; thinking; language; and visuospatial functioning and a score of more than one standard deviation below the noun on standardized neuropsychologic testing such as the MMSE. In particular, there may be a progressive decline in memory. In the more severe condition MCI, the degree of memory impairment is outside the range considered normal for the age of the patient but AD is not present. The differential diagnosis of MCI and mild AD is described by Petersen et al., *Arch. Neurol.*, 56 (1999), 303-8. Further information on the differential diagnosis of MCI is provided by Knopman et al, *Mayo Clinic Proceedings*, 78 (2003), 1290-1308. In a study of elderly subjects, Tuokko et al (*Arch, Neurol.*, 60 (2003) 577-82) found that those exhibiting MCI at the outset had a three-fold increased risk of developing dementia within 5 years.

Grundman et al (*J. Mol. Neurosci.*, 19 (2002), 23-28) report that lower baseline hippocampal volume in MCI patients is a prognostic indicator for subsequent AD. Similarly, Andreasen et al (*Acta Neural. Scand*, 107 (2003) 47-51) report that high CSF levels of total tau, high CSF levels of phospho-tau and lowered CSF levels of Aβ42 are all associated with increased risk of progression from MCI to AD.

Within this embodiment, the compound of Formula I is advantageously administered to patients who suffer impaired memory function but do not exhibit symptoms of dementia. Such impairment of memory function typically is not attributable to systemic or cerebral disease, such as stroke or metabolic disorders caused by pituitary dysfunction. Such patients may be in particular people aged 55 or over, especially people aged 60 or over, and preferably people aged 65 or over. Such patients may have normal patterns and levels of growth hormone secretion for their age. However, such patients may possess one or more additional risk factors for developing Alzheimer's disease. Such factors include a family history of the disease; a genetic predisposition to the disease; elevated serum cholesterol; and adult-onset diabetes mellitus.

In a particular embodiment of the invention, the compound of Formula I is administered to a patient suffering from age-related cognitive decline or MCI who additionally possesses one or more risk factors for developing AD selected from: a family history of the disease; a genetic predisposition to the disease; elevated serum cholesterol; adult-onset diabetes mellitus; elevated baseline hippocampal volume; elevated CSF levels of total tau; elevated CSF levels of phospho-tau; and lowered CSF levels of Aβ(1-42), A genetic predisposition (especially towards early onset AD) can arise from point mutations in one or more of a number of genes, including the APP, presenilin-1 and presenilin-2 genes. Also, subjects who are homozygous for the ε4 isoform of the apolipoprotein E gene are at greater risk of developing AD.

The patient's degree of cognitive decline or impairment is advantageously assessed at regular intervals before, during and/or after a course of treatment in accordance with the invention, so that changes therein may be detected, e.g. the slowing or halting of cognitive decline. A variety of neuropsychological tests are known in the art for this purpose, such as the Mini-Mental State Examination (MMSE) with norms adjusted for age and education (Folstein et al., *J. Psych. Res.*, 12 (1975), 196-198, Anthony et al., *Psychological Med.*, 12 (1982), 397-408; Cockrell et al., *Psychopharmacology*, 24 (1988), 689-692; Crum et al., *J. Am. Med. Assoc'n.* 18 (1993), 2386-2391). The MMSE is a brief, quantitative measure of cognitive status in adults. It can be used to screen for cognitive decline or impairment, to estimate the severity of cognitive decline or impairment at a given point in time, to follow the course of cognitive changes in an individual over time, and to document an individual's response to treatment. Another suitable test is the Alzheimer Disease Assessment Scale (ADAS), in particular the cognitive element thereof (ADAS-cog) (See Rosen et al, *Am. J. Psychiatry*, 141 (1984), 1356-64).

The compounds of Formula I are typically used in the form of pharmaceutical compositions comprising one or more compounds of Formula I and a pharmaceutically acceptable carrier. Accordingly, in a further aspect the invention provides a pharmaceutical composition comprising a compound of formula I as defined above, or a pharmaceutically acceptable salt or hydrate thereof, and a pharmaceutically acceptable carrier. Preferably these compositions are in unit dosage fours such as tablets, pills, capsules, powders, granules, sterile parenteral solutions or suspensions, metered aerosol or liquid sprays, drops, ampoules, transdermal patches, auto-injector devices or suppositories; for oral, parenteral, intranasal, sublingual or rectal administration, or for administration by inhalation or insufflation. The principal active ingredient typically is mixed with a pharmaceutical carrier, e.g. conventional tableting ingredients such as corn starch, lactose, sucrose, sorbitol, talc, stearic acid, magnesium stearate and dicalcium phosphate, or gums, dispersing agents, suspending agents or surfactants such as sorbitan monooleate and polyethylene glycol, and other pharmaceutical diluents, e.g. water, to form a homogeneous preformulation composition containing a compound of the present invention, or a pharmaceutically acceptable salt thereof. When referring to these preformulation compositions as homogeneous, it is meant that the active ingredient is dispersed evenly throughout the composition so that the composition may be readily subdivided into equally effective unit dosage forms such as tablets, pills and capsules. This preformulation composition is then subdivided into unit dosage forms of the type described above containing from 0.1 to about 500 mg of the active ingredient of the present invention. Typical unit dosage forms contain from 1 to 100 mg, for example 1, 2, 5, 10, 25, 50 or 100 mg, of the active ingredient. Tablets or pills of the composition can be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer which serves to resist disintegration in the stomach and permits the inner component to pass intact into the duodenum or to be delayed in release. A variety of materials can be used for such enteric layers or coatings, such materials including a number of polymeric acids and mixtures of polymeric acids with such materials as shellac, cetyl alcohol and cellulose acetate.

The liquid forms in which the compositions useful in the present invention may be incorporated for administration orally or by injection include aqueous solutions, liquid- or gel-filled capsules, suitably flavoured syrups, aqueous or oil suspensions, and flavoured emulsions with edible oils such as cottonseed oil, sesame oil, coconut oil or peanut oil, as well as elixirs and similar pharmaceutical vehicles. Suitable dispersing or suspending agents for aqueous suspensions include synthetic and natural gums such as tragacanth, acacia, alginate, dextran, sodium carboxymethylcellulose, methylcellulose, polyethylene glycol), poly(vinylpyrrolidone) or gelatin.

For treating or preventing Alzheimer's disease, a suitable dosage level is about 0.01 to 250 mg/kg per day, preferably about 0.01 to 100 mg/kg per day, and more preferably about 0.05 to 50 mg/kg of body weight per day, of the active compound. The compounds may be administered on a regimen of 1 to 4 times per day. In some cases, however, a dosage outside these limits may be used.

The compounds of Formula I optionally may be administered in combination with one or more additional compounds known to be useful in the treatment or prevention of AD or the symptoms thereof. Such additional compounds thus include cognition-enhancing drugs such as acetylcholinesterase inhibitors (e.g. donepezil and galanthamine), NMDA antagonists (e.g. memantine) or PDE4 inhibitors (e.g. Ariflo™ and the classes of compounds disclosed in WO 03/018579, WO 01/46151, WO 02/074726 and WO 02/098878). Such additional compounds also include cholesterol-lowering drugs such as the statins, e.g. simvastatin. Such additional compounds similarly include compounds known to modify the production or processing of $A\beta$ in the brain ("amyloid modifiers"), such as compounds which inhibit the secretion of $A\beta$ (including $\gamma$-secretase inhibitors, $\beta$-secretase inhibitors, and GSK-3$\alpha$ inhibitors), compounds which inhibit the aggregation of $A\beta$, and antibodies which selectively bind to $A\beta$. Such additional compounds also include growth hormone secretagogues, as disclosed in WO 2004/110443.

In this embodiment of the invention, the amyloid modifier may be a compound which inhibits the secretion of $A\beta$, for example an inhibitor of $\gamma$-secretase (such as those disclosed in WO 01/90084, WO 02/30912, WO 01/70677, WO 03/013506, WO 02/36555, WO 03/093252, WO 03/093264, WO 03/093251, WO 03/093253, WO 2004/039800, WO 2004/039370, WO 2005/030731, WO 2005/014553, WO 2004/089911, WO 02/081435, WO 02/081433, WO 03/018543, WO 2004/031137, WO 2004/031139, WO 2004/031138, WO 2004/101538, WO 2004/101539 and WO 02/47671), or a $\beta$-secretase inhibitor (such as those disclosed in WO 03/037325, WO 03/030886, WO 03/006013, WO 03/006021, WO 03/006423, WO 03/006453, WO 02/002122, WO 01/70672, WO 02/02505, WO 02/02506, WO 02/02512, WO 02/02520, WO 02/098849 and WO 02/100820), or any other compound which inhibits the formation or release of $A\beta$ including those disclosed in WO 98/28268, WO 02/47671, WO 99/67221, WO 01/34639, WO 01/34571, WO 00/07995, WO 00/38618, WO 01/92235, WO 01/77086, WO 01/74784, WO 01/74796, WO 01/74783, WO 01/60826, WO 01/19797, WO 01/27108, WO 01/27091, WO 00/50391, WO 02/057252, US 2002/0025955 and US2002/0022621, and also including GSK-3 inhibitors, particularly GSK-3$\alpha$ inhibitors, such as lithium, as disclosed in Phiel et al, *Nature,* 423 (2003), 435-9.

Alternatively, the amyloid modifier may be a compound which inhibits the aggregation of $A\beta$ or otherwise attenuates is neurotoxicicity. Suitable examples include chelating agents such as clioquinol (Gouras and Beal, *Neuron,* 30 (2001), 641-2) and the compounds disclosed in WO 99/16741, in particular that known as DP-109 (Kalendarev et al, *J. Pharm. Biomed. Anal.,* 24 (2001), 967-75). Other inhibitors of $A\beta$ aggregation suitable for use in the invention include the compounds disclosed in WO 96/28471, WO 98/08868 and WO 00/052048, including the compound known as Apan™ (Praecis); WO 00/064420, WO 03/017994, WO 99/59571 (in particular 3-aminopropane-1-sulfonic acid, also known as tramiprosate or Alzhemed™); WO 00/149281 and the compositions known as PTI-777 and PTI-00703 (Preteo Tech); WO 96/39834, WO 01/83425, WO 01/55093, WO 00/76988, WO 00/76987, WO 00/76969, WO 00/76489, WO 97/26919, WO 97/16194, and WO 97/16191. Further examples include phytic acid derivatives as disclosed in U.S. Pat. No. 4,847,082 and inositol derivatives as taught in US 2004/0204387.

Alternatively, the amyloid modifier may be an antibody which binds selectively to $A\beta$. Said antibody may be polyclonal or monoclonal, but is preferably monoclonal, and is preferably human or humanized. Preferably, the antibody is capable of sequestering soluble $A\beta$ from biological fluids, as described in WO 03/016466, WO 03/016467, WO 03/015691 and WO 01/62801. Suitable antibodies include humanized antibody 266 (described in WO 01/62801) and the modified version thereof described in WO 03/016466.

As used herein, the expression "in combination with" requires that therapeutically effective amounts of both the compound of Formula I and the additional compound are administered to the subject, but places no restriction on the manner in which this is achieved. Thus, the two species may be combined in a single dosage form for simultaneous administration to the subject, or may be provided in separate dosage forms for simultaneous or sequential administration to the subject. Sequential administration may be close in time or remote in time, e.g. one species administered in the morning and the other in the evening. The separate species may be administered at the same frequency or at different frequencies, e.g. one species once a day and the other two or more times a day. The separate species may be administered by the same route or by different routes, e.g. one species orally and the other parenterally, although oral administration of both species is preferred, where possible. When the additional compound is an antibody, it will typically be administered parenterally and separately from the compound of Formula I.

EXPERIMENTAL

The ability of the compounds of Formula I to selectively inhibit production of $A\beta(1-42)$ may be determined using the following assay:

Cell-Based $\gamma$-Secretase Assay

Human SH-SY5Y neuroblastoma cells overexpressing the direct $\gamma$-secretase substrate SPA4CT were induced with sodium butyrate (10 mM) for 4 hours prior to plating. Cells were plated at 35,000 cells/well/100 µl in 96-well plates in phenol red-free MEM/10% FBS, 50 mM HEPES, 1% Glutamine and incubated for 2 hrs at 37° C., 5% $CO_2$.

Compounds for testing were diluted into $Me_2SO$ to give a ten point dose-response curve. Typically 10 µl of these diluted compounds in $Me_2SO$ were further diluted into 182 µl dilution buffer (phenol red-free MEM/10% FBS, 50 mM HEPES, 1% Glutamine) and 10 µl of each dilution was added to the cells in 96-well plates (yielding a final $Me_2SO$ concentration of 0.5%). Appropriate vehicle and inhibitor controls were used to determine the window of the assay.

After incubation overnight at 37° C., 5% $CO_2$, 25 µl and 50 µmedia were transferred into a standard Meso avidin-coated 96-well plate for detection of $A\beta(40)$ and $A\beta(42)$ peptides, respectively. 25 µl Meso Assay buffer (PBS, 2% BSA, 0.2% Tween-20) was added to the Aβ(40) wells followed by the addition of 25 µl of the respective antibody premixes to the wells:

Aβ(40) premix: 1 µg/ml ruthenylated G2-10 antibody, 4 µg/ml; and biotinylated 4G8 antibody diluted in Origen buffer Aβ(42) premix: 1 µg/ml ruthenylated G2-11 antibody, 4 µg/ml; and biotinylated 4G8 antibody diluted in Origen buffer (Biotinylated 4G8 antibody supplied by Signet Pathology Ltd; G2-10 and G2-11 antibodies supplied by Chemicon)

After overnight incubation of the assay plates on a shaker at 4° C., the Meso Scale Sector 6000 Imager was calibrated according to the manufacturer's instructions. After washing the plates 3 times with 150 µl of PBS per well, 150 µl Meso Scale Discovery read buffer was added to each well and the plates were read on the Sector 6000 Imager according to the manufacturer's instructions.

Cell viability was measured in the corresponding cells after removal of the media for the Aβ assays by a colorimetric cell proliferation assay (CellTiter 96™ AQ assay, Promega) utilizing the bioreduction of MTS (Owen's reagent) to formazan according to the manufacturer's instructions. Briefly, 5 µl of 10×MTS/PES was added to the remaining 50 µl of media before returning to the incubator. The optical density was read at 495 nm after ~4 hours.

$LD_{50}$ and $IC_{50}$ values for inhibition of Aβ(40) and Aβ(42) were calculated by nonlinear regression fit analysis using the appropriate software (eg. Excel fit). The total signal and the background were defined by the corresponding $Me_2SO$ and inhibitor controls.

The compounds listed in the following examples all gave $IC_{50}$ values for Aβ(1-42) inhibition of less than 5 µM, in most cases less than 1.0 µM, and in many cases less than 0.5 µM. Furthermore, said values were at least 2-fold lower than the corresponding $IC_{50}$ values for Aβ(1-40) inhibition, typically at least 5-fold lower. The following table records $IC_{50}$ values for Aβ(1-42) inhibition for representative examples:

| Example No. | $IC_{50}$ Aβ(1-42) (nM) |
| --- | --- |
| 1 | 80 |
| 2 | 1333 |
| 57 | 431 |
| 61 | 537 |
| 92 | 226 |
| 117 | 145 |
| 123 | 83 |

Assay for In Vivo Efficacy

APP-YAC transgenic mice (20-30 g; 2-6 months old) and Sprague Dawley rats (200-250 g; 8-10 weeks old) are kept on 12-hr light/dark cycle with unrestricted access to food and water. Mice and rats are fasted overnight and are then dosed orally at 10 ml/kg with test compound formulated in either Imwitor:Tween-80 (50:50) or 10% Tween-80, respectively. For compound screening studies, test compounds are administered at a single dose (20 or 100 mg/kg) and blood taken serially at 1 and 4 hrs via tail bleed from mice and terminally at 7 hrs for mice and rats via cardiac puncture. In dose response studies, compounds are given at 0.1, 3, 10, 30, and 100 mg/kg and blood taken terminally at 7 hrs from mice and rats via cardiac puncture. Following euthanasia by $CO_2$, forebrain tissue is harvested from animals and stored at −80 degrees. For PD analysis of brain Aβ levels, soluble Aβ is extracted from hemi-forebrains by homogenization in 10 volumes of 0.2% DEA in 50 mM NaCl followed by ultracentrifugation. Levels of Aβ 42/40 are analyzed using Meso Scale technology (electrochemiluminesence) with biotinylated 4G8 capture antibody and ruthenium labeled 12F4 or G210 detection antibodies for Aβ 42 and Aβ 40, respectively. For PK analysis, blood and brain samples are processed using a protein precipitation procedure with the remaining filtrate being analyzed via LC/MS/MS to determine drug exposure levels, brain penetration, and ED50/EC50, where appropriate.

Reductions in Aβ42 levels (relative to vehicle-treated controls) for representative compounds of the invention are in the range 50-90% whereas corresponding reductions in Aβ40 levels for the same compounds are 20-50%.

Preparation of Starting Materials and Intermediates

General Procedure 1 (GP 1)—Halogenation of Lactams

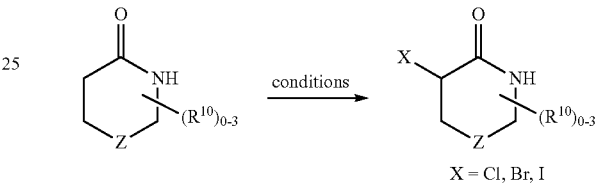

X = Cl, Br, I a) Chlorination:

Lactam (1 eq) and phosphorus pentachloride (2 eq) were placed in a round bottom flask under nitrogen and benzene (anhydrous, 2.5 M) was added. The reaction mixture was heated to 100° C. for 1.5 h. After cooling to room temperature the volatiles were removed and the remaining solid quenched with ice (caution!). Water was added and the precipitating grey solid collected on a filter frit. The chloro lactam was dried on high vacuum and used as such in the subsequent step.

b) Bromination:

To a lactam (1 eq) and phosphorus pentachloride (1 eq) in a round bottom flask was added anhydrous chloroform (~0.25 M) and the resulting solution stirred for 30 minutes. Iodine (0.1 eq) was added and after 5-10 minutes drop-wise bromine (1 eq). The reaction was then stirred for 16 hours. Ice was added and the mixture was extracted with dichloromethane three times. The combined organic fractions were washed with brine, dried ($MgSO_4$), filtered and the solvent was evaporated under reduced pressure. The crude material was used without purification in the subsequent step, but can be purified by chromatography on silica gel.

c) Iodination:

To a solution of lactam in dichloromethane (0.2 M) at −15° C. was added N,N,N',N'-tetramethylethylenediamine (4 eq), then at the same temperature, iodotrimethylsilane (4 eq) was added dropwise. The mixture was stirred for 10 min at −15° C. Iodine (2 eq) was added to this mixture in one portion and the mixture was stirred at 0° C. for 2 hours or until complete by LCMS. The mixture was diluted with dichloromethane, washed with sodium thiosulfate (sat. aqueous), dried over magnesium sulfate, filtered and concentrated to afford crude product, which was purified on silica gel (EtOAc/hexane) to afford desired product.

General Procedure 2 (GP 2)—Preparation of Azides

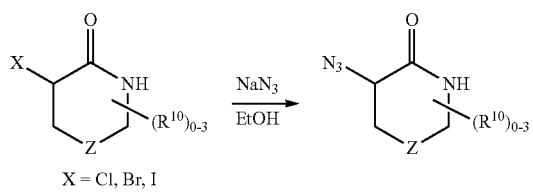

X = Cl, Br, I

The halide (1.0 eq) and sodium azide (1.2-3 eq; caution, very toxic) were placed in a round bottom flask and ethanol or DMF (DMA, DMPU for unactivated and hindered substrates) were added to give an approximately 0.2 M solution. The mixture was stirred for 16 h at room temperature or up to 80° C. for less reactive electrophiles. The reaction mixture was then filtered through a 0.45 µM filter and used directly, or preferably worked-up according to the following procedure: water was added and the mixture extracted with methylene chloride twice. The combined organic layers were evaporated under reduced pressure without heating (caution: organic azides are explosive). The crude azide was used directly without further purification in the subsequent step according to GP 3.

General Procedure 3 (GP 3)—Preparation of Triazoles (Click Chemistry)

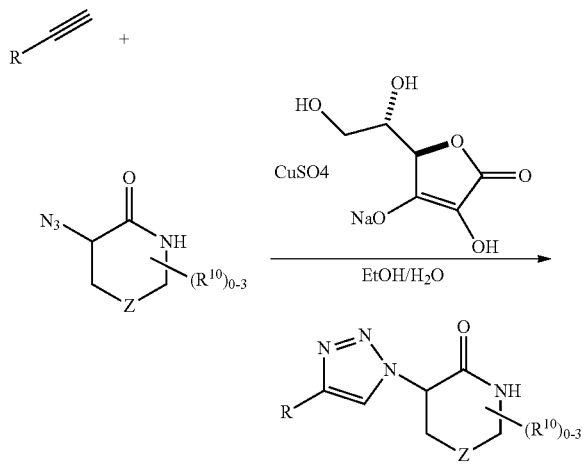

Alkyne, azide, water and ethanol (or DMF) were placed in a round bottom flask and aqueous copper sulfate solution (1M, 10-100 mol %) and aqueous sodium ascorbate solution (1M, 20-100 mol %) was added. The reaction mixture was stirred at room temperature until complete (more copper sulfate solution and sodium ascorbate solution were added as needed), then the solvents were removed under reduced pressure. The residue was purified by reversed phase chromatography (C18, acetonitrile/water with 0.1% TFA).

General Procedure 4 (GP 4)—Suzuki Cross-Coupling

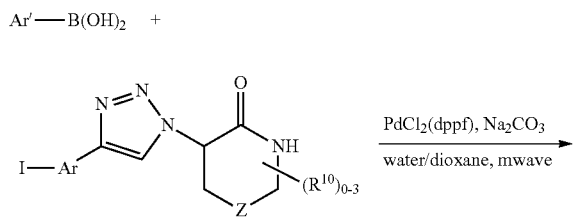

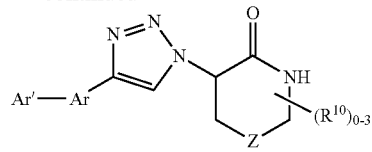

Iodoaryl compound (1 eq) was added to a 20 ml µwave vial along with a boronic acid (2 eq), $PdCl_2(dppf)$ (20 mol %), 2M sodium carbonate in water (2 eq) and water/dioxane (1:5; 0.05-0.1 M). The vial was sealed and µwaved at 100° C. for 10 minutes. The reaction mixture was filtered through a plug of Celite. The plug was washed with 100 ml of dioxane and the filtrates were combined and concentrated under reduced pressure. The contents of the flask were reconstituted in water and extracted with dichloromethane twice. The organic layers were combined, passed through a phase separator cartridge, and concentrated under reduced pressure. The residue was dissolved in DMSO and purified by reverse phase chromatography (C18, MeCN/water).

General Procedure 5 (GP 5): Carbonyl Insertion

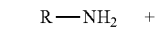
R—$NH_2$ +

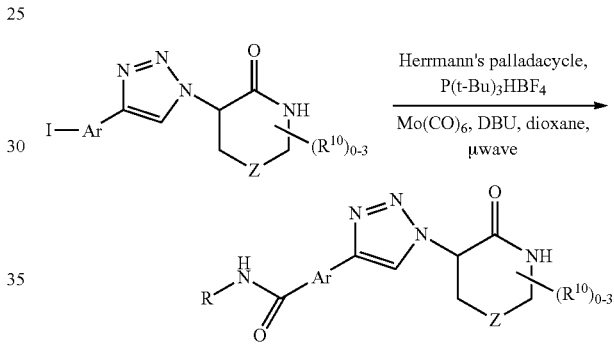

Iodoaryl compound (1 eq), amine (2.5 eq), DBU (15 eq), $Mo(CO)_6$, $P(tBu)_3HBF_4$ salt (2.59 mg, 8.92 µmol) and Hermann's Palladacycle (4.18 mg, 4.46 µmmol) combined in dioxane (1.487 ml) in a microwave vial. The vial was sealed and microwaved at 140° C. for 12 minutes. The reaction mixture was dried in vacuo. Analytically pure material was obtained by purification by preparative HPLC Reverse phase (C-18), eluting with acetonitrile/water+0.05% formic acid.

Synthesis of 3-azido-6-fluoro-1-(2,2,2-trifluoroethyl)-1,3,4,5-tetrahydro-2H-1-benzazepin-2-one

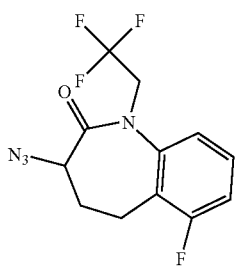 [SMILES: [N-]=[N+]=NC1CCc2c(F)cccc2N(CC(F)(F)F)C1=O]

3-Azido-6-fluoro-1,3,4,5-tetrahydro-2H-1-benzazepin-2-one (2.25 g, 10.22 mmol), cesium carbonate (4.65 g, 14.30 mmol), and 2,2,2-trifluoroethyl trifluoromethanesulfonate (2.67 mL, 18.39 mmol) in DMF (34.1 mL) heated to 40° C. for 1 hour. The reaction mixture was diluted with water before EtOAc was added to extract the product. The organic phase was separated and washed with water (2×) and brine (1×) before being dried with Na$_2$SO$_4$ and evaporated to yield the crude product. This material was chromatographed on silica gel (0-80% EtOAc in hexanes) to yield 2.534 g of 3-azido-6-fluoro-1-(2,2,2-trifluoroethyl)-1,3,4,5-tetrahydro-2H-1-benzazepin-2-one as an orange/brown solid.

$^1$H NMR (600 MHz, CDCl$_3$) δ 7.37-7.25 (m, 1H), 7.08-6.91 (m, 2H), 5.09 (dt, J=17.3, 8.6, 1H), 3.98 (td, J=15.6, 7.8, 1H), 3.78-3.59 (m, 1H), 3.18 (dd, J=13.8, 6.8, 1H), 2.57 (dd, J=20.6, 13.2, 114), 2.47-2.21 (m, 2H).

MS calculated 303.1 (MH$^+$), exp 303.0 (MH$^+$).

Syntheses of Alkynes 2-(4-Ethynyl-2-methoxy-phenyl)-5-methyl-1,3,4-oxadiazole

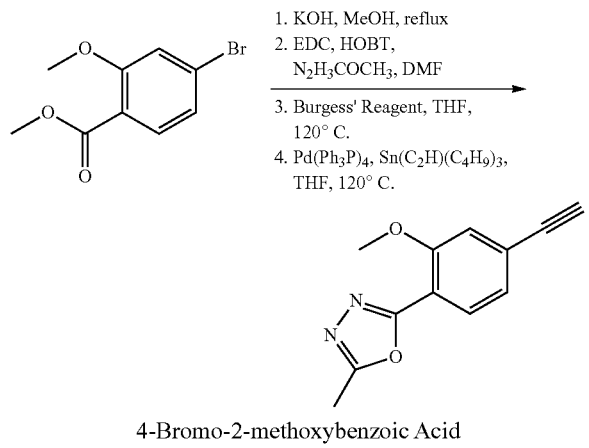

4-Bromo-2-methoxybenzoic Acid

A solution of methyl 4-bromo-2-methoxybenzoate (1 g, 4.08 mmol) in 20 ml of MeOH was treated with 4.08 ml of a 2 N solution of potassium hydroxide and refluxed at 65° C. for 2.5 hours. MeOH was removed in vacuo and the remaining water was taken-up in 100 ml of EtOAc and quenched with 30 ml of 1 N HCl (3.5 eq.) and 100 ml of water. Layers were separated and the aqueous layer was extracted twice with EtOAc. Organics were combined, dried over sodium sulfate, and concentrated under reduced pressure to a yellow-white solid (950.7 mg crude).

$^1$H NMR (500 MHz, CDCl$_3$) δ 10.38 (s, 1H), 8.05 (d, J=8.5 Hz, 1H), 7.30 (dd, J=8.5, 1.7 Hz, 1H), 7.22 (d, J=1.7 Hz, 1H), 4.09 (s, 3H).

N'-Acetyl-4-bromo-2-methoxybenzohydrazide

A solution of 4-bromo-2-methoxybenzoic acid (950.7 mg, 4.11 mmol) in 8 ml of DMF was treated sequentially with EDC (1183 mg, 6.17 mmol) and HOBT (945 mg, 6.17 mmol) and stirred at room temperature for 10 minutes. The reaction was then treated with acetic hydrazide (366 mg, 4.94 mmol) and stirred at room temperature overnight. The reaction was dissolved in EtOAc and washed sequentially with saturated bicarbonate solution and brine. The aqueous washes were extracted once with EtOAc. Organics were combined, dried over sodium sulfate, and concentrated under reduced pressure to a white solid (1.37 g crude).

$^1$H NMR (500 MHz, CDCl$_3$) δ 10.53 (s, 1H), 9.18 (s, 1H), 8.04 (d, J=8.4 Hz, 1H), 7.25 (dd, J=8.3, 1.7 Hz, 1H), 7.16 (d, J=1.7 Hz, 1H), 4.04 (s, 3H), 2.13 (s, 3H);

MS (EI) [M+1]$^+$ calc'd 287.0, 289.0. found 287.0, 289.0.

2-(4-Bromo-2-methoxyphenyl)-5-methyl-1,3,4-oxadiazole

N'-Acetyl-4-bromo-2-methoxybenzohydrazide (720 mg, 2.51 mmol) and Burgess' Reagent (896 mg, 3.76 mmol) were dissolved in 10 ml of THF and stirred in the microwave at 120° C. for 30 minutes. The reaction was diluted with brine and extracted three times with EtOAc. Organics were combined, dried over sodium sulfate, and concentrated under reduced pressure to a yellow oil. Chromatography on silica gel (0-50% EtOAc/DCM) gave a yellow solid (465 mg, 1.73 mmol, 69%).

$^1$H NMR (500 MHz, CDCl$_3$) δ 7.74-7.77 (m, 1H), 7.18-7.23 (m, 2H), 3.94-3.97 (m, 3H), 2.59-2.62 (m, 3H);

MS (EI) [M+1]$^+$ calc'd 269.0. found 268.9.

2-(4-Ethynyl-2-methoxyphenyl)-5-methyl-1,3,4-oxadiazole

Pd(Ph$_3$P)$_4$ (100 mg, 0.087 mmol) and ethynyltributylstannane (600 mg, 1.904 mmol) was treated with a solution of 2-(4-bromo-2-methoxyphenyl)-5-methyl-1,3,4-oxadiazole (457.7 mg, 1.701 mmol) in 10 ml of THF and heated to 120° C. for 15 minutes in a microwave. The reaction was dissolved in brine and extracted three times with EtOAc. Organics were combined, dried over sodium sulfate and concentrated under reduced pressure. Chromatography on silica gel (100% hexanes followed by 0-25% EtOAc/DCM) gave a cream-colored solid (180 mg, 0.850 mmol, 49%).

$^1$H NMR (500 MHz, CDCl$_3$) δ 7.87 (d, J=8.0 Hz, 1H), 7.19 (dd, J=8.0, 1.3 Hz, 1H), 7.15 (d, J=1.2 Hz, 1H), 3.97 (s, 3H), 3.23 (s, 1H), 2.62 (s, 3H);

MS (EI) [M+1]$^+$ calc'd 215.1. found 215.0.

4-(4-ethynyl-3-fluorophenyl)pyridine

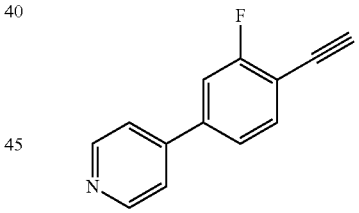

1-Bromo-2-fluoro-4-iodobenzene (300 mg, 0.997 mmol), 4-pyridineboronic acid (147 mg, 1.196 mmol), Na$_2$CO$_3$(211 mg, 1.994 mmol) and tetrakis(triphenylphosphine)palladium (230 mg, 0.199 mmol) in 3.3 mL of 1:1 Dioxane/water were heated to 100° C. for 20 h. The reaction was slowly warmed to room temperature, diluted with water and extracted with EtOAc. The organic phase was separated, dried (Na$_2$SO$_4$) and evaporated to dryness, giving an oil. This material was chromatographed on silica gel, eluting with 0-10% ethyl acetate in hexanes to give 4-(4-bromo-3-fluorophenyl)pyridine (55 mg) as an off-white solid.

$^1$H NMR (600 MHZ, CDCl$_3$) δ 8.66 (m, 2H), 7.64 (dd, J=7.2, 8.4 Hz, 1H), 7.43 (m, 2H), 7.37 (dd, 1.8, 8.4 Hz, 1H), 7.29 (dd, J=1.8, 7.2 Hz, 1H).

MS calculated 252.0 (MH$^+$), exp 251.9 (MH$^+$).

4-(4-bromo-3-fluorophenyl)pyridine (55 mg, 0.218 mmol), CuI (5.8 mg, 0.031 mmol), PdCl$_2$(PPh$_3$)$_2$ (23 mg, 0.033 mmol) were placed in a μwave tube under an atmosphere of N₂. TMS acetylene (46 μL, 0.327 mmol), Et₃N (121 μL, 0.873 mmol) and THF (1.1 mL) were added and the mixture was heated to 100° C. for 20 min and then cooled to ambient temperature. The mixture was filtered through a silica gel pack and washed with EtOAc. Combined eluents were evaporated under reduced pressure to give crude TMS acetylenic product as a solid. The crude material from step 1 was dissolved in MeOH (in some cases 20% EtOAc was added to increase solubility) and 3 eq of K₂CO₃ added and the mixture stirred for 30 min. To the mixture was added water and extracted with EtOAc. The combined organic layers were dried, filtered and evaporated. The residue was purified by column chromatography on silica to afford the title compound 29 mg (0.146 mmol).

¹H NMR (600 MHZ, CDCl₃) δ 8.67 (m, 2H), 7.58-7.34 (m, 5H), 3.38 (s, 1H).

MS calculated 198.1 (MH⁺), exp 198.1 (MH⁺).

5-(4-Ethynyl-3-methoxy-phenyl)-3-methyl-1,2,4-oxadiazole

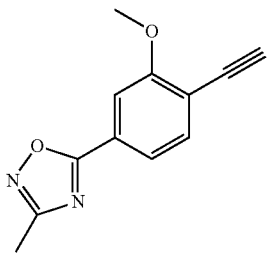 [SMILES: C#Cc1ccc(-c2nc(C)no2)cc1OC]

4-Bromo-3-methoxybenzamide (500 mg, 2.173 mmol) and N,N-dimethylacetamide dimethyl acetal (3 mL, 20.52 mmol) were heated at 125° C. for 2.5 h. The reaction was allowed to cool to room temperature and the volatiles evaporated to give a pale yellow solid.

To the solid material of step 1 was added hydroxylamine hydrochloride (181 mg, 2.61 mmol) in 1M NaOH (3.04 mL, 3.04 mmol), dioxane (3.4 mL) and AcOH (4.5 mL). The reaction was stirred at ambient temperature for 5 min and then heated at 90° C. for 3 h. The mixture was cooled to ambient temperature, poured into water and extracted with EtOAe. The organic layers were washed with sat. NaHCO₃. The combined organics were dried, filtered and solvent reduced by rotovap. The residue was purified by column chromatography on silica gel to give 5-(4-bromo-3-methoxyphenyl)-3-methyl-1,2,4-oxadiazole (445 mg).

¹H NMR (600 MHZ, CDCl₃) δ 7.68 (d, J=7.8 Hz, 1H), 7.58 (m 2H), 3.98 (s, 3H), 2.46 (s, 3H).

MS calculated 270.0 (MH⁺), exp 269.9 (MH⁺).

5-(4-Bromo-3-methoxyphenyl)-3-methyl-1,2,4-oxadiazole was converted to 5-(4-ethynyl-3-methoxy-phenyl)-3-methyl-1,2,4-oxadiazole via the method described for 4-(4-ethynyl-3-fluorophenyl)pyridine 3-(4-Ethynyl-3-methoxy-phenyl)-5-methyl-1,2,4-oxadiazole

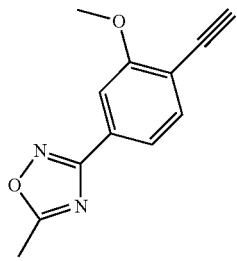 [SMILES: C#Cc1ccc(-c2noc(C)n2)cc1OC]

The mixture of 4-bromo-3-methoxybenzonitrile (800 mg, 3.77 mmol), hydroxylamine hydrochloride (524 mg, 7.55 mmol) and Et₃N (1.05 mL, 7.55 mmol) in EtOH (13 mL) was heated at 80° C. for 2.5 h. The mixture was cooled to ambient temperature, poured into water and extracted with EtOAc. The organic layers were washed with water. The combined organics were dried, filtered and solvent reduced by rotovap.

The residue from step 1 was dissolved in Ac₂O (7.1 mL, 75 mmol) and heated to 120° C. overnight. The reaction mixture was cooled and water was added and the mixture was extracted with EtOAc. The combined organic fractions were washed with sat. aq. NaHCO₃, dried, filtered and the solvent was evaporated under reduced pressure.

The residue was purified by column chromatography on silica gel (0-40% EtOAc in Hex) to afford 3-(4-bromo-3-methoxyphenyl)-5-methyl-1,2,4-oxadiazole (600 mg).

¹H NMR (600 MHZ, CDCl₃) δ 7.62 (d, J=8.4 Hz, 1H), 7.53 (m, 2H), 3.95 (s, 3H), 2.64 (s, 3H).

MS calculated 269.0 (MH⁺), exp 268.9 (MH⁺).

3-(4-Bromo-3-methoxyphenyl)-5-methyl-1,2,4-oxadiazole was converted to 3-(4-ethynyl-3-methoxy-phenyl)-5-methyl-1,2,4-oxadiazole via the method described for 4-(4-ethynyl-3-fluorophenyl)pyridine 4-(pyridine-3-yloxy)ethynylbenzene

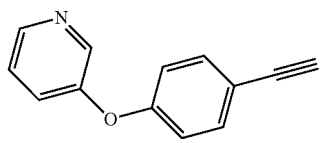

4-(Pyridine-3-yloxy)benzaldehyde (0.500 g, 2.510 mmol), 4-acetamidobenzene sulfonyl azide (0.724 g, 3.01 mmol), dimethyl (2-oxopropyl) phosphonate (0.412 mL, 3.01 mmol), and potassium carbonate (1.041 g, 7.53 mmol) in MeCN (10.5 mL) and MeOH (2.1 mL) was heated to 40° C. for 16 h while under N₂. The solvent was removed and residue was redissolved in EtOAc and washed with water (3×) and brine (1×). The organic phase was separated, dried with Na₂SO₄ and evaporated to afford an oil. This material was chromatographed on silica (0-80% EtOAc in hexanes) to yield 0.238 g as an oil.

MS calculated 196.1 (MH⁺), exp 196.0 (MH⁺).

3-(4-ethynyl-3-methoxyphenoxy)pyridine

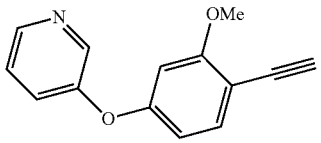 [SMILES: C#Cc1ccc(Oc2cccnc2)cc1OC]

4-Bromo-2-methoxybenzaldehyde (1.00 g, 4.65 mmol), cesium carbonate (3.03 g, 9.30 mmol), 3-hydroxypyridine (0.884 g, 9.30 mmol), cuprous chloride (0.230 g, 2.325 mmol), 2,2,6,6-tetramethyl-3,5-heptanedione (0.214 g, 1.163 mmol) in NMP (11.6 mL) in a sealed microwave vial was heated to 120° C. overnight in an oil bath. The reaction vessel was allowed to cool before water was added to dilute the mixture; EtOAc was then added to extract the product. The organic phase was separated and washed with water (2×) and brine (1×) before being dried with $Na_2SO_4$ and evaporated to afford an oil. This material was chromatographed on silica 0-80% EtOAc in hexanes to yield 4-(pyridine-3-yloxy)-2-methoxybenzaldehyde (0.665 g) as a solid.

MS calculated 230.1 ($MH^+$), exp 230.0 ($MH^+$).

3-(4-ethynyl-3-methoxyphenoxy)pyridine was prepared as for 4-(pyridine-3-yloxy)ethynylbenzene, using 4-(pyridine-3-yloxy)-2-methoxybenzaldehyde.

MS calculated 226.1 ($MH^+$), exp 226.0 ($MH^+$).

3-(4-ethynyl-2-fluorophenoxy)pyridine was prepared analogously to 3-(4-ethynyl-3-methoxyphenoxy)pyridine MS calculated 214.1 ($MH^+$), exp 214.0 ($MH^+$).

4-(pyridine-4-ylmethoxy)ethynylbenzene

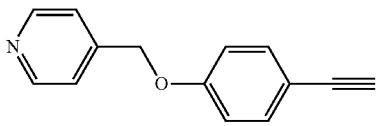 [SMILES: C#Cc1ccc(OCc2ccncc2)cc1]

Prepared as for 4-(pyridine-3-yloxy)ethynylbenzene, using 4-(pyridine-4-ylmethoxy)benzaldehyde.

$^1$H NMR (600 MHz, CDCl3) δ 8.55 (s, 4H), 7.50-7.32 (m, 4H), 1.55 (s, 2H).

MS calculated 210.1 ($MH^+$), exp 210.0 ($MH^+$).

4-(pyridine-4-ylmethoxy)ethynylbenzene

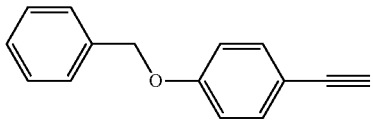

Prepared as for 4-(pyridine-3-yloxy)ethynylbenzene, using 4-benzyloxybenzaldehyde.

MS calculated 209.1 ($MH^+$), exp 209.0 ($MH^+$).

7-ethynyl-4H-imidazo[2,1-c][1,4]benzoxazine

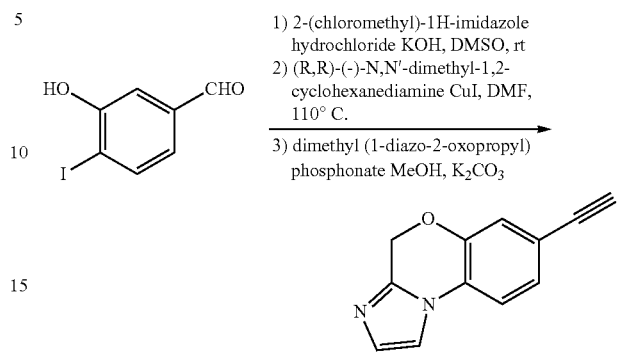

3-(1H-imidazol-2-ylmethoxy)-4-iodobenzaldehyde

To a flask, were added 3-hydroxy-4-iodobenzaldehyde (200 mg, 0.806 mmol), KOH (43.0 mg, 0.766 mmol) and DMSO (2 ml). The mixture was stirred at rt for 2 h. 2-(chloromethyl)-1H-imidazole hydrochloride (105.4 mg, 0.689 mmol) in 1 ml of DMSO was added to this mixture and stirred overnight. The mixture was diluted with DCM and water. The organic phase was washed with brine, dried over sodium sulfate and concentrated to afford crude product, which was purified on silica gel (MeOH/DCM=8/92) to afford desire product (97.4 mg, 0.297 mmol, 36.8% yield).

4H-imidazo[2,1-c][1,4]benzoxazine-7-carbaldehyde

To a vial, were added copper(I) iodide (27.8 mg, 0.146 mmol), 3-(1H-imidazol-2-ylmethoxy)-4-iodobenzaldehyde (127.7 mg, 0.389 mmol), cesium carbonate (267 mg, 0.819 mmol) and a stir bar. The reaction vial was purged with Argon 3 times. The (R,R)-(−)-N,N'-dimethyl-1,2-cyclohexanediamine (50 mg, 0.352 mmol) and DMF (2 ml) were added. The mixture was heated at 110° C. for 1 h. LCMS showed product formation. The mixture was filtered and purified on reverse phase HPLC to afford desired product (24.8 mg, 0.124 mmol, 31.8% yield).

7-ethynyl-4H-imidazo[2,1-c][1,4]benzoxazine

4H-Imidazo[2,1-c][1,4]benzoxazine-7-carbaldehyde (44 mg, 0.140 mmol) and anhydrous potassium carbonate (120 mg, 0.868 mmol) were placed in a 25-ml flask and placed on high vacuum for 10 min. Under $N_2$, anhydrous MeOH (5 ml) was added. To the suspension was added dimethyl (1-diazo-2-oxopropyl) phosphonate (0.03 ml, 0.192 mmol). The reaction was stirred at rt for 2 h. The mixture was diluted with DCM, washed with water, dried over sodium sulfate, concentrated to afford desired product (11.9 mg, 0.061 mmol, 43.3% yield).

$^1$H NMR (500 MHz, $CDCl_3$) δ 7.35 (d, J=1.0 Hz 1H), 7.16-7.28 (m, 4H), 5.28 (s, 2H), 3.10 (s, 1H).

MS cal'd 197.1 ($MH^+$), exp 197.0 ($MH^+$).

5-ethynyl-2-(4-methyl-1H-imidazol-1-yl)-1,3-thiazole

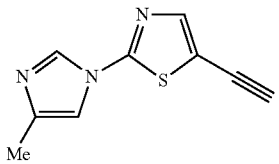

A mixture of 2-bromo-1,3-thiazole-5-carbaldehyde (10 mg, 0.068 mmol), 4-methyl-1H-imidazole (7.23 mg, 0.088 mmol), potassium carbonate (28.1 mg, 0.203 mmol) and DMF (5 ml) were heated at 110° C. for 1 h. The mixture was purified on silica gel (EtOAc/hexane 8:2) to afford 2-(4-methyl-1H-imidazol-1-yl)-1,3-thiazole-5-carbaldehyde (38.4 mg, 0.199 mmol) as a yellow solid. This aldehyde (38.4 mg, 0.199 mmol) and anhydrous potassium carbonate (110 mg, 0.795 mmol) were placed in a 25-ml flask and placed on high vacuum for 10 min. Under N2, anhydrous MeOH (2 ml) was added. To the suspension was added dimethyl (1-diazo-2-oxopropyl) phosphonate (40 µl, 0.256 mmol). The reaction was stirred at rt for 22 h. The mixture was diluted with DCM, washed with water, dried over sodium sulfate, concentrated to afford crude product, which was used in next step directly.

MS cal'd 190.0 (MH$^+$), exp 190.0 (MH$^+$).

4-(5-ethynyl-2-thienyl)-1-methyl-1H-pyrazole

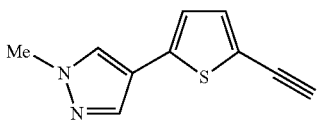

5-Bromothiophene-2-carbaldehyde (86.6 mg, 0.453 mmol) was added to a 20-ml microwave vial along with 4-(4,4,5,5-tetramethyl-1,3,2-dioxaborolan-2-yl)-1H-pyrazole (185.6 mg, 0.892 mmol), sodium carbonate (0.42 ml, 0.840 mmol, 2M), PdCl2(dppf) (68.3 mg, 0.093 mmol), dioxane (7.00 ml) and Water (2 ml). The vial was sealed and microwaved at 100° C. for 10 minutes. The reaction mixture was filtered, diluted with EtOAc and water. The organic phase was washed with brine, dried and concentrated to afford crude product, which was purified on silica gel (EtOAc/hexane-8/2) to afford 5-(1H-pyrazol-4-yl)thiophene-2-carbaldehyde (66.8 mg, 0.347 mmol, 77% yield) as a yellow-green solid. This aldehyde (66.8 mg, 0.347 mmol) and anhydrous potassium carbonate (197 mg, 1.425 mmol) were placed in a 25-ml flask and placed on high vacuum for 10 min. Under N2, anhydrous MeOH (2 ml) was added. To the suspension was added dimethyl (1-diazo-2-oxopropyl) phosphonate (0.065 ml, 0.417 mmol). The reaction was stirred at rt for 4 h. The mixture was diluted with DCM, washed with water, dried over sodium sulfate, concentrated to afford crude product (74.3 mg, 0.395 mmol, 114% yield), which was used in next step directly.

MS calcd 189.0 (MH$^+$), exp 189.1 (MH$^+$).

Other alkynes were prepared in similar fashion from the appropriate aldehydes or aryl bromides via the routes described above.

Syntheses of Other Intermediates

6-fluoro-3-[4-(piperidin-4-yl)-1H-1,2,3-triazol-1-yl]-1-(2,2,2-trifluoroethyl)-1,3,4,5-tetrahydro-2H-1-benzazepin-2-one

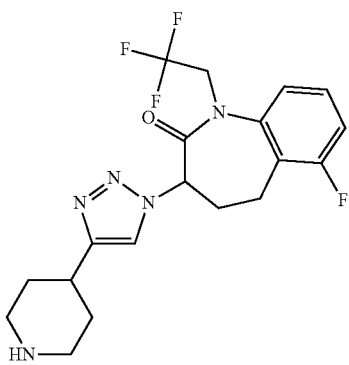 [SMILES: O=C1C(n2cc(C3CCNCC3)nn2)CCc2c(F)cccc2N1CC(F)(F)F]

tert-Butyl 4-{1-[6-fluoro-2-oxo-1-(2,2,2-trifluoroethyl)-2,3,4,5-tetrahydro-1H-1-benzazepin-3-yl]-1H-1,2,3-triazol-4-yl}piperidine-1-carboxylate was prepared from tert-butyl 4-ethynylpiperidine-1-carboxylate (synthesized from tert-butyl 4-formylpiperidine-1-carboxylate and Bestmann's reagent under standard condition) and 3-azido-6-fluoro-1-(2,2,2-trifluoroethyl)-1,3,4,5-tetrahydro-2H-1-benzazepin-2-one under standard click chemistry condition. MS calculated 512.2 (MH$^+$), exp 521.1 (MH$^+$).

To tert-butyl 4-{1-[6-fluoro-2-oxo-1-(2,2,2-trifluoroethyl)-2,3,4,5-tetrahydro-1H-1-benzazepin-3-yl]-1H-1,2,3-triazol-4-yl}piperidine-1-carboxylate (680 mg, 1.3 mmol) in DCM (10 mL) was added TFA (1 mL, 13.3 mmol) and the mixture was stirred for 4 h.

To the mixture was added water and extracted with 3:1 EtOAc/Et$_3$N. The organic layer was washed with water. The combined organic layer was dried, filtered and solvent removed under reduced pressure to afford 500 mg title compound.

MS calculated 412.2 (MH$^+$), exp 421.1 (MH$^+$).

6-fluoro-3-[4-(2-fluoropyridin-4-yl)-1H-1,2,3-triazol-1-yl]-1-(2,22-trifluoroethyl)-1,3,4,5-tetrahydro-2H-1-benzazepin-2-one

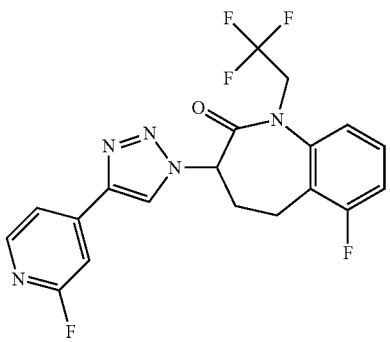 [SMILES: O=C1C(n2cc(-c3ccnc(F)c3)nn2)CCc2c(F)cccc2N1CC(F)(F)F]

The title compound was prepared from 4-ethynyl-2-fluoropyridine (prepared from 2-fluoro-4-iodopyridine through Sonogashira coupling with TMS acetylene and deprotection of TMS with $K_2CO_3$) and 3-azido-6-fluoro-1-(2,2,2-trifluoroethyl)-1,3,4,5-tetrahydro-2H-1-benzazepin-2-one under standard click chemistry condition.

MS calculated 424.1 ($MH^+$), exp 424.0 ($MH^+$).

6-fluoro-3-[4-(2-oxo-1,2-dihydropyridin-4-yl)-1H-1,2,3-triazol-1-yl]-1-(2,2,2-trifluoroethyl)-1,3,4,5-tetrahydro-2H-1-benzazepin-2-one

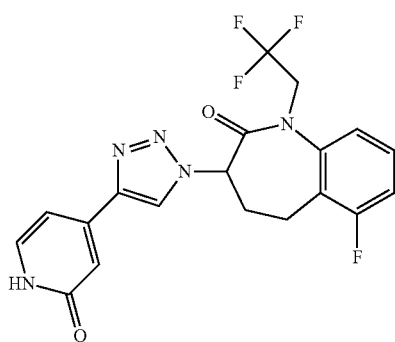 [SMILES: O=C1C(n2cc(-c3cc[nH]c(=O)c3)nn2)CCc2c(F)cccc2N1CC(F)(F)F]

In a sealed tube, 6-fluoro-3-[4-(2-fluoropyridin-4-yl)-1H-1,2,3-triazol-1-yl]-1-(2,2,2-trifluoroethyl)-1,3,4,5-tetrahydro-2H-1-benzazepin-2-one (100 mg, 0.236 mmol) in 1.2 mL of 5:1 $AcOH/H_2O$ was heated at 120° C. overnight. After cooled to ambient temperature and solvent reduced under reduced pressure, the residue was purified by column chromatography on silica gel (0-20% MeOH in EtOAc) to afford 98 mg title compound.

MS calculated 422.1 ($MH^+$), exp 422.0 ($MH^+$).

3-[4-(4-bromophenyl)-1H-1,2,3-triazol-1-yl]-6-fluoro-1-(2,2,2-trifluoroethyl)-1,3,4,5-tetrahydro-2H-1-benzazepin-2-one

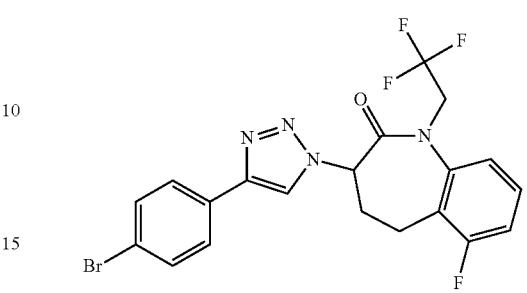

1-Bromo-4-ethynylbenzene (271 mg, 1.499 mmol), cupric sulfate (65.2 mg, 0.409 mmol), sodium ascorbate (108 mg, 0.545 mmol), and 3-azido-6-fluoro-1-(2,2,2-trifluoroethyl)-1,3,4,5-tetrahydro-2H-1-benzazepin-2-one (300 mg, 1.362 mmol) in 6.6 mL of a 1:1:1 solution of $DMF:EtOH:H_2O$ was stirred for 25 mins. The mixture was diluted with water before EtOAc was added to extract the product. The organic phase was separated and washed with water (2×) and brine (1×) before being dried with $Na_2SO_4$ and evaporated to afford an oil. This material was chromatographed on silica (0-80% EtOAc in hexanes) to yield 3-[4-(4-bromophenyl)-1H-1,2,3-triazol-1-yl]-6-fluoro-1-(2,2,2-trifluoroethyl)-1,3,4,5-tetrahydro-2H-1-benzazepin-2-one (495.1 mg) as a solid.

Synthesis of 6-Fluoro-3-[4-(4-iodo-3-methoxy-phenyl)-1,2,3-triazol-1-yl]-1-(2,2,2-trifluoro-ethyl)-1,3,4,5-tetrahydro-1-benzazepin-2-one

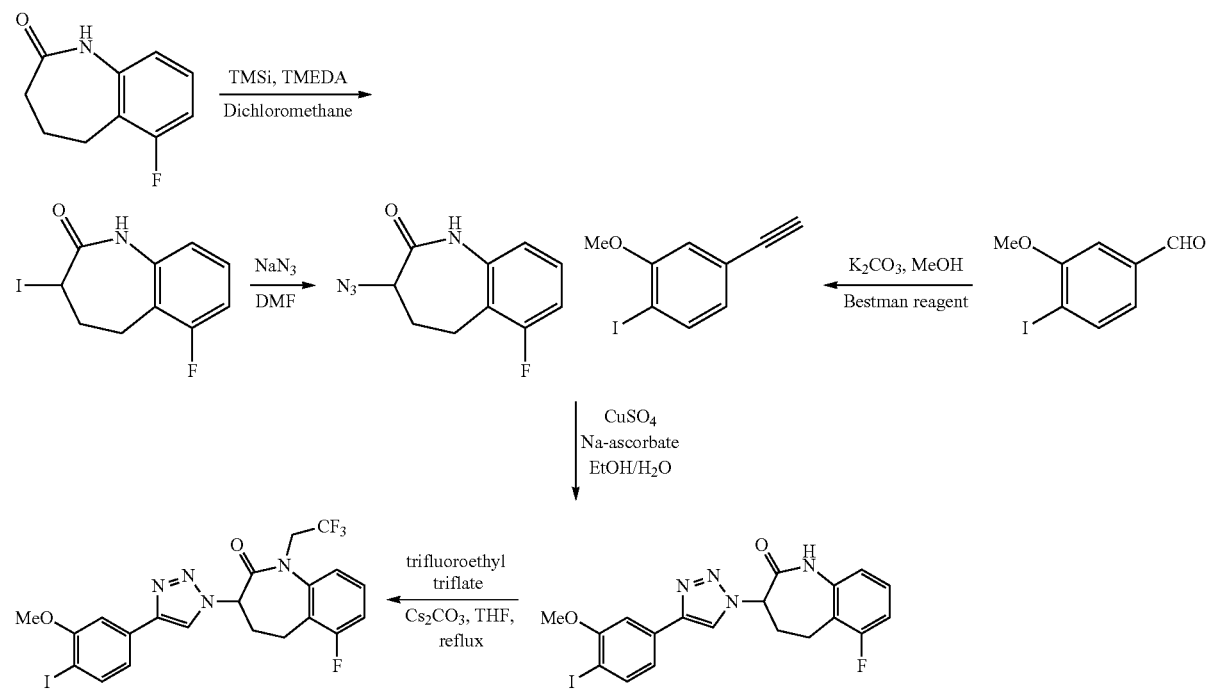

6-Fluoro-1,3,4,5-tetrahydro-1-benzazepin-2-one (25 g, 140 mmol) was charged to a 100-mL three neck flask with a dropping funnel and an overhead stirrer. DCM (250 ml) is added and the reaction is cooled to 0° C. TMEDA (29.5 ml, 195 mmol) is added, followed by drop wise addition of iodotrimethylsilane (26.6 ml, 195 mmol). The mixture was stirred for 45 minutes. Iodine (49.6 g, 195 mmol) is added in 5 portions and the mixture is stirred for another 1.5 h. The reaction was quenched with 250 mL $Na_2SO_3$ (aqueous solution). The solids were dissolved in dichloromethane and the layers separated. The organic layer is washed with water, dried over $Na_2SO_4$, and concentrated to give 6-fluoro-3-iodo-1,3,4,5-tetrahydro-1-benzazepin-2-one (42.5 g) as a brown solid.

DMF (300 ml) was added to a mixture of 6-fluoro-3-iodo-1,3,4,5-tetrahydro-1-benzazepin-2-one (42.5 g) and sodium azide (13.59 g, 209 mmol) at room temperature and the reaction was stirred overnight. The mixture was diluted with water (2000 mL) and a precipitate formed, which was filtered off and washed with water. The precipitate was taken up in dichloromethane and washed with brine, dried over $Na_2SO_4$, filtered, and concentrated. The crude 3-Azido-6-fluoro-1,3,4,5-tetrahydro-1-benzazepin-2-one was isolated as a dark brown solid. Residual DMF remains in the sample, which was used without further manipulation in the next reaction.

4-Iodo-3-methoxy-benzaldehyde (27.26 g, 104 mmol) and potassium carbonate (28.8 g, 208 mmol) were placed in a 2000-mL flask under nitrogen and methanol (1317 ml) was added. To the yellowish suspension was added (1-diazo-2-oxo-propyl)-phosphonic acid dimethyl ester (23.98 g, 125 mmol) in 20 mL MeOH via syringe. The reaction mixture was stirred at room temperature for 16 h giving a yellow solution. LCMS showed complete conversion to product. The yellow suspension was concentrated down to approximately 200-300 mL, then aqueous sodium hydrogen carbonate (saturated, 100 mL) was added and the mixture was diluted with diethyl ether (450 mL). The combined organic fractions were washed with brine (saturated, 2×10 mL), dried (MgSO), filtered and the solvent was evaporated under reduced pressure. The residue was dried on high vacuum over night to give a yellow solid. The crude material was purified on silica gel (330 g column; gradient to 30% EtOAc/heptane) and the resulting oil was dried under high vacuum to afford 4-ethynyl-1-iodo-2-methoxy-benzene (22.7 g) a semi-solid yellow material which was pure by NMR.

4-Ethynyl-1-iodo-2-methoxy-benzene (22.23 g, 86 mmol), 3-azido-6-fluoro-1,3,4,5-tetrahydro-1-benzazepin-2-one (20.87 g, 95 mmol), and sodium ascorbate (15.69 g, 86 mmol) were added to EtOH (155 mL) and DMF (155 mL). $CuSO_4 \cdot 5H_2O$ (10.75 g, 43.1 mmol) was added to 20 mL water and added dropwise to the stirring reaction mixture. The reaction stirred for 17 hrs at room temp. Dichloromethane was added and the organic layer was washed with 2N NaOH, dried with sodium sulfate and concentrated. Purification on silica gel (dichloromethane:methanol, 1-15%). 6-Fluoro-3-[4-(4-iodo-3-methoxy-phenyl)-1,2,3-triazol-1-yl]-1,3,4,5-tetrahydro-1-benzazepin-2-one (39.1 g) was obtained as a colorless solid and carried on the next step.

6-Fluoro-3-[4-(4-iodo-3-methoxy-phenyl)-1,2,3-triazol-1-yl]-1,3,4,5-tetrahydro-1-benzazepin-2-one (20 g, 41.8 mmol) was suspended in THF and stirred at room temperature. Cesium carbonate (24.53 g, 75 mmol) was added, followed by 2,2,2-trifluoroethyl trifluoromethanesulfonate (14.56 g, 62.7 mmol). The mixture was heated to gentle reflux for 2 h. The reaction was diluted with water, and the aqueous layer was extracted with EtOAc. The combined organic fractions were dried over $Na_2SO_4$, filtered, and concentrated. The residue was purified on silica gel, gradient to 100% EtOAc/hexanes. 6-Fluoro-3-[4-(4-iodo-3-methoxy-phenyl)-1,2,3-triazol-1-yl]-1-(2,2,2-trifluoro-ethyl)-1,3,4,5-tetrahydro-1-benzazepin-2-one (21.3 g) was obtained as a colorless solid.

3-[4-(4-Iodo-3-methoxy-phenyl)-1,2,3-triazol-1-yl]-1-(2,2,2-trifluoro-ethyl)-1,3,4,5-tetrahydro-1-benzazepin-2-one and 6-fluoro-3-[4-(4-iodo-phenyl)-1,2,3-triazol-1-yl]-1-(2,2,2-trifluoro-ethyl)-1,3,4,5-tetrahydro-1-benzazepin-2-one were prepared in an analogous fashion.

Example 1

3-[4-(3-methoxy-4-pyridin-4-ylphenyl)-1H-1,2,3-triazol-1-yl]-1-(2,2,2-trifluoroethyl)-1,3,4,5-tetrahydro-2H-1-benzazepin-2-one

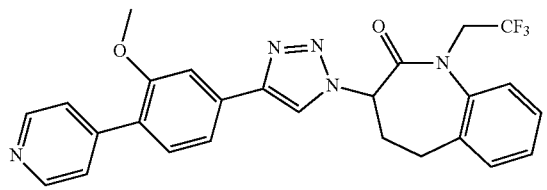 [SMILES: COc1cc(-c2cn(C3CCc4ccccc4N(CC(F)(F)F)C3=O)nn2)ccc1-c1ccncc1]

3-[4-(4-Iodo-3-methoxyphenyl)-1H-1,2,3-triazol-1-yl]-1-(2,2,2-trifluoroethyl)-1,3,4,5-tetrahydro-2H-1-benzazepin-2-one (300 mg, 0.553 mmol) was added to a 20-ml µwave vial along with 4-pyridyl boronic acid (136 mg, 1.106 mmol), $PdCl_2$(dppf) (81 mg, 0.111 mmol), 2M sodium carbonate in water (553 µl, 1.106 mmol), water (1906 µl) and dioxane (8605 µl). The vial was sealed and µwaved at 100° C. for 10 minutes. The reaction mixture was filtered through a plug of Celite. The plug was washed with 100 ml of dioxane and the filtrates were combined and concentrated under reduced pressure. The contents of the flask were reconstituted in 100 ml of water and extracted with ~100 ml of DCM twice. The organic layers were combined, passed through a phase separator cartridge, and concentrated under reduced pressure. The residue was dissolved in 6 ml of DMSO and purified by reverse phase chromatography (20-100 MeCN in water (half was injected with a TFA modifier, the remaining half was purified using a Formic Acid modifier). The pure fractions were pooled and concentrated under reduced pressure. The compound was dissolved in ~300 ml of DCM and washed with $NaHCO_3$ (3×150 ml). The organic layer was passed through a phase separator to remove water and concentrated under reduced pressure to afford 3-[4-(3-methoxy-4-pyridin-4-ylphenyl)-1H-1,2,3-triazol-1-yl]-1-(2,2,2-trifluoroethyl)-1,3,4,5-tetrahydro-2H-1-benzazepin-2-one (246 mg, 0.499 mmol, 90% yield) as an off white solid.

$^1$H NMR (500 MHz, dmso-d6) δ 9.00 (s, 1H), 8.58 (dd, J=4.5, 1.6, 2H), 7.65 (d, J=8.1, 1H), 7.61 (s, 1H), 7.57-7.54 (m, 3H), 7.48 (d, J=7.8, 2H), 7.45 (d, J=7.9, 1H), 7.35 (t, J=7.4, 1H), 5.34 (dd, J=12.0, 7.9, 1H), 5.04 (dq, J=18.8, 9.5, 1H), 4.59 (dq, J=18.1, 9.2, 1H), 3.88 (s, 3H), 3.02-2.92 (m, 2H), 2.87 (td, J=13.1, 7.6, 1H), 2.71-2.59 (m, 1H).

LRMS (APCI) calc'd for ($C_{26}H_{22}F_3N_5O_2$) [M+H]+, 494.2. found 494.2.

Example 2

6-fluoro-3-{4-[5-(pyridin-4-yl)pyrimidin-2-yl]-1H-1,2,3-triazol-1-yl}-1-(2,2,2-trifluoroethyl)-1,3,4,5-tetrahydro-2H-1-benzazepin-2-one

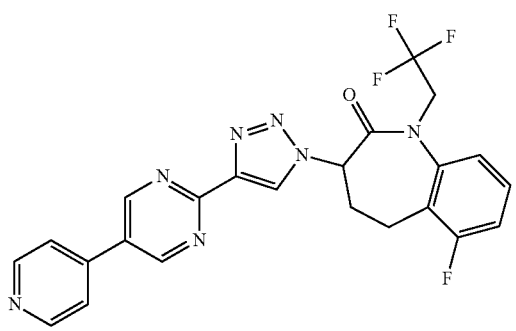 [SMILES: O=C1C(n2cc(-c3ncc(-c4ccncc4)cn3)nn2)CCc2c(F)cccc2N1CC(F)(F)F]

3-[4-(5-Bromopyrimidin-2-yl)-1H-1,2,3-triazol-1-yl]-6-fluoro-1-(2,2,2-trifluoroethyl)-1,3,4,5-tetrahydro-2H-1-benzazepin-2-one (75 mg, 0.155 mmol), 4-pyridineboronic acid (28.5 mg, 0.232 mmol), $Pd_2(dba)_3$ (7.08 mg, 7.73 μmol), cesium carbonate (101 mg, 0.309 mmol), and X-phos (7.37 mg, 0.015 mmol) were combined in a microwave vial along with water (0.5 mL) and 1,4-dioxane (0.9 mL). The vessel was irradiated for 15 mins at 140° C. The vial was allowed to cool before being diluted with EtOAc and syringe filtered. The filtrate was concentrated and purified on column chromotagraphy to yield the desired product, 11 mg.

$^1$H NMR (600 MHz, CDCl3) δ 9.06 (d, J=5.2, 2H), 8.85-8.62 (m, 4H), 7.53 (ddd, J=16.9, 4.4, 1.7, 3H), 7.48-7.30 (m, 1H), 7.11 (dt, J=29.7, 14.7, 2H), 5.65 (dd, J=16.9, 7.6, 1H), 5.10 (dt, J 24.2, 8.8, 2H), 3.45-3.24 (m, 2H), 2.87-2.60 (m, 3H).

MS calculated 484.1 (MH$^+$), exp 484.0 (MH$^+$).

Using methods analogous to those of Examples 1 and 2, the following were prepared:

TABLE I

| Example | Structure | MS (MH$^+$) |
|---|---|---|
| 3 | 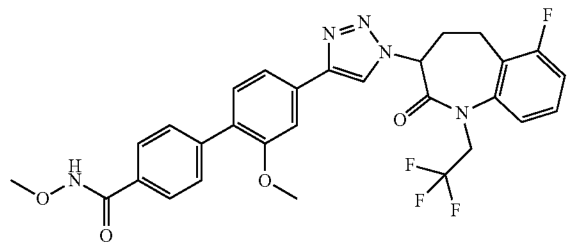 [SMILES: CONC(=O)c1ccc(-c2ccc(-c3cn(C4CCc5c(F)cccc5N(CC(F)(F)F)C4=O)nn3)cc2OC)cc1] | Calc'd 584.2, found 584.1 |
| 4 | 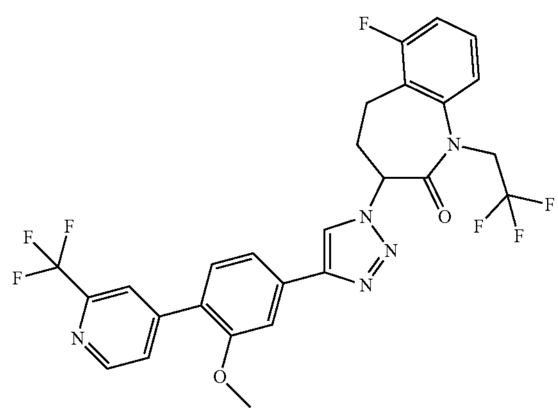 [SMILES: COc1cc(-c2cn(C3CCc4c(F)cccc4N(CC(F)(F)F)C3=O)nn2)ccc1-c1ccnc(C(F)(F)F)c1] | Calc'd 580.2, found 580.1 |
| 5 | 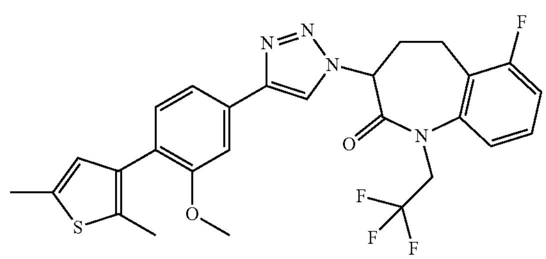 [SMILES: COc1cc(-c2cn(C3CCc4c(F)cccc4N(CC(F)(F)F)C3=O)nn2)ccc1-c1cc(C)sc1C] | Calc'd 545.2, found 545.2 |

TABLE I-continued

| Example | Structure | MS (MH⁺) |
|---|---|---|
| 6 | 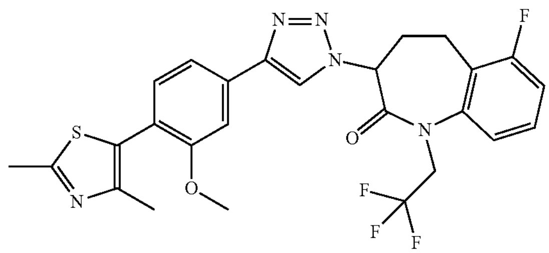 [SMILES: COc1cc(-c2cn(C3CCc4c(F)cccc4N(CC(F)(F)F)C3=O)nn2)ccc1-c1sc(C)nc1C] | Calc'd 546.2, found 546.1 |
| 7 | 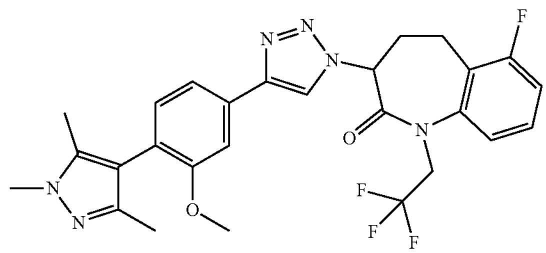 [SMILES: COc1cc(-c2cn(C3CCc4c(F)cccc4N(CC(F)(F)F)C3=O)nn2)ccc1-c1c(C)nn(C)c1C] | Calc'd 543.2, found 543.2 |
| 8 | 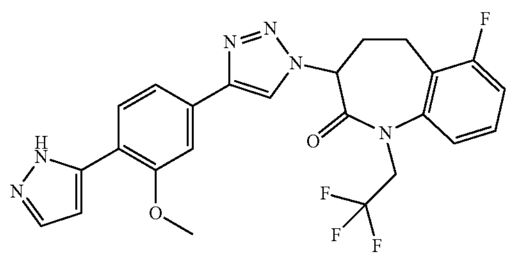 [SMILES: COc1cc(-c2cn(C3CCc4c(F)cccc4N(CC(F)(F)F)C3=O)nn2)ccc1-c1ccn[nH]1] | Calc'd 501.2, found 501.1 |
| 9 | 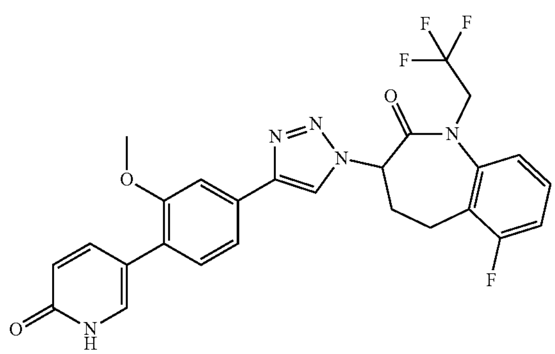 [SMILES: COc1cc(-c2cn(C3CCc4c(F)cccc4N(CC(F)(F)F)C3=O)nn2)ccc1-c1ccc(=O)[nH]c1] | Calc'd 528.2, found 528.1 |
| 10 | 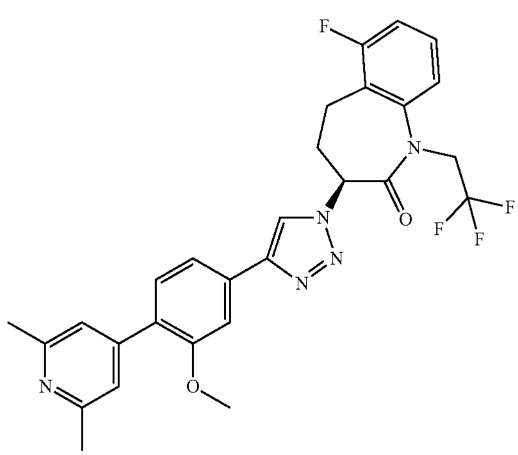 [SMILES: COc1cc(-c2cn([C@H]3CCc4c(F)cccc4N(CC(F)(F)F)C3=O)nn2)ccc1-c1cc(C)nc(C)c1] | Calc'd 540.2, found 540.2 |

TABLE I-continued

| Example | Structure | MS (MH+) |
|---|---|---|
| 11 | 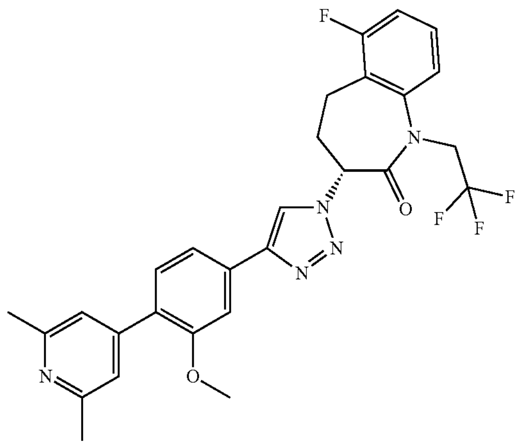 [SMILES: COc1cc(-c2cn([C@@H]3CCc4c(F)cccc4N(CC(F)(F)F)C3=O)nn2)ccc1-c1cc(C)nc(C)c1] | Calc'd 540.2, found 540.2 |
| 12 | 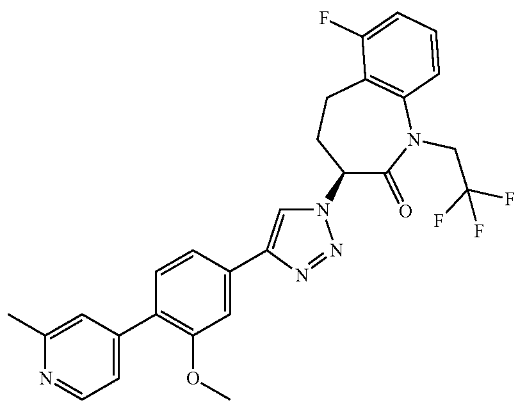 [SMILES: COc1cc(-c2cn([C@H]3CCc4c(F)cccc4N(CC(F)(F)F)C3=O)nn2)ccc1-c1ccnc(C)c1] | Calc'd 526.2, found 526.2 |
| 13 | 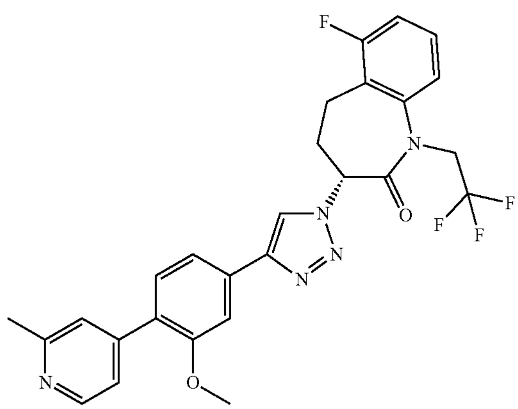 [SMILES: COc1cc(-c2cn([C@@H]3CCc4c(F)cccc4N(CC(F)(F)F)C3=O)nn2)ccc1-c1ccnc(C)c1] | Calc'd 526.2, found 526.2 |
| 14 | 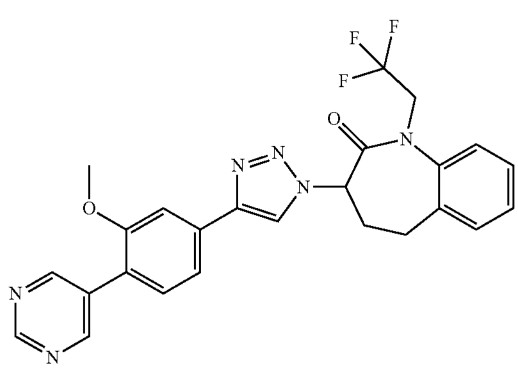 [SMILES: COc1cc(-c2cn(C3CCc4ccccc4N(CC(F)(F)F)C3=O)nn2)ccc1-c1cncnc1] | Calc'd 495.2, found 495.1 |

TABLE I-continued

| Example | Structure | MS (MH+) |
|---|---|---|
| 15 | 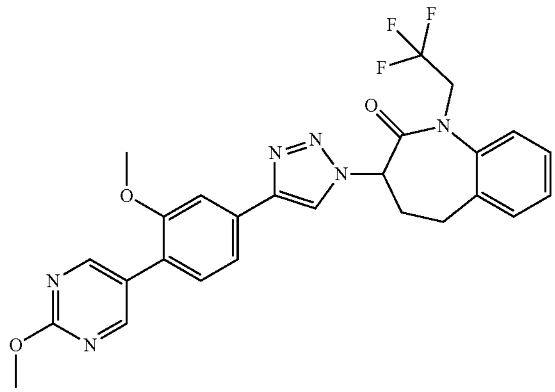 [SMILES: COc1ncc(-c2ccc(-c3cn(C4CCc5ccccc5N(CC(F)(F)F)C4=O)nn3)cc2OC)cn1] | Calc'd 525.2, found 525.2 |
| 16 | 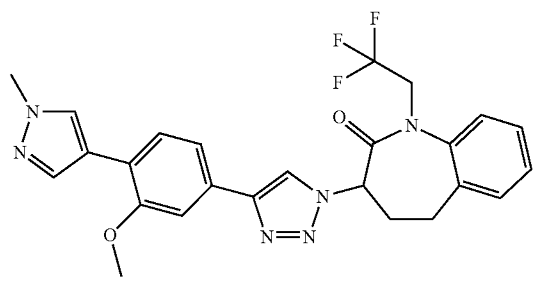 [SMILES: COc1cc(-c2cn(C3CCc4ccccc4N(CC(F)(F)F)C3=O)nn2)ccc1-c1cnn(C)c1] | Calc'd 497.2, found 497.2 |
| 17 | 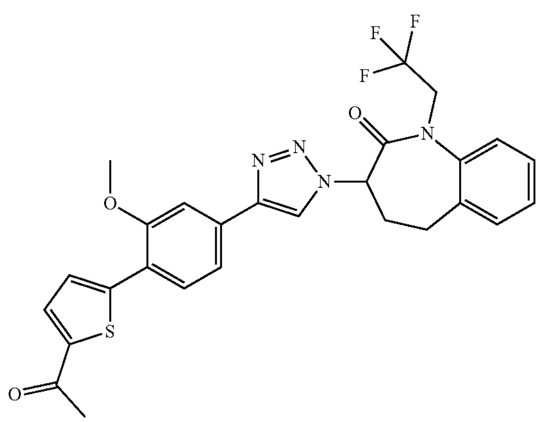 [SMILES: COc1cc(-c2cn(C3CCc4ccccc4N(CC(F)(F)F)C3=O)nn2)ccc1-c1ccc(C(C)=O)s1] | Calc'd 541.2, found 541.1 |
| 18 | 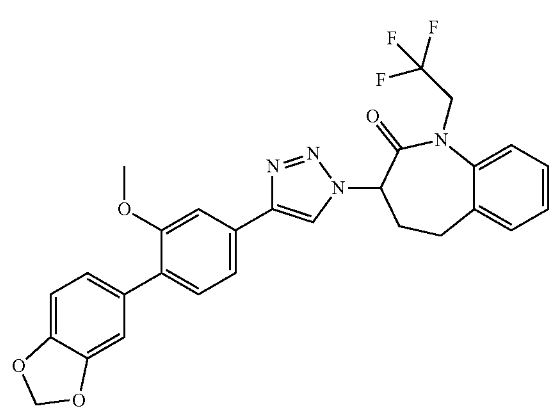 [SMILES: COc1cc(-c2cn(C3CCc4ccccc4N(CC(F)(F)F)C3=O)nn2)ccc1-c1ccc2c(c1)OCO2] | Calc'd 537.2, found 537.2 |

TABLE I-continued

| Example | Structure | MS (MH+) |
|---|---|---|
| 19 | 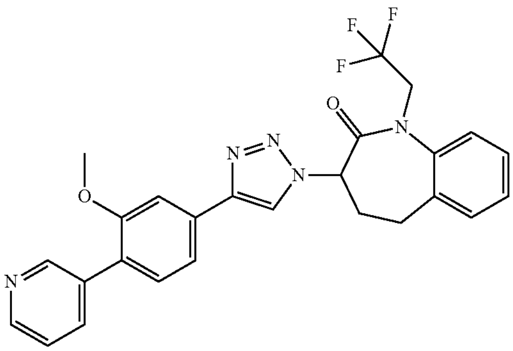 [SMILES: COc1cc(-c2cn(C3CCc4ccccc4N(CC(F)(F)F)C3=O)nn2)ccc1-c1cccnc1] | Calc'd 494.2, found 494.2 |
| 20 | 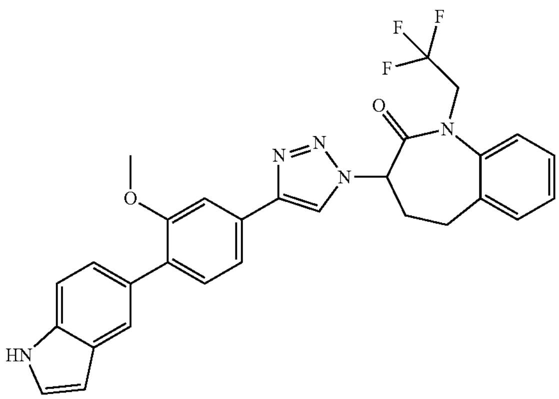 [SMILES: COc1cc(-c2cn(C3CCc4ccccc4N(CC(F)(F)F)C3=O)nn2)ccc1-c1ccc2[nH]ccc2c1] | Calc'd 532.2, found 532.2 |
| 21 | 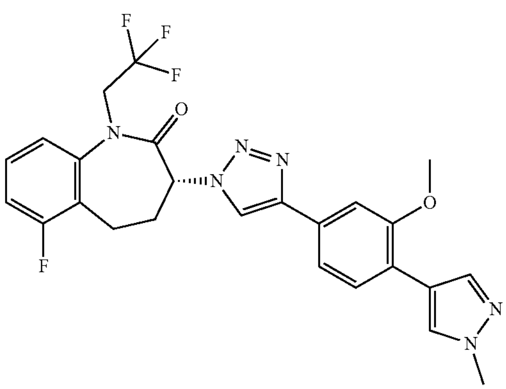 [SMILES: COc1cc(-c2cn([C@@H]3CCc4c(F)cccc4N(CC(F)(F)F)C3=O)nn2)ccc1-c1cnn(C)c1] | Calc'd 515.2, found 515.1 |
| 22 | 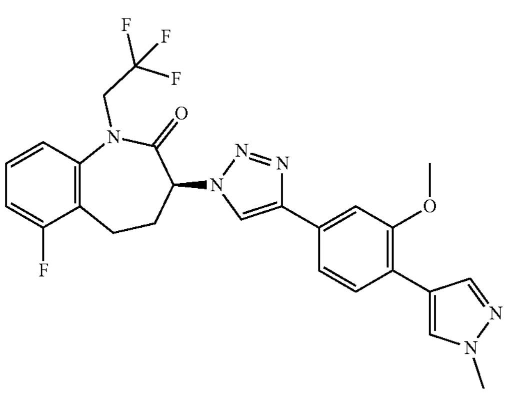 [SMILES: COc1cc(-c2cn([C@H]3CCc4c(F)cccc4N(CC(F)(F)F)C3=O)nn2)ccc1-c1cnn(C)c1] | Calc'd 515.2, found 515.2 |

TABLE I-continued
| Example | Structure | MS (MH+) |
|---|---|---|
| 23 | 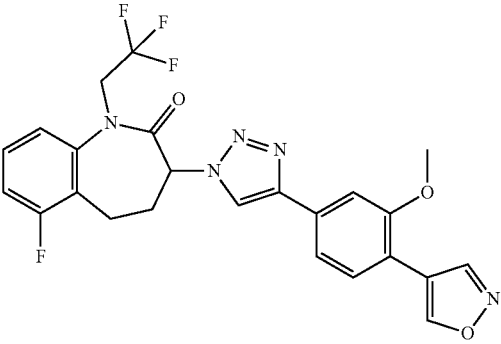 [SMILES: COc1cc(-c2cn(C3CCc4c(F)cccc4N(CC(F)(F)F)C3=O)nn2)ccc1-c1cnoc1] | Calc'd 502.2, found 502.1 |
| 24 | 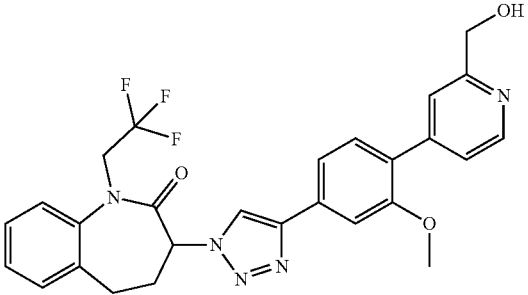 [SMILES: COc1cc(-c2cn(C3CCc4ccccc4N(CC(F)(F)F)C3=O)nn2)ccc1-c1ccnc(CO)c1] | Calc'd 524.2, found 525 |
| 25 | 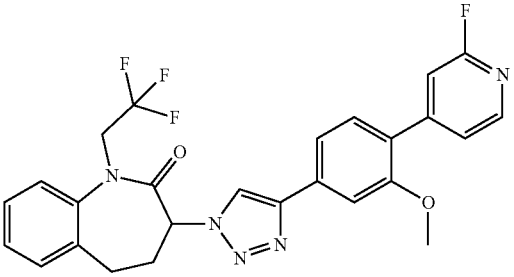 [SMILES: COc1cc(-c2cn(C3CCc4ccccc4N(CC(F)(F)F)C3=O)nn2)ccc1-c1ccnc(F)c1] | Calc'd 512.2, found 513 |
| 26 | 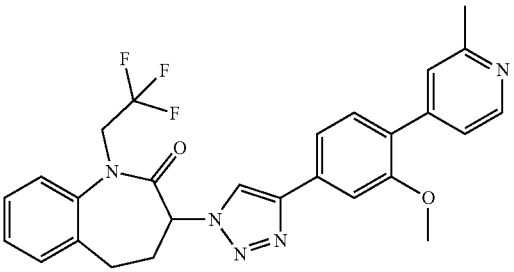 [SMILES: COc1cc(-c2cn(C3CCc4ccccc4N(CC(F)(F)F)C3=O)nn2)ccc1-c1ccnc(C)c1] | Calc'd 508.2, found 509 |
| 27 | 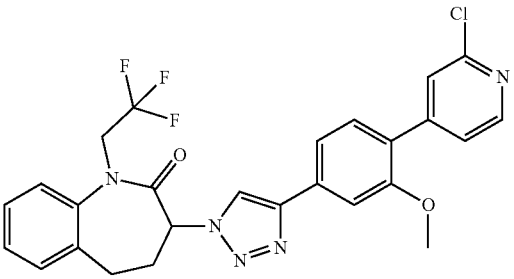 [SMILES: COc1cc(-c2cn(C3CCc4ccccc4N(CC(F)(F)F)C3=O)nn2)ccc1-c1ccnc(Cl)c1] | Calc'd 528.1, found 529 |

TABLE I-continued

| Example | Structure | MS (MH+) |
|---------|-----------|----------|
| 28 | 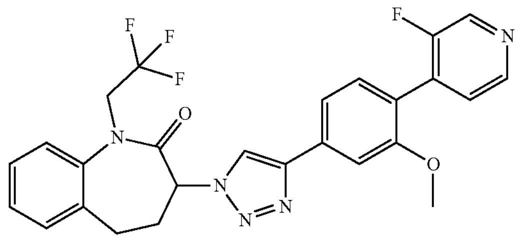 [SMILES: COc1cc(-c2cn(C3CCc4ccccc4N(CC(F)(F)F)C3=O)nn2)ccc1-c1ccncc1F] | Calc'd 512.2, found 513 |
| 29 | 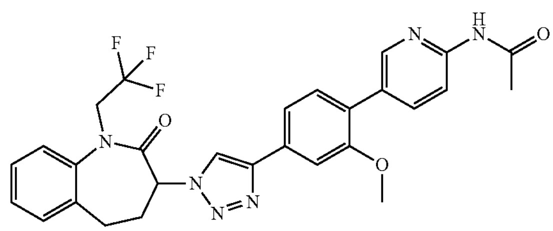 [SMILES: COc1cc(-c2cn(C3CCc4ccccc4N(CC(F)(F)F)C3=O)nn2)ccc1-c1ccc(NC(C)=O)nc1] | Calc'd 551.2, found 552 |
| 30 | 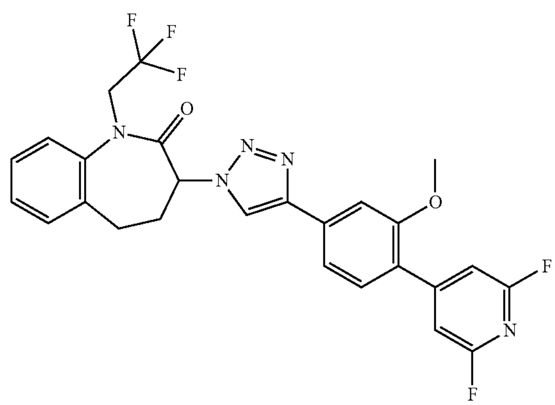 [SMILES: COc1cc(-c2cn(C3CCc4ccccc4N(CC(F)(F)F)C3=O)nn2)ccc1-c1cc(F)nc(F)c1] | Calc'd 530.2, found 531 |
| 31 | 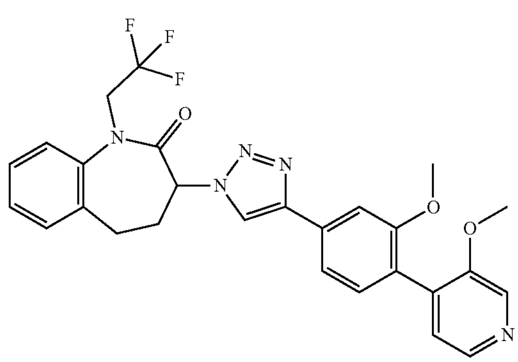 [SMILES: COc1cnccc1-c1ccc(-c2cn(C3CCc4ccccc4N(CC(F)(F)F)C3=O)nn2)cc1OC] | Calc'd 524.2, found 525 |

TABLE I-continued

| Example | Structure | MS (MH+) |
|---------|-----------|----------|
| 32 | 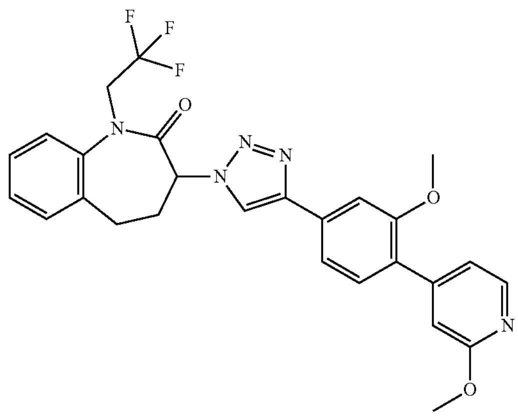 [SMILES: COc1cc(-c2ccc(-c3cn(C4CCc5ccccc5N(CC(F)(F)F)C4=O)nn3)cc2OC)ccn1] | Calc'd 524.2, found 525 |
| 33 | 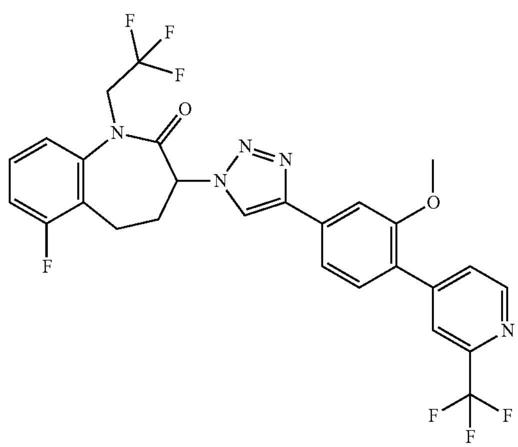 [SMILES: COc1cc(-c2cn(C3CCc4c(F)cccc4N(CC(F)(F)F)C3=O)nn2)ccc1-c1ccnc(C(F)(F)F)c1] | Calc'd 580.2, found 581 |
| 34 | 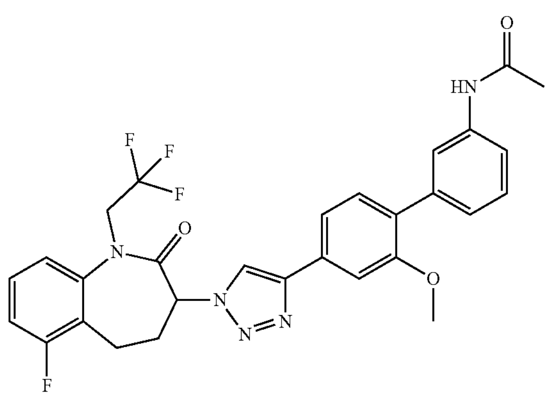 [SMILES: COc1cc(-c2cn(C3CCc4c(F)cccc4N(CC(F)(F)F)C3=O)nn2)ccc1-c1cccc(NC(C)=O)c1] | Calc'd 568.2, found 569 |
| 35 | 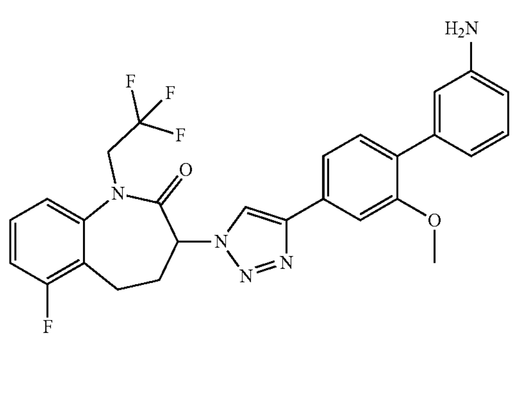 [SMILES: COc1cc(-c2cn(C3CCc4c(F)cccc4N(CC(F)(F)F)C3=O)nn2)ccc1-c1cccc(N)c1] | Calc'd 526.2, found 527 |

TABLE I-continued
| Example | Structure | MS (MH+) |
|---|---|---|
| 36 | 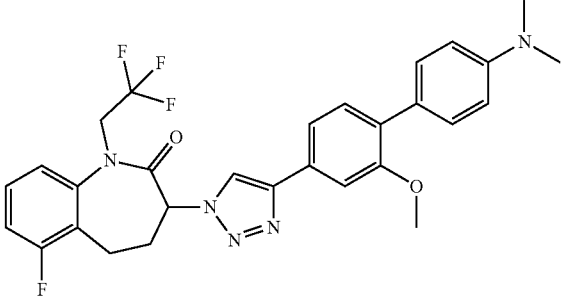 [SMILES: COc1cc(-c2cn(C3CCc4c(F)cccc4N(CC(F)(F)F)C3=O)nn2)ccc1-c1ccc(N(C)C)cc1] | Calc'd 554.2, found 555 |
| 37 | 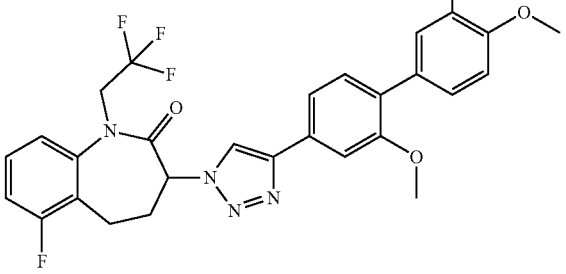 | Calc'd 555.2, found 556 |
| 38 | 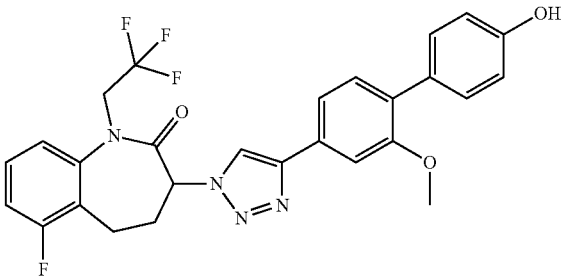 [SMILES: COc1cc(-c2cn(C3CCc4c(F)cccc4N(CC(F)(F)F)C3=O)nn2)ccc1-c1ccc(O)cc1] | Calc'd 527.2, found 528 |
| 39 | 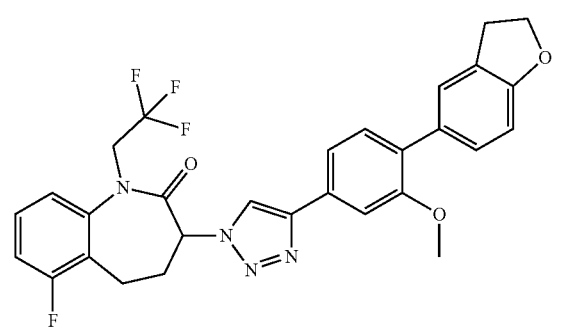 [SMILES: COc1cc(-c2cn(C3CCc4c(F)cccc4N(CC(F)(F)F)C3=O)nn2)ccc1-c1ccc2c(c1)CCO2] | Calc'd 553.2, found 554 |
| 40 | 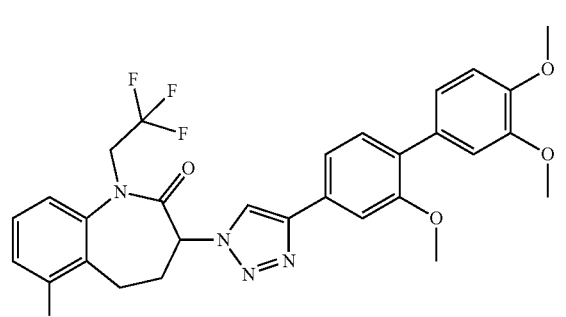 | Calc'd 571.2, found 572 |

TABLE I-continued

| Example | Structure | MS (MH⁺) |
|---|---|---|
| 41 | 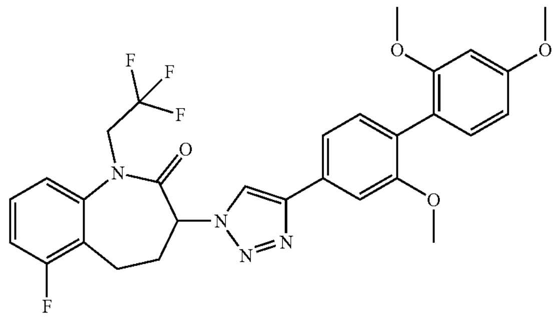 [SMILES: COc1ccc(-c2ccc(-c3cn(C4CCc5c(F)cccc5N(CC(F)(F)F)C4=O)nn3)cc2OC)c(OC)c1] | Calc'd 571.2, found 572 |
| 42 | 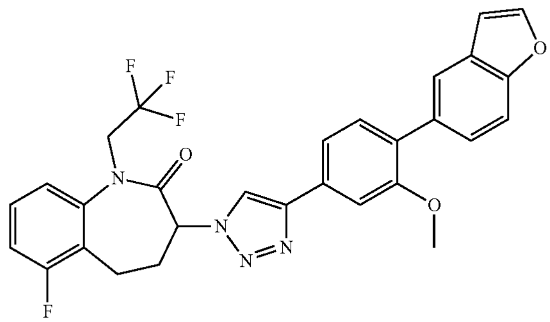 [SMILES: COc1cc(-c2cn(C3CCc4c(F)cccc4N(CC(F)(F)F)C3=O)nn2)ccc1-c1ccc2occc2c1] | Calc'd 551.2, found 552 |
| 43 | 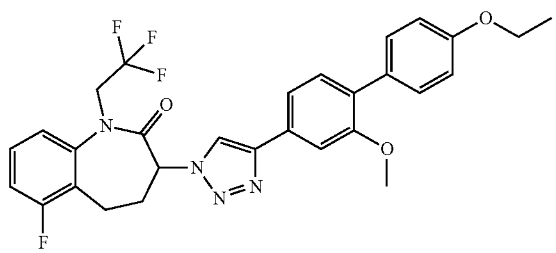 [SMILES: CCOc1ccc(-c2ccc(-c3cn(C4CCc5c(F)cccc5N(CC(F)(F)F)C4=O)nn3)cc2OC)cc1] | Calc'd 555.2, found 556 |
| 44 | 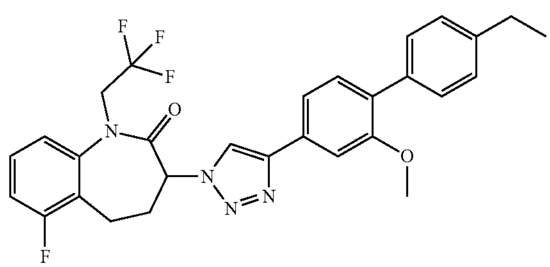 [SMILES: CCc1ccc(-c2ccc(-c3cn(C4CCc5c(F)cccc5N(CC(F)(F)F)C4=O)nn3)cc2OC)cc1] | Calc'd 539.2, found 540 |
| 45 | 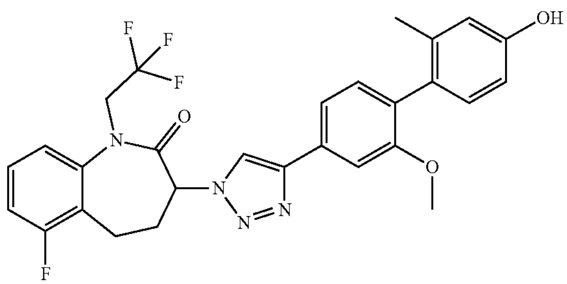 [SMILES: COc1cc(-c2cn(C3CCc4c(F)cccc4N(CC(F)(F)F)C3=O)nn2)ccc1-c1ccc(O)cc1C] | Calc'd 541.2, found 542 |

TABLE I-continued

| Example | Structure | MS (MH+) |
|---|---|---|
| 46 | 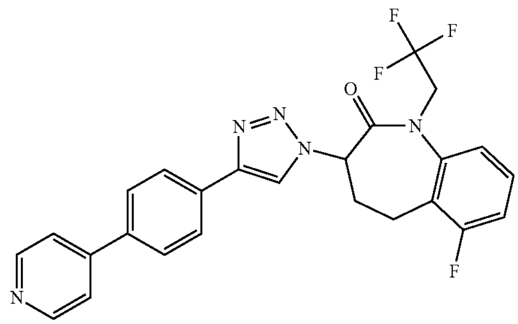 [SMILES: O=C1C(n2cc(-c3ccc(-c4ccncc4)cc3)nn2)CCc2c(F)cccc2N1CC(F)(F)F] | Calc'd: 482.2, found: 482.1 |
| 47 | 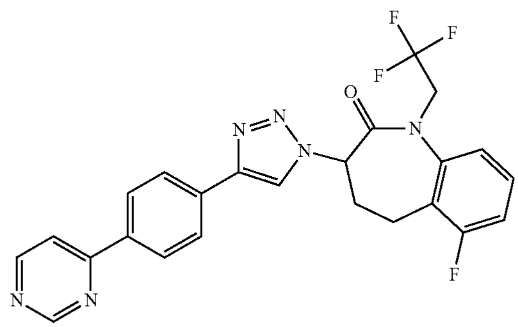 | Calc'd: 483.2, found: 483.1 |
| 48 | 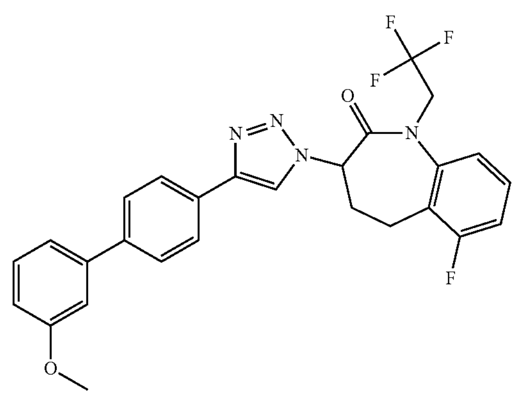 [SMILES: COc1cccc(-c2ccc(-c3cn(C4CCc5c(F)cccc5N(CC(F)(F)F)C4=O)nn3)cc2)c1] | Calc'd 511.2, found 511.1 |
| 49 | 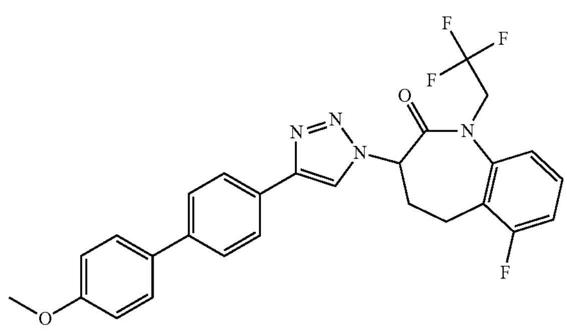 [SMILES: COc1ccc(-c2ccc(-c3cn(C4CCc5c(F)cccc5N(CC(F)(F)F)C4=O)nn3)cc2)cc1] | Calc'd 511.2, found 511.1 |

TABLE I-continued

| Example | Structure | MS (MH+) |
|---|---|---|
| 50 | 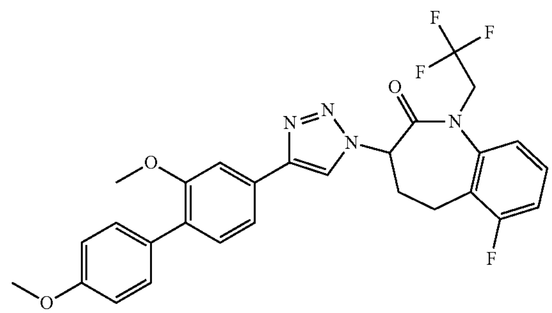 [SMILES: COc1ccc(-c2ccc(-c3cn(C4CCc5c(F)cccc5N(CC(F)(F)F)C4=O)nn3)cc2OC)cc1] | Calc'd 541.2, found 541.1 |

Example 51

4-(1-(6-fluoro-2-oxo-1-(2,2,2-trifluoroethyl)-2,3,4,5-tetrahydro-1H-1-benzazepin-3-yl)-1H-1,2,3-triazol-4-yl)-2-methoxy-N-4-pyrimidinylbenzamide formic acid salt

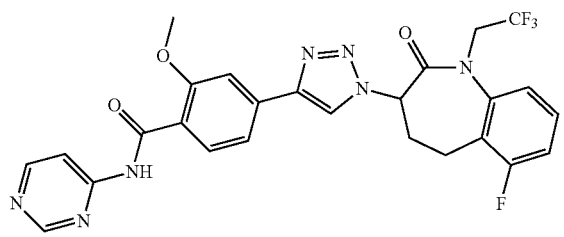 [SMILES: COc1cc(-c2cn(C3CCc4c(F)cccc4N(CC(F)(F)F)C3=O)nn2)ccc1C(=O)Nc1ccncn1]

6-Fluoro-3-(4-(4-iodo-3-methoxyphenyl)-1H-1,2,3-triazol-1-yl]-1-(2,2,2-trifluoroethyl)-1,3,4,5-tetrahydro-2H-1-benzazepin-2-one (20 mg, 0.036 mmol), 4-aminopyrimidine (8.5 mg, 0.089 mmol), DBU (53.8 μl, 0.357 mmol), Mo(CO)$_6$, P(tBu)$_3$HBF$_4$ salt (2.59 mg, 8.92 μmol) and Hermann's Palladacycle (4.18 mg, 4.46 μmol) combined in dioxane (0.595 ml) in a microwave vial. The vial was sealed and microwaved at 140° C. for 12 minutes. The reaction mixture was dried in vacuo. Analytically pure material was obtained by purification by preparative HPLC Reverse phase (C-18), eluting with acetonitrile/water 0.05% formic acid. Lyophilizing afforded the formic acid salt of 4-(1-(6-fluoro-2-oxo-1-(2,2,2-trifluoroethyl)-2,3,4,5-tetrahydro-1H-1-benzazepin-3-yl)-1H-1,2,3-thiazol-4-yl)-2-methoxy-N-4-pyrimidinylbenzamide (3.6 mg, 0.0065 mmol, 18% yield) as a pale pink, fluffy solid.

$^1$H NMR (600 MHz, DMSO) δ 10.70 (s, 1H), 8.99 (s, 1H), 8.88 (s, 1H), 8.69 (d, J=6.0, 1H), 8.19 (d, J=5.8, 1H), 7.90 (d, J=8.1, 1H), 7.64 (s, 1H), 7.58 (d, J=8.2, 1H), 7.49 (s, 2H), 7.25 (s, 1H), 5.47-5.42 (m, 1H), 5.01 (s, 1H), 4.55 (s, 1H), 4.03 (s, 3H), 3.24 (s, 1H), 2.96 (d, J=7.1, 1H), 2.75-2.47 (m, 2H).

LRMS (APCI) calc'd for (C$_{26}$H$_{21}$F$_4$N$_7$O$_3$) [M+H]$^+$, 556.1. found 555.1.

The following were prepared by the same method, using the appropriate amine in place of 4-aminopyrimidine:

TABLE II

| Example | Structure | MS (MH+) |
|---|---|---|
| 52 | 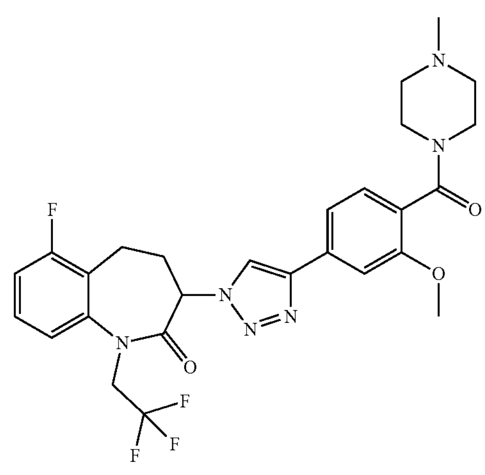 [SMILES: COc1cc(-c2cn(C3CCc4c(F)cccc4N(CC(F)(F)F)C3=O)nn2)ccc1C(=O)N1CCN(C)CC1] | Calc'd 561.2, found 561.0 |

TABLE II-continued

| Example | Structure | MS (MH+) |
|---|---|---|
| 53 | 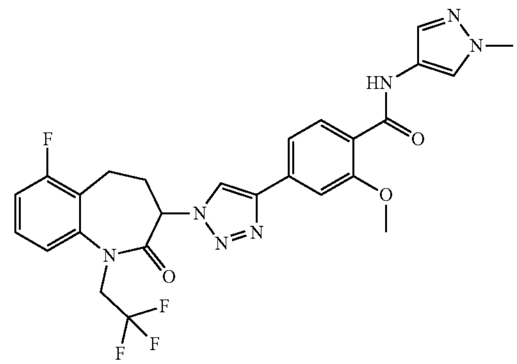 [SMILES: COc1cc(-c2cn(C3CCc4c(F)cccc4N(CC(F)(F)F)C3=O)nn2)ccc1C(=O)Nc1cnn(C)c1] | Calc'd 558.2, found 558.0 |
| 54 | 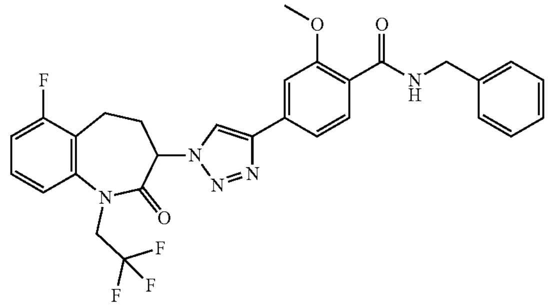 [SMILES: COc1cc(-c2cn(C3CCc4c(F)cccc4N(CC(F)(F)F)C3=O)nn2)ccc1C(=O)NCc1ccccc1] | Calc'd 568.2, found 568.0 |

Example 55

6-fluoro-3-{4-[2-fluoro-4-(pyridin-4-yl)-phenyl]-1H-1,2,3-triazol-1-yl}-1-(2,2,2-trifluoroethyl)-1,3,4,5-tetrahydro-2H-1-benzazepin-2-one

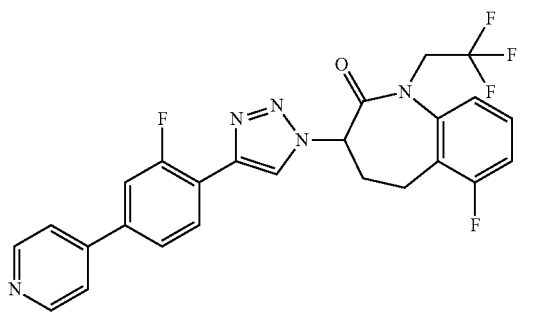 [SMILES: O=C1C(n2cc(-c3ccc(-c4ccncc4)cc3F)nn2)CCc2c(F)cccc2N1CC(F)(F)F]

Following GP 3, the title compound (32 mg) was prepared using 4-(4-ethynyl-3-fluorophenyl)pyridine (29 mg) and 3-azido-6-fluoro-1-(2,2,2-trifluoroethyl)-1,3,4,5-tetrahydro-2H-1-benzazepin-2-one (58 mg).

$^1$H NMR (600 MHZ, CDCl$_3$) δ 8.66 (d, J=6 Hz, 2H), 8.37 (m, 2H), 7.54-7.38 (m, 5H), 7.12 (m, 2H), 5.58 (m, 1H), 5.09 (m, 1H), 4.02 (m, 1H), 3.34 (m, 1H), 2.80-2.65 (m, 3H).

MS calculated 500.2 (MH$^+$), exp 500.1 (MH$^+$).

Example 56

6-fluoro-3-{4-[3-fluoro-4-(pyridin-4-yl)phenyl]-1H-1,2,3-triazol-1-yl}-1-(2,2,2-trifluoroethyl)-1,3,4,5-tetrahydro-2H-1-benzazepin-2-one

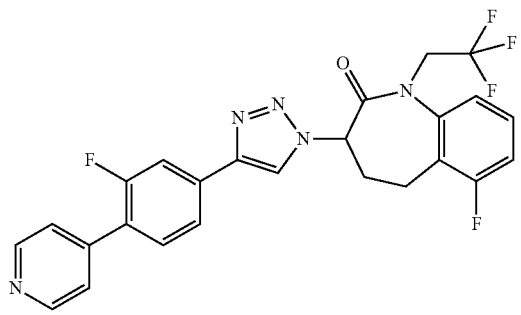 [SMILES: O=C1C(n2cc(-c3ccc(-c4ccncc4)c(F)c3)nn2)CCc2c(F)cccc2N1CC(F)(F)F]

The title compound was prepared by the same route as 6-fluoro-3-{4-[2-fluoro-4-(pyridin-4-yl)phenyl]-1H-1,2,3-triazol-1-yl}-1-(2,2,2-trifluoroethyl)-1,3,4,5-tetrahydro-2H-1-benzazepin-2-one using 4-(4-ethynyl-2-fluorophenyl)pyridine as the alkyne.

$^1$H NMR (600 MHZ, CDCl$_3$) δ 8.66 (broad s, 2H), 8.30 (s, 1H), 7.66 (m, 2H), 7.50 (m, 3H), 7.39 (m, 1H), 7.12 (m, 2H), 5.56 (m, 1H), 5.07 (m, 1H), 4.02 (m, 1H), 3.33 (m, 1H), 2.76-2.65 (m, 3H).

MS calculated 500.2 (MH$^+$), exp 500.1 (MH$^+$)

Example 57

6-fluoro-3-{4-[2-methoxy-4-(3-methyl-1,2,4-oxadiazol-5-yl)phenyl]-1H-1,2,3-triazol-1-yl}-1-(2,2,2-trifluoroethyl)-1,3,4,5-tetrahydro-2H-1-benzazepin-2-one

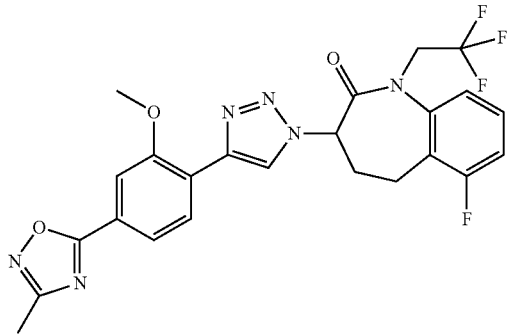 [SMILES: COc1cc(-c2nc(C)no2)ccc1-c1cn(C2CCc3c(F)cccc3N(CC(F)(F)F)C2=O)nn1]

The title compound was prepared by the same route as 6-fluoro-3-{-4-[2-fluoro-4-(pyridin-4-yl)phenyl]-1H-1,2,3-triazol-1-yl}-1-(2,2,2-trifluoroethyl)-1,3,4,5-tetrahydro-2H-1-benzazepin-2-one using 5-(4-ethynyl-3-methoxy-phenyl)-3-methyl-1,2,4-oxadiazole as the alkyne.

$^1$H NMR (600 MHZ, CDCl$_3$) δ 8.50 (s, 1H), 8.45 (d, J=7.8 Hz, 1H), 7.79 (d, J=7.8 Hz, 1H), 7.67 (s, 1H), 7.37 (m, 1H), 7.10 (m, 2H), 5.56 (m, 1H), 5.08 (m, 1H), 4.05 (s, 3H), 4.02 (m, 1H), 3.32 (m, 1H), 2.76 (m, 2H), 2.66 (m, 1H), 2.45 (s, 3H).

MS calculated 517.2 (MH$^+$), exp 517.0 (MH$^+$).

Example 58

6-fluoro-3-{4-[4-(3-methyl-1,2,4-oxadiazol-5-yl)phenyl]-1H-1,2,3-triazol-1-yl}-1-(2,2,2-trifluoroethyl)-1,3,4,5-tetrahydro-2H-1-benzazepin-2-one

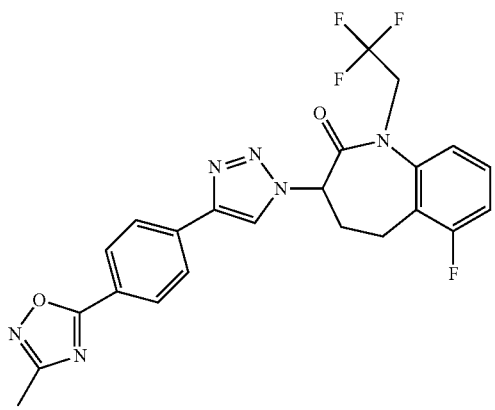 [SMILES: Cc1noc(-c2ccc(-c3cn(C4CCc5c(F)cccc5N(CC(F)(F)F)C4=O)nn3)cc2)n1]

The title compound was prepared by the same route as 6-fluoro-3-{-4-[2-fluoro-4-(pyridin-4-yl)phenyl]-1H-1,2,3-triazol-1-yl}-1-(2,2,2-trifluoroethyl)-1,3,4,5-tetrahydro-2H-1-benzazepin-2-one, using 5-(4-ethynyl-phenyl)-3-methyl-1,2,4-oxadiazole as the alkyne.

$^1$H NMR (600 MHZ, CDCl$_3$) δ 8.33 (s, 1H), 8.14 (d, J=8.4 Hz, 2H), 7.98 (d, J=8.4 Hz, 2H), 7.38 (m, 1H), 7.11 (m, 2H), 5.56 (m, 1H), 5.07 (m, 1H), 4.03 (m, 1H), 3.32 (m, 1H), 2.75 (m, 1H), 2.67 (m, 2H), 2.45 (s, 3H).

MS calculated 487.1 (MH$^+$), exp 487.0 (MH$^+$).

Example 59

6-fluoro-3-{4-[2-methoxy-4-(5-methyl-1,2,4-oxadiazol-3-yl)phenyl]-1H-1,2,3-triazol-1-yl}-1-(2,2,2-trifluoroethyl)-1,3,4,5-tetrahydro-2H-1-benzazepin-2-one

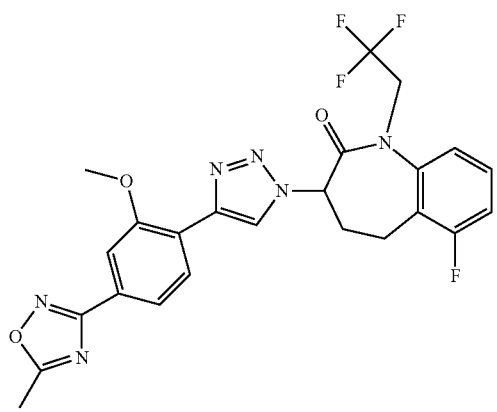 [SMILES: COc1cc(-c2noc(C)n2)ccc1-c1cn(C2CCc3c(F)cccc3N(CC(F)(F)F)C2=O)nn1]

The title compound was prepared by the same route as 6-fluoro-3-{-4-[2-fluoro-4-(pyridin-4-yl)phenyl]-1H-1,2,3-triazol-1-yl}-1-(2,2,2-trifluoroethyl)-1,3,4,5-tetrahydro-2H-1-benzazepin-2-one, using 3-(4-ethynyl-3-methoxy-phenyl)-5-methyl-1,2,4-oxadiazole as the alkyne.

$^1$H NMR (600 MHZ, CDCl$_3$) δ 8.48 (s, 1H), 8.42 (d, J=7.8 Hz, 1H), 7.76 (d, J=7.8 Hz, 1H), 7.66 (s, 1H), 7.37 (m, 1H), 7.10 (m, 2H), 5.56 (m, 1H), 5.08 (m, 1H), 4.05 (s, 3H), 4.00 (m, 1H), 3.33 (m, 1H), 2.78 (m, 2H), 2.66 (m, 4H).

MS calculated 517.2 (MH$^+$), exp 517.0 (MH$^+$).

Example 60

6-fluoro-3-{4-[4-(5-methyl-1,2,4-oxadiazol-3-yl)phenyl]-1H-1,2,3-triazol-1-yl}-1-(2,2,2-trifluoroethyl)-1,3,4,5-tetrahydro-2H-1-benzazepin-2-one

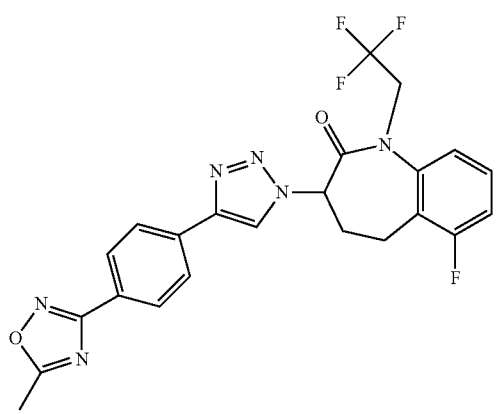 [SMILES: Cc1nc(-c2ccc(-c3cn(C4CCc5c(F)cccc5N(CC(F)(F)F)C4=O)nn3)cc2)no1]

The title compound was prepared by the same route as 6-fluoro-3-{-4-[2-fluoro-4-(pyridin-4-yl)phenyl]-1H-1,2,3- triazol-1-yl}-1-(2,2,2-trifluoroethyl)-1,3,4,5-tetrahydro-2H-1-benzazepin-2-one, using 3-(4-ethynyl-phenyl)-5-methyl-1,2,4-oxadiazole as the alkyne.

¹H NMR (600 MHZ, CDCl₃) δ 8.30 (s, 1H), 8.10 (d, J=9.0 Hz, 2H), 7.96 (d, J=9.0 Hz, 2H), 7.40 (m, 1H), 7.12 (m, 2H), 5.58 (m, 1H), 5.09 (m, 1H), 4.02 (m, 1H), 3.34 (m, 1H), 2.77 (m, 1H), 2.67 (m, 2H), 2.65 (s, 3H).

MS calculated 487.1 (MH⁺), exp 487.1 (MH⁺).

Example 61

6-fluoro-3-{4-[4-(pyridin-3-yloxy)phenyl]-1H-1,2,3-triazol-1-yl}-1-(2,2,2-trifluoroethyl)-1,3,4,5-tetrahydro-2H-1-benzazepin-2-one

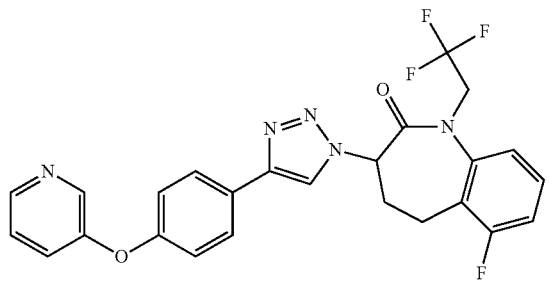 [SMILES: O=C1C(n2cc(-c3ccc(Oc4cccnc4)cc3)nn2)CCc2c(F)cccc2N1CC(F)(F)F]

4-(Pyridine-3-yloxy)ethynylbenzene (50 mg, 0.256 mmol), cupric sulfate (12.26 mg, 0.077 mmol), sodium ascorbate (20.30 mg, 0.102 mmol), and 3-azido-6-fluoro-1-(2,2,2-trifluoroethyl)-1,3,4,5-tetrahydro-2H-1-benzazepin-2-one (93 mg, 0.307 mmol) in 2.5 mL of a 1:1:1 solution of DMF:EtOH:H₂O was stirred for 25 mins. The mixture was diluted with water and EtOAc was added to extract the product. The organic phase was separated and washed with water (2×) and brine (1×) before being dried with Na₂SO₄ and evaporated to afford an oil. This material was chromatographed on silica (0-80% EtOAc in hexanes to yield 75.7 mg as a solid.

¹H NMR (600 MHz, CDCl3) δ 8.47-8.32 (m, 2H), 8.18 (s, 1H), 7.88-7.78 (m, 2H), 7.45-7.01 (m, 8H), 5.56 (dd, J=11.1, 8.7, 1H), 5.09 (td, J=17.5, 8.8, 11-1), 3.36-3.30 (m, 1H), 2.83-2.53 (m, 3H).

MS calculated 498.2 (MH⁺), exp 498.0 (MH⁺).

Example 62

6-fluoro-3-{4-[4-(pyridin-4-ylmethoxy)phenyl]-1H-1,2,3-triazol-1-yl}-1-(2,2,2-trifluoroethyl)-1,3,4,5-tetrahydro-2H-1-benzazepin-2-one

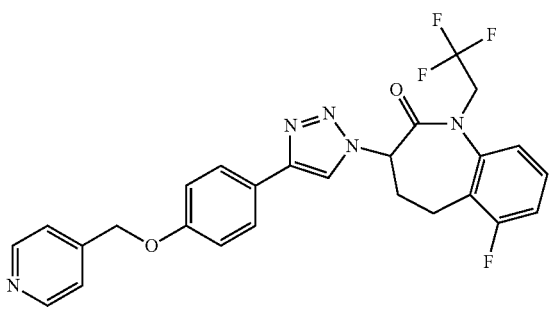 [SMILES: O=C1C(n2cc(-c3ccc(OCc4ccncc4)cc3)nn2)CCc2c(F)cccc2N1CC(F)(F)F]

Prepared as for 6-fluoro-3-{4-[4-(pyridin-3-yloxy)phenyl]-1H-1,2,3-triazol-1-yl}-1-(2,2,2-trifluoroethyl)-1,3,4,5-tetrahydro-2H-1-benzazepin-2-one, using 4-(pyridine-4-ylmethoxy)ethynylbenzene as the alkyne.

¹H NMR (600 MHz, CDCl3) δ 8.60 (dd, J=4.5, 1.5, 4H), 7.48-7.12 (m, 9H), 6.96-6.77 (m, 4H), 5.08 (s, 4H), 2.99 (s, 2H).

MS calculated 512.2 (MH⁺), exp 512.0 (MH⁺).

Example 63

6-fluoro-3-{-4-[3-fluoro-4-(pyridin-3-yloxy)phenyl]-1H-1,2,3-triazol-1-yl}trifluoroethyl)-1,3,4,5-tetrahydro-2H-1-benzazepin-2-one

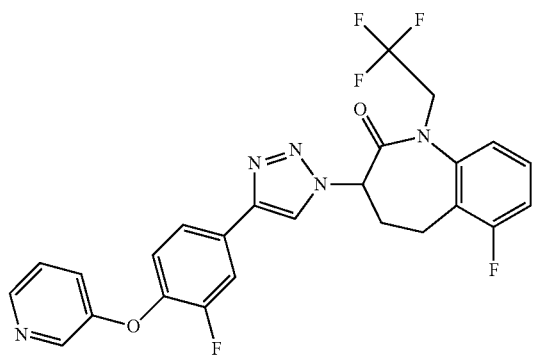 [SMILES: O=C1C(n2cc(-c3ccc(Oc4cccnc4)c(F)c3)nn2)CCc2c(F)cccc2N1CC(F)(F)F]

Prepared as for 6-fluoro-3-{4-[4-(pyridin-3-yloxy)phenyl]-1H-1,2,3-triazol-1-yl}trifluoroethyl)-1,3,4,5-tetrahydro-2H-1-benzazepin-2-one, using 3-(4-ethynyl-2-fluorophenoxy)pyridine as the alkyne.

¹H NMR (600 MHz, CDCl3) δ 8.39 (d, J=36.2, 2H), 8.21 (s, 1H), 7.71 (dd, J=11.3, 1.9, 1H), 7.59 (d, J=9.0, 1H), 7.40 (td, J=8.2, 6.0, 1H), 7.12 (dd, J=15.2, 7.9, 3H), 5.63-5.46 (m, 1H), 5.09 (dd, J=15.4, 8.7, 1H), 4.02 (dq, J=16.3, 8.3, 1H), 3.34 (dt, J=7.6, 3.5, 2H), 2.88-2.57 (m, 4H).

MS calculated 516.2 (MH⁺), exp 516.0 (MH⁺).

Example 64

6-fluoro-3-{-4-[2-methoxy-4-(pyridin-3-yloxy)phenyl]-1H-1,2,3-triazol-1-yl}-1-(2,2,2-trifluoroethyl)-1,3,4,5-tetrahydro-2H-1-benzazepin-2-one

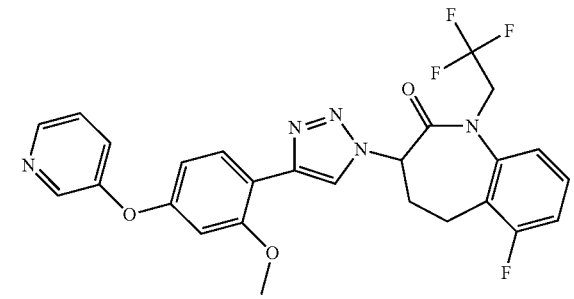 [SMILES: COc1cc(Oc2cccnc2)ccc1-c1cn(C2CCc3c(F)cccc3N(CC(F)(F)F)C2=O)nn1]

Prepared as for 6-fluoro-3-{4-[4-(pyridin-3-yloxy)phenyl]-1H-1,2,3-triazol-1-yl}-1-(2,2,2-trifluoroethyl)-1,3,4,5- tetrahydro-2H-1-benzazepin-2-one, using 3-(4-ethynyl-3-methoxyphenoxy)pyridine as the alkyne.

¹H NMR (600 MHz, CDCl3) δ 8.48-8.31 (m, 3H), 8.26 (d, J=8.5, 1H), 7.47=7.15 (m, 4H), 7.11 (t, J=8.3, 2H), 6.75=6.57 (m, 2H), 5.55 (dd, J=11.7, 8.0, 1H), 5.10 (dq, J=17.4, 8.8, 1H), 4.08 (dt, J=36.2, 18.1, 1H), 3.91 (s, 3H), 2.86-2.53 (m, 3H).

MS calculated 528.2 (MH⁺), exp 528.0 (MH⁺).

Following similar procedures and using the appropriate alkyne, the following were also prepared:

TABLE III

| Example | Structure | MS (MH⁺) |
|---|---|---|
| 65 | 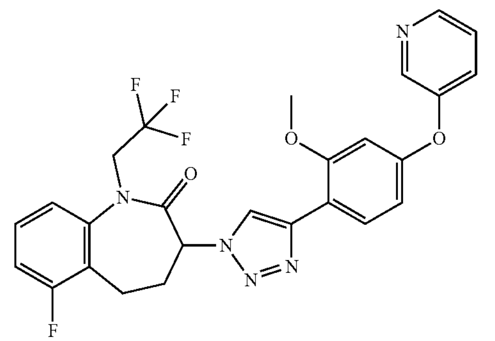 [SMILES: COc1cc(Oc2cccnc2)ccc1-c1cn(C2CCc3c(F)cccc3N(CC(F)(F)F)C2=O)nn1] | Calc'd 528.2, found 528.0 |
| 66 | 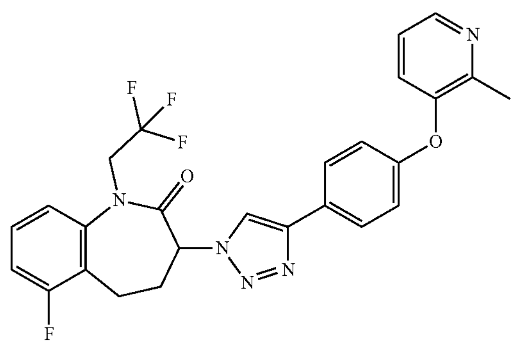 [SMILES: Cc1ncccc1Oc1ccc(-c2cn(C3CCc4c(F)cccc4N(CC(F)(F)F)C3=O)nn2)cc1] | Calc'd 512.2, found 512.0 |
| 67 | 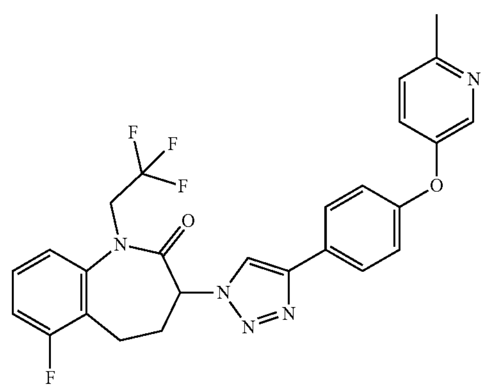 [SMILES: Cc1ccc(Oc2ccc(-c3cn(C4CCc5c(F)cccc5N(CC(F)(F)F)C4=O)nn3)cc2)cn1] | Calc'd 512.2, found 512.1 |
| 68 | 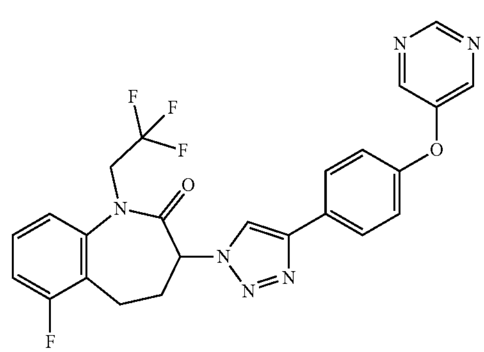 [SMILES: O=C1C(n2cc(-c3ccc(Oc4cncnc4)cc3)nn2)CCc2c(F)cccc2N1CC(F)(F)F] | Calc'd 499.1, found 499.0 |

TABLE III-continued

| Example | Structure | MS (MH+) |
|---|---|---|
| 69 | 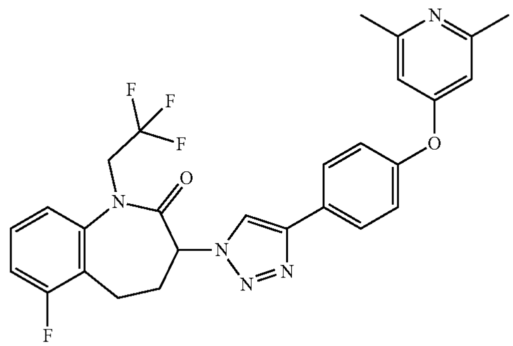 [SMILES: Cc1cc(Oc2ccc(-c3cn(C4CCc5c(F)cccc5N(CC(F)(F)F)C4=O)nn3)cc2)cc(C)n1] | Calc'd 526.2, found 526.1 |
| 70 | 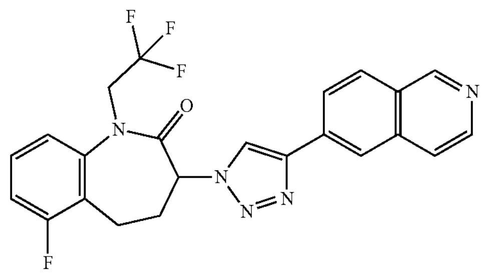 [SMILES: O=C1C(n2cc(-c3ccc4cnccc4c3)nn2)CCc2c(F)cccc2N1CC(F)(F)F] | Calc'd 456.1, found 456.0 |
| 71 | 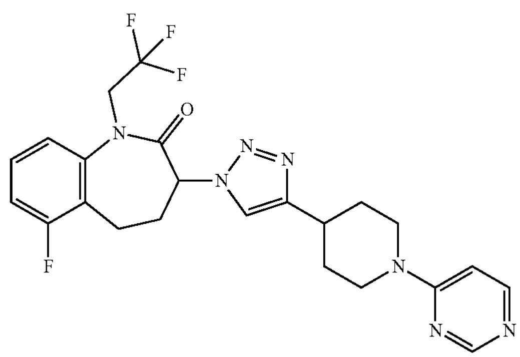 [SMILES: O=C1C(n2cc(C3CCN(c4ccncn4)CC3)nn2)CCc2c(F)cccc2N1CC(F)(F)F] | Calc'd 490.2, found 490.1 |
| 72 | 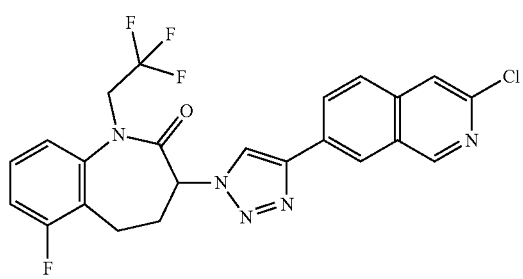 [SMILES: O=C1C(n2cc(-c3ccc4cc(Cl)ncc4c3)nn2)CCc2c(F)cccc2N1CC(F)(F)F] | Calc'd 490.1, found 490.0 |
| 73 | 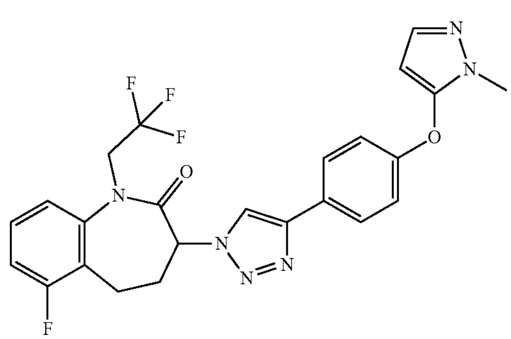 [SMILES: Cn1nccc1Oc1ccc(-c2cn(C3CCc4c(F)cccc4N(CC(F)(F)F)C3=O)nn2)cc1] | Calc'd 501.2, found 501.0 |

TABLE III-continued

| Example | Structure | MS (MH+) |
|---|---|---|
| 74 | 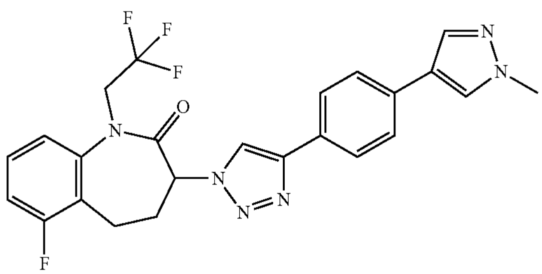 [SMILES: Cn1cc(-c2ccc(-c3cn(C4CCc5c(F)cccc5N(CC(F)(F)F)C4=O)nn3)cc2)cn1] | Calc'd 485.2, found 485.3 |
| 75 | 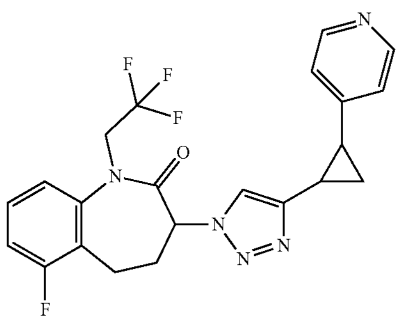 [SMILES: O=C1C(n2cc(C3CC3c3ccncc3)nn2)CCc2c(F)cccc2N1CC(F)(F)F] | Calc'd 446.2, found 446.1 |
| 76 | 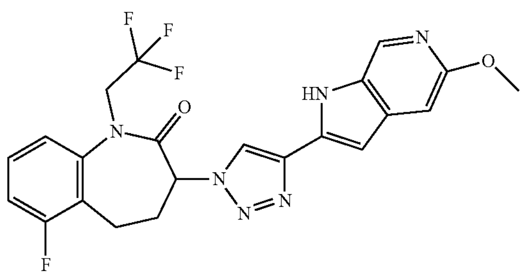 [SMILES: COc1cc2cc(-c3cn(C4CCc5c(F)cccc5N(CC(F)(F)F)C4=O)nn3)[nH]c2cn1] | Calc'd 475.2, found 475.1 |
| 77 | 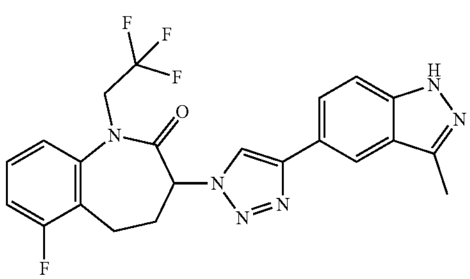 [SMILES: Cc1n[nH]c2ccc(-c3cn(C4CCc5c(F)cccc5N(CC(F)(F)F)C4=O)nn3)cc12] | Calc'd 459.2, found 459.2 |
| 78 | 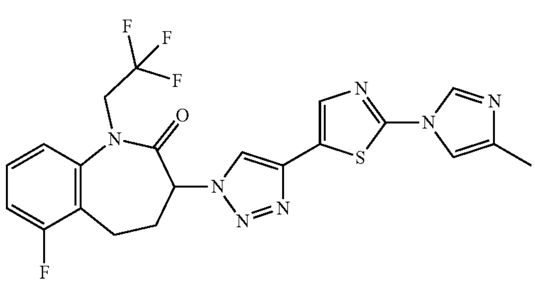 [SMILES: Cc1cn(-c2ncc(-c3cn(C4CCc5c(F)cccc5N(CC(F)(F)F)C4=O)nn3)s2)cn1] | Calc'd 492.1, found 492.1 |

TABLE III-continued

| Example | Structure | MS (MH+) |
|---|---|---|
| 79 | 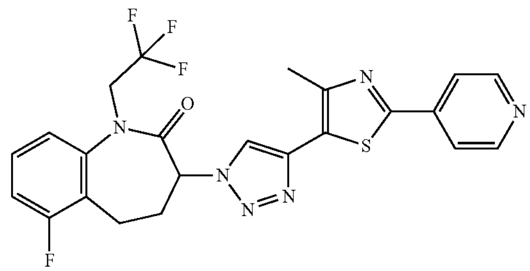 [SMILES: Cc1nc(-c2ccncc2)sc1-c1cn(C2CCc3c(F)cccc3N(CC(F)(F)F)C2=O)nn1] | Calc'd 503.1, found 503.1 |
| 80 | 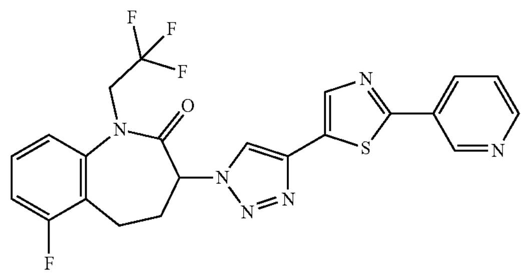 [SMILES: O=C1C(n2cc(-c3cnc(-c4cccnc4)s3)nn2)CCc2c(F)cccc2N1CC(F)(F)F] | Calc'd 489.1, found 489.1 |
| 81 | 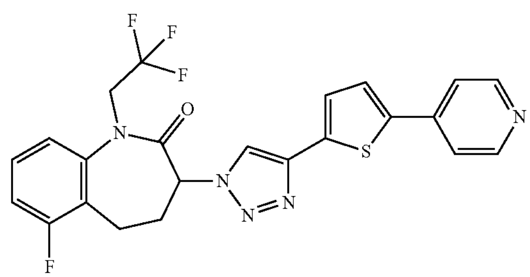 [SMILES: O=C1C(n2cc(-c3ccc(-c4ccncc4)s3)nn2)CCc2c(F)cccc2N1CC(F)(F)F] | Calc'd 488.1, found 488.1 |
| 82 | 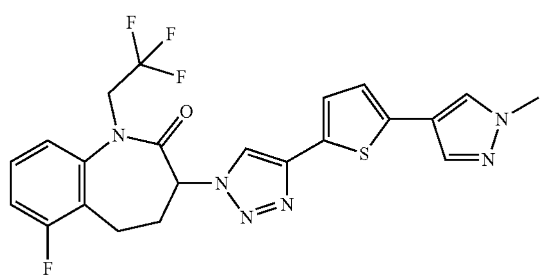 [SMILES: Cn1cc(-c2ccc(-c3cn(C4CCc5c(F)cccc5N(CC(F)(F)F)C4=O)nn3)s2)cn1] | Calc'd 491.1, found 491.1 |
| 83 | 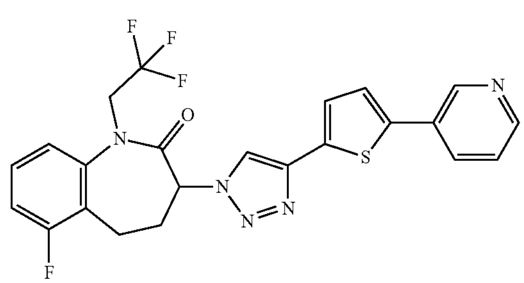 [SMILES: O=C1C(n2cc(-c3ccc(-c4cccnc4)s3)nn2)CCc2c(F)cccc2N1CC(F)(F)F] | Calc'd 488.1, found 488.1 |

TABLE III-continued

| Example | Structure | MS (MH+) |
|---|---|---|
| 84 | 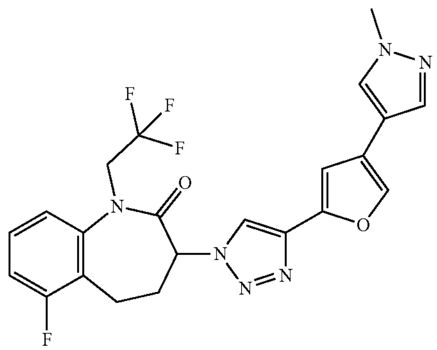 | Calc'd 475.2, found 475.1 |
| 85 | 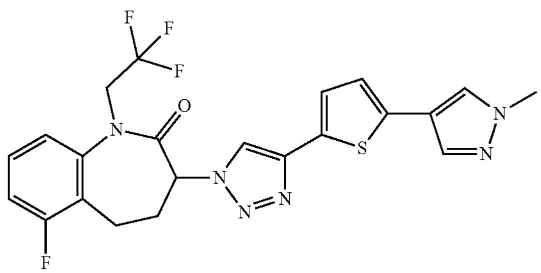 [SMILES: Cn1cc(-c2ccc(-c3cn(C4CCc5c(F)cccc5N(CC(F)(F)F)C4=O)nn3)s2)cn1] | Calc'd 491.1, found 491.1 |
| 86 | 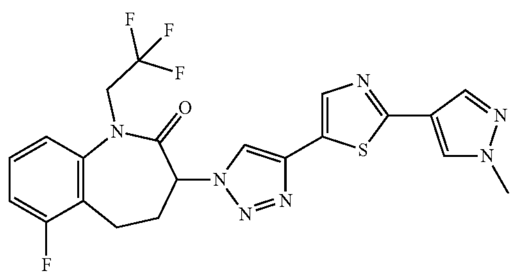 [SMILES: Cn1cc(-c2ncc(-c3cn(C4CCc5c(F)cccc5N(CC(F)(F)F)C4=O)nn3)s2)cn1] | Calc'd 492.1, found 492.1 |
| 87 | 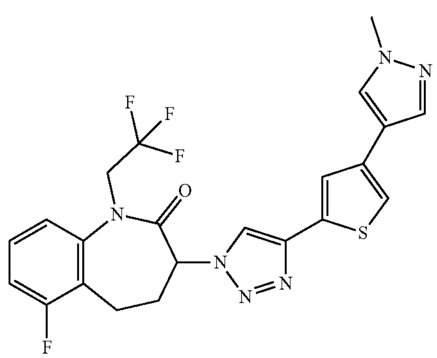 | Calc'd 491.1, found 491.0 |
| 88 | 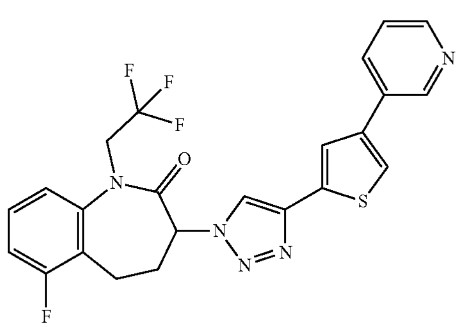 [SMILES: O=C1C(n2cc(-c3cc(-c4cccnc4)cs3)nn2)CCc2c(F)cccc2N1CC(F)(F)F] | Calc'd 488.1, found 488.1 |

TABLE III-continued

| Example | Structure | MS (MH+) |
|---|---|---|
| 89 | 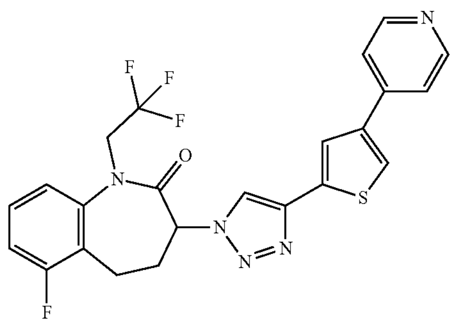 [SMILES: O=C1C(n2cc(-c3cc(-c4ccncc4)cs3)nn2)CCc2c(F)cccc2N1CC(F)(F)F] | Calc'd 488.1, found 488.1 |
| 90 | 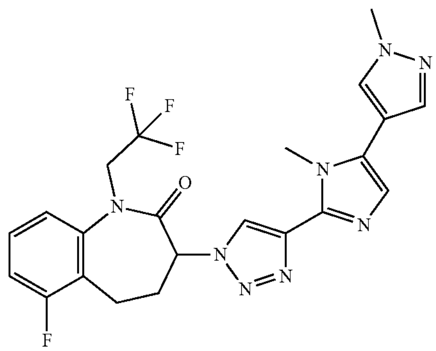 [SMILES: Cn1cc(-c2cnc(-c3cn(C4CCc5c(F)cccc5N(CC(F)(F)F)C4=O)nn3)n2C)cn1] | Calc'd 489.2, found 489.1 |

Example 91

6-fluoro-3-{4-[4-(pyridin-4-ylamino)phenyl]-1H-1,2,3-triazol-1-yl}-1-(2,2,2-trifluoroethyl)-1,3,4,5-tetrahydro-2H-1-benzazepin-2-one

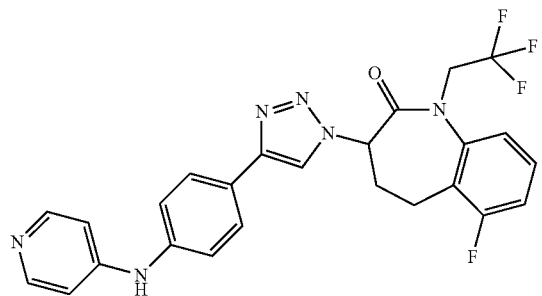 [SMILES: O=C1C(n2cc(-c3ccc(Nc4ccncc4)cc3)nn2)CCc2c(F)cccc2N1CC(F)(F)F]

A suspension of pyridin-4-amine (5.83 mg, 0.062 mmol), 3-[4-(4-bromophenyl)-1H-1,2,3-triazol-1-yl]-6-fluoro-1-(2,2,2-trifluoroethyl)-1,3,4,5-tetrahydro-2H-1-benzazepin-2-one (30 mg, 0.062 mmol), potassium carbonate (9.44 mg, 0.068 mmol), X-Phos (14.80 mg, 0.031 mmol), and tris(dibenzylideneacetone)dipalladium (11.37 mg, 0.012 mmol) were combined in a µwave vial and dissolved in t-amyl alcohol (1242 µl) The reaction was microwaved at 130° C. for 20 min.

The reaction mixture was filtered, and the solvent was removed in vacuo. Analytically pure material was obtained by purification by preparative HPLC Reverse phase (C-18), eluting with acetonitrile/water+0.05% Formic Acid. Lyophilization afforded 6-fluoro-3-{4-[4-(pyridin-4-ylamino)phenyl]-1H-1,2,3-triazol-1-yl}-1-(2,2,2-trifluoroethyl)-1,3,4,5-tetrahydro-2H-1-benzazepin-2-one.

LCMS: Calcd for $C_{25}H_{20}F_4N_6O$ [M+H]+: 497. Found: 497.

Example 92

6-fluoro-3-{4-[3-methoxy-4-(pyridin-3-ylamino)phenyl]-1H-1,2,3-triazol-1-yl}-1-(2,2,2-trifluoroethyl)-1,3,4,5-tetrahydro-2H-1-benzazepin-2-one

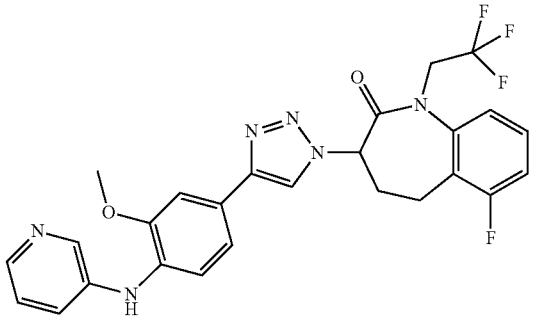 [SMILES: COc1cc(-c2cn(C3CCc4c(F)cccc4N(CC(F)(F)F)C3=O)nn2)ccc1Nc1cccnc1]

A suspension of pyridin-3-amine (5.08 mg, 0.054 mmol), 6-fluoro-3-[4-(4-iodo-3-methoxyphenyl)-1H-1,2,3-triazol-1-yl]-1-(2,2,2-trifluoroethyl)-1,3,4,5-tetrahydro-2H-1-benzazepin-2-one (30 mg, 0.054 mmol), potassium carbonate (8.14 mg, 0.059 mmol), X-Phos (12.76 mg, 0.027 mmol), and tris(dibenzylideneacetone)dipalladium (9.81 mg, 0.011 mmol) were combined in a µwave vial and dissolved in t-amyl alcohol (1071 µl). The reaction was microwaved at 130° C. for 20 min. The reaction mixture was filtered, and the solvent was removed in vacuo. Analytically pure material was obtained by purification by preparative HPLC Reverse phase (C-18), eluting with acetonitrile/water+0.05% Formic Acid. Lyophilisation afforded 6-fluoro-3-{4-[3-methoxy-4-(pyridin-3-ylamino)phenyl]-1H-1,2,3-triazol-1-yl}-1-(2,2,2-trifluoroethyl)-1,3,4,5-tetrahydro-2H-1-benzazepin-2-one LCMS: Calc'd for $C_{26}H_{22}F_4N_6O_2$ [M+1]$^+$: 527. Found: 527.

Example 93

3-{4-[3-methoxy-4-(pyridin-3-ylamino)phenyl]-1H-1,2,3-triazol-1-yl}-1-(2,2,2-trifluoroethyl)-1,3,4,5-tetrahydro-2H-1-benzazepin-2-one

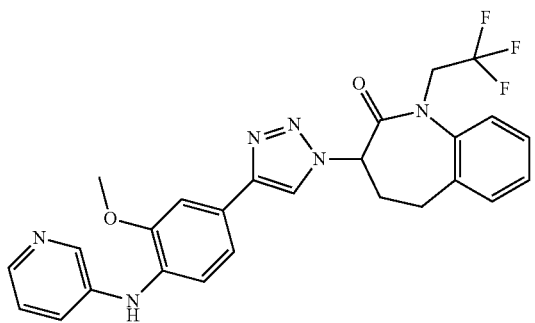 [SMILES: COc1cc(-c2cn(C3CCc4ccccc4N(CC(F)(F)F)C3=O)nn2)ccc1Nc1cccnc1]

A suspension of pyridin-3-amine (3.48 mg, 0.037 mmol 3-[4-(4-iodo-3-methoxyphenyl)-1H-1,2,3-triazol-1-yl]-1-(2,2,2-trifluoroethyl)-1,3,4,5-tetrahydro-2H-1-benzazepin-2-one (20 mg, 0.037 mmol), potassium tert-butoxide 1M in THF (36.9 µL, 0.037 mmol), BINAP (4.59 mg, 0.008 mmol), and palladium acetate (1.66 mg, 0.008 mmol) were combined in a µwave vial and dissolved in DMF (738 µl). The reaction was microwaved at 180° C. for 10 min. The reaction mixture was filtered, and the solvent was removed in vacuo. Analytically pure material was obtained by purification by preparative HPLC Reverse phase (C-18), eluting with acetonitrile/water+0.05% Formic Acid. Lyophilisation afforded 3-{4-[3-methoxy-4-(pyridin-3-ylamino)phenyl]-1H-1,2,3-triazol-1-yl}-1-(2,2,2-trifluoroethyl)-1,3,4,5-tetrahydro-2H-1-benzazepin-2-one LCMS: Calc'd for $C_{26}H_{23}F_3N_6O_2$ [M+1]$^+$: 511. Found: 511.

Example 94

3-{-4-[3-methoxy-4-(1,3-thiazol-2-ylamino)phenyl]-H-1,2,3-triazol-1-yl}-1-(2,2,2-trifluoroethyl)-1,3,4,5-tetrahydro-2H-1-benzazepin-2-one

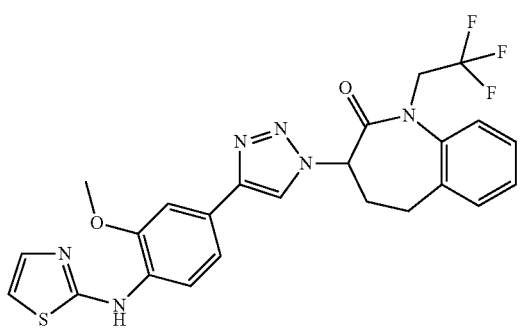 [SMILES: COc1cc(-c2cn(C3CCc4ccccc4N(CC(F)(F)F)C3=O)nn2)ccc1Nc1nccs1]

A suspension of 1,3-thiazol-2-amine (5.54 mg, 0.055 mmol 3-[4-(4-iodo-3-methoxyphenyl)-1H-1,2,3-triazol-1-yl]-1-(2,2,2-trifluoroethyl)-1,3,4,5-tetrahydro-2H-1-benzazepin-2-one (20 mg, 0.037 mmol), potassium tert-butoxide 1M in THF (36.9 µL, 0.037 mmol), BINAP (4.59 mg, 0.008 mmol), and palladium acetate (1.66 mg, 0.008 mmol) were combined in a µwave vial and dissolved in DMF (738 µl). The reaction was microwaved at 180° C. for 5 minutes. The reaction mixture was filtered, and the solvent was removed in vacuo. Analytically pure material was obtained by purification by preparative HPLC Reverse phase (C-18), eluting with acetonitrile/water+0.05% Formic Acid. Lyophilisation afforded 3-{4-[3-methoxy-4-(1,3-thiazol-2-ylamino)phenyl]-1H-1,2,3-triazol-1-yl}-1-(2,2,2-trifluoroethyl)-1,3,4,5-tetrahydro-2H-1-benzazepin-2-one.

LCMS: Calc'd for $C_{24}H_{21}F_3N_6O_2S$ [M+1]$^+$: 515. Found: 515.

Example 95

6-fluoro-3-{-4-[3-methoxy-4-(pyridin-4-ylamino)phenyl]-1H-1,2,3-triazol-1-yl}trifluoroethyl)-1,3,4,5-tetrahydro-2H-1-benzazepin-2-one

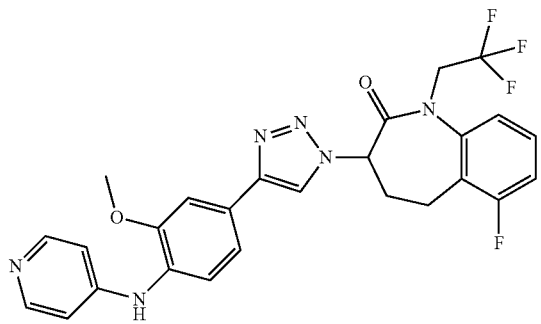 [SMILES: COc1cc(-c2cn(C3CCc4c(F)cccc4N(CC(F)(F)F)C3=O)nn2)ccc1Nc1ccncc1]

A suspension of 6-fluoro-3-[4-(4-iodo-3-methoxyphenyl)-1H-1,2,3-triazol-1-yl]-1-(2,2,2-trifluoroethyl)-1,3,4,5-tetrahydro-2H-1-benzazepin-2-one (50 mg, 0.089 mmol), 18-CROWN-6 (28.3 mg, 0.107 mmol), pyridin-4-amine (9.24 mg, 0.098 mmol), BINAP (11.11 mg, 0.018 mmol), sodium tert-butoxide (17.15 mg, 0.178 mmol), and tris(dibenzylideneacetone)dipalladium (4.09 mg, 4.46 µmol) were combined in a microwave vial and dissolved in THF (892 µl). The reaction was irradiated in the microwave at 160° C. for 15 minutes. The reaction mixture was filtered, and the solvent was removed in vacuo. Analytically pure material was obtained by purification by preparative HPLC Reverse phase (C-18), eluting with acetonitrile/water+0.05% Formic Acid. Lyophilisation afforded 6-fluoro-3-{-4-[3-methoxy-4-(pyridin-4-ylamino)phenyl]-1H-1,2,3-triazol-1-yl}-1-(2,2,2-trifluoroethyl)-1,3,4,5-tetrahydro-2H-1-benzazepin-2-one.

LCMS: Calc'd for $C_{26}H_{22}F_4N_6O_2$ [M+1]$^+$: 527. Found: 527.

Following similar procedures and using the appropriate amine, the following were also prepared:

TABLE IV
| Example | Structure | MS (MH+) |
|---|---|---|
| 96 | 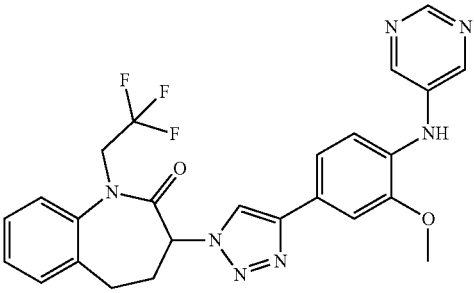 [SMILES: COc1cc(-c2cn(C3CCc4ccccc4N(CC(F)(F)F)C3=O)nn2)ccc1Nc1cncnc1] | Calc'd 510.2, found 511 |
| 97 | 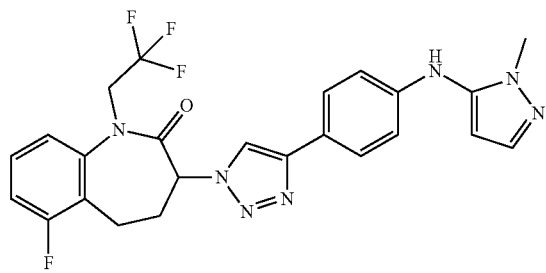 [SMILES: Cn1nccc1Nc1ccc(-c2cn(C3CCc4c(F)cccc4N(CC(F)(F)F)C3=O)nn2)cc1] | Calc'd 500.2, found 501 |
| 98 | 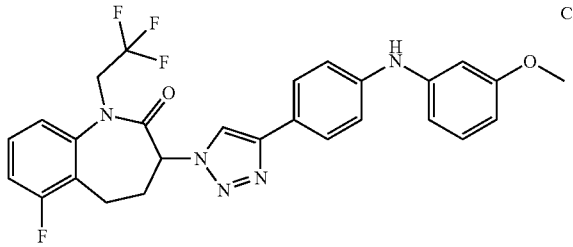 | Calc'd 526.2, found 527 |
| 99 | 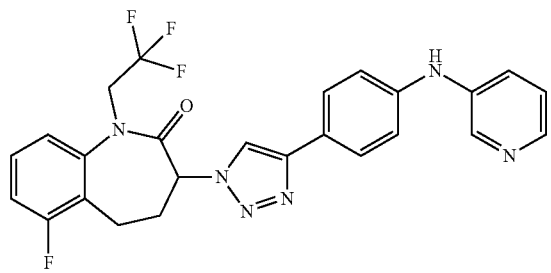 [SMILES: O=C1C(n2cc(-c3ccc(Nc4cccnc4)cc3)nn2)CCc2c(F)cccc2N1CC(F)(F)F] | Calc'd 497.2, found 498 |
| 100 | 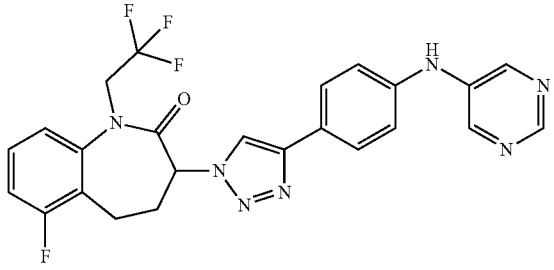 [SMILES: O=C1C(n2cc(-c3ccc(Nc4cncnc4)cc3)nn2)CCc2c(F)cccc2N1CC(F)(F)F] | Calc'd 498.2, found 499 |

TABLE IV-continued
| Example | Structure | MS (MH+) |
|---|---|---|
| 101 | 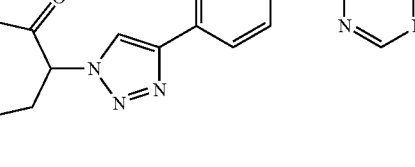 | Calc'd 498.2, found 499 |
| 102 | 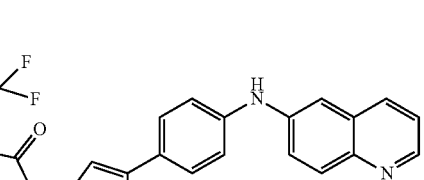 | Calc'd 547.2, found 548 |
| 103 | 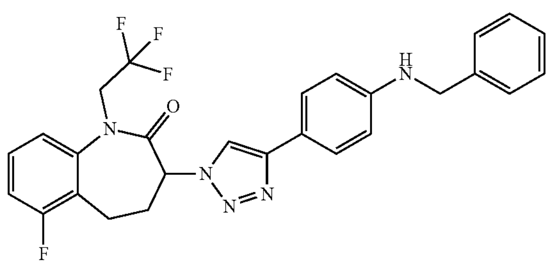 [SMILES: O=C1C(n2cc(-c3ccc(NCc4ccccc4)cc3)nn2)CCc2c(F)cccc2N1CC(F)(F)F] | Calc'd 510.2, found 511 |
| 104 | 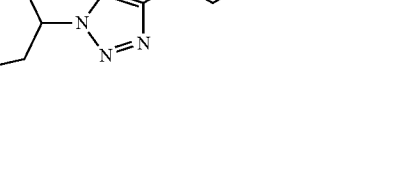 | Calc'd 556.2, found 557 |

TABLE IV-continued
| Example | Structure | MS (MH+) |
|---|---|---|
| 105 | 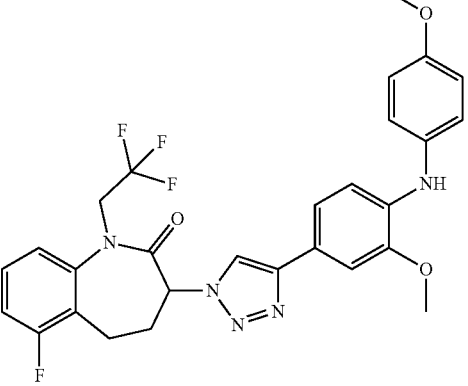 | Calc'd 556.2, found 557 |
| 106 | 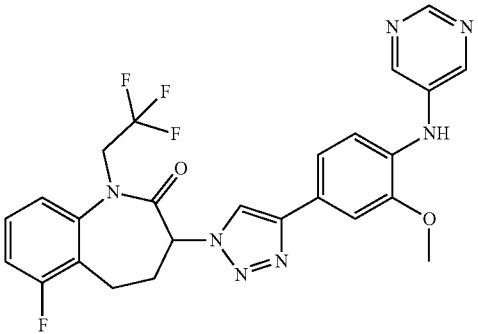 [SMILES: COc1cc(-c2cn(C3CCc4c(F)cccc4N(CC(F)(F)F)C3=O)nn2)ccc1Nc1cncnc1] | Calc'd 528.2, found 529 |
| 107 | 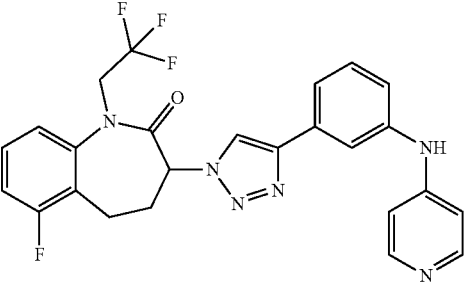 [SMILES: O=C1C(n2cc(-c3cccc(Nc4ccncc4)c3)nn2)CCc2c(F)cccc2N1CC(F)(F)F] | Calc'd 497.2, found 498 |
| 108 | 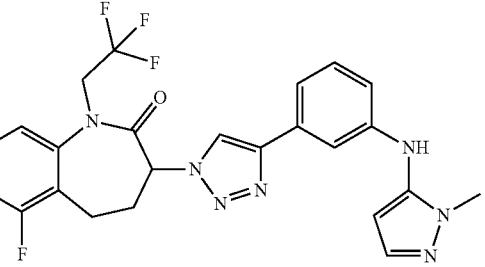 | Calc'd 500.2, found 501 |

Example 109

6-fluoro-3-{4-[1-(pyridin-4-ylcarbonyl)piperidin-4-yl]-1H-1,2,3-triazol-1-yl}-1-(2,2,2-trifluoroethyl)-1,3,4,5-tetrahydro-2H-1-benzazepin-2-one

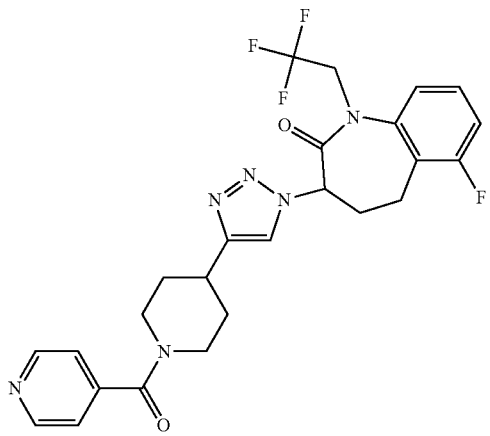 [SMILES: O=C(c1ccncc1)N1CCC(c2cn(C3CCc4c(F)cccc4N(CC(F)(F)F)C3=O)nn2)CC1]

6-Fluoro-3-[4-(piperidin-4-yl)-H-1,2,3-triazol-1-yl]-1-(2,2,2-trifluormethyl)-1,3,4,5-tetrahydro-2H-1-benzazepin-2-one (40 mg, 0.097 mmol) and isonicotinoyl chloride hydrochloride (21 mg, 0.12 mmol) was dissolved in DCM (1 mL) and Et₃N (40 uL, 0.29 mmol) was added. The mixture was stirred at ambient temperature for 1 h. After solvent removal under reduced pressure, the residue was purified by column chromatography on silica gel to afford 56 mg title compound.

¹H NMR (600 MHZ, CDCl₃) δ 8.66 (d, J=6.0 Hz, 2H), 7.72 (s, 1H), 7.36 (m, 1H), 7.26 (d, J=6.0 Hz, 2H), 7.09 (m, 2H), 5.48 (m, 1H), 5.04 (m, 1H), 4.70 (broad s, 1H), 4.00 (m, 1H), 3.66 (d, J=13.2 Hz, 1H), 3.29-2.57 (m, 7H), 2.17-1.65 (m, 4H).

MS calculated 517.2 (MH⁺), exp 517.1 (MH⁺).

Example 110

6-fluoro-3-{4-[1-(pyrimidin-4-yl)piperidin-4-yl]-1H-1,2,3-triazol-1-yl}-1-(2,2,2-trifluoroethyl)-1,3,4,5-tetrahydro-2H-1-benzazepin-2-one

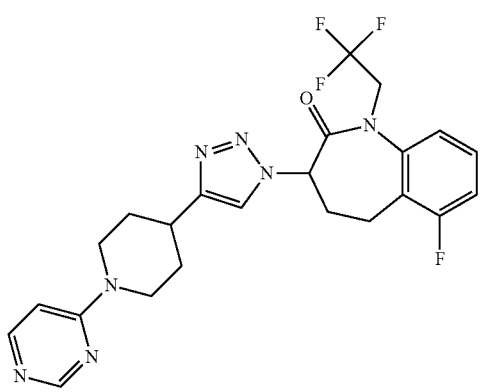 [SMILES: O=C1C(n2cc(C3CCN(c4ccncn4)CC3)nn2)CCc2c(F)cccc2N1CC(F)(F)F]

In a sealed tube, 6-fluoro-3-[4-(piperidin-4-yl)-1H-1,2,3-triazol-1-yl]-1-(2,2,2-trifluoroethyl)-1,3,4,5-tetrahydro-2H-1-benzazepin-2-one (50 mg, 0.122 mmol), 4-chloropyrimidine hydrochloride (27.5 mg, 0.182 mmol) and DIEA (212 uL, 1.215 mmol) in 2-propanol (1.2 mL) was heated at 140° C. for 1 h. After cooling to ambient temperature and solvent removal under reduced pressure, the residue was purified by column chromatography on silica gel to afford 46 mg title compound.

¹H NMR (600 MHZ, CDCl₃) δ 8.56 (s, 1H), 8.15 (d, J=6.0 Hz, 1H), 7.70 (s, 1H), 7.36 (m, 1H), 7.08 (m, 2H), 6.51 (d, J=6.0 Hz, 1H), 5.47 (m, 1H), 5.04 (m, 1H), 4.42 (m, 1H), 3.98 (m, 1H), 3.28 (m, 1H), 3.08 (m, 4H), 2.70 (m, 1H), 2.60 (m, 2H), 2.14 (d, J=12.6 Hz, 2H), 1.70 (m, 2H).

MS calculated 490.2 (MH⁺), exp 490.1 (MH⁺).

Example 111

4-{1-[6-fluoro-2-oxo-1-(2,2,2-trifluoroethyl)-2,3,4,5-tetrahydro-1H-1-benzazepin-3-yl]-1H-1,2,3-triazol-4-yl}-2H-1,4'-bipyridin-2-one

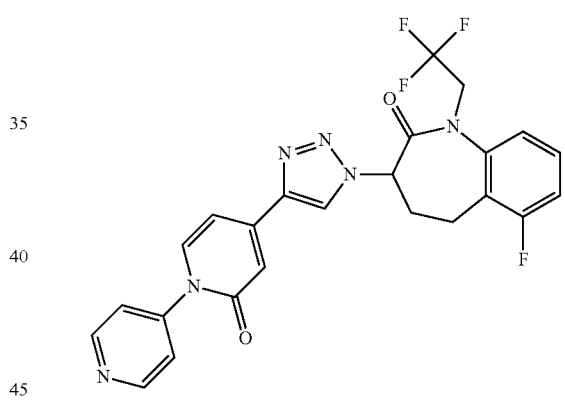

6-Fluoro-3-[4-(2-oxo-1,2-dihydropyridin-4-yl)-1H-1,2,3-triazol-1-yl]-1-(2,2,2-trifluoroethyl)-1,3,4,5-tetrahydro-2H-1-benzazepin-2-one (20 mg, 0.047 mmol), CuI (2 mg, 0.01 mmol), 4,7-dimethoxy-1,10-phenanthroline (3.5 mg, 0.015 mmol), 4-iodopyridine (12 mg, 0.057 mmol) and K₂CO₃ (13 mg, 0.095 mmol) in 0.5 mL DMF was heated at 120° C. for 3 h. After cooled to ambient temperature, the mixture was filtered with a Whatman 0.45 uM filter disk and the washed with 2:1 DCM/MeOH. The solvent was reduced under reduced pressure and the residue was purified by column chromatography on silica gel (0-15% MeOH in DCM) to afford 21 mg title compound.

¹H NMR (600 MHZ, CDCl₃) δ 8.76 (broad s, 2H), 8.35 (s, 1H), 7.44-7.38 (m, 4H), 7.12 (m, 2H), 7.01 (s, 1H), 6.92 (dd, J=1.8, 7.2 Hz, 1H), 5.56 (m, 1H), 5.07 (m, 1H), 4.03 (m, 1H), 3.33 (m, 1H), 2.77-2.67 (m, 3H).

MS calculated 499.1 (MH⁺), exp 499.0 (MH⁺).

Example 112

6-fluoro-3-(4-{4-[(2-methylpyridin-3-yl)oxy]phenyl}-1H-1,2,3-triazol-1-yl)-1-(2,2,2-trifluoroethyl)-1,3,4,5-tetrahydro-2H-1-benzazepin-2-one

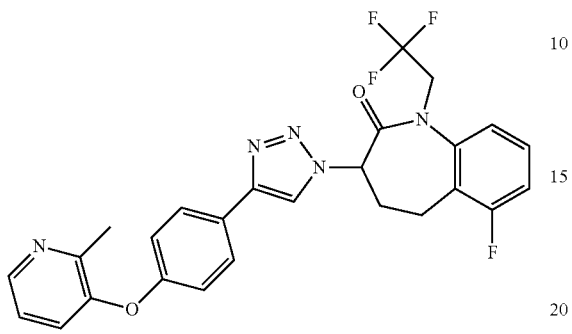

3-[4-(4-Bromophenyl)-1H-1,2,3-triazol-1-yl]-6-fluoro-1-(2,2,2-trifluoroethyl)-1,3,4,5-tetrahydro-2H-1-benzazepin-2-one (150 mg, 0.310 mmol), cesium carbonate (202 mg, 0.621 mmol), 3-hydroxy-2-methylpyridine (67.7 mg, 0.621 mmol), cuprous chloride (915.36 mg, 0.155 mmol), 2,2,6,6-tetramethyl-3,5-heptanedione (14.30 mg, 0.078 mmol) in NMP (1.55 mL) in a sealed microwave vial was heated to 120° C. overnight in an oil bath. The reaction vessel was allowed to cool before water was added to dilute the mixture; EtOAc was then added to extract the product. The organic phase was separated and washed with water (2×) and brine (1×) before being dried with $Na_2SO_4$ and evaporated to afford an oil. This material was chromatographed on silica (0-80% EtOAc in hexanes to yield 68.4 mg as a solid.

$^1$H NMR (600 MHz, CDCl3) δ 8.30 (d, J=4.7, 1H), 8.17 (s, 1H), 7.80 (d, J=8.7, 2H), 7.49-6.88 (m, 5H), 5.56 (dd, J=11.1, 8.6, 2H), 5.09 (td, J=17.1, 8.5, 1H), 4.01 (dt, J=16.3, 8.2, 1H), 3.35-3.24 (m, 1H), 2.83-2.58 (m, 3H), 2.50 (d, J=7.7, 4H).

MS calculated 512.2 (MH$^+$), exp 512.0 (MH$^+$).

Example 113

6-fluoro-3-(4-{4-[(6-methylpyridin-3-yl)oxy]phenyl}-1H-1,2,3-triazol-1-yl)-1-(2,2,2-trifluoroethyl)-1,3,4,5-tetrahydro-2H-1-benzazepin-2-one

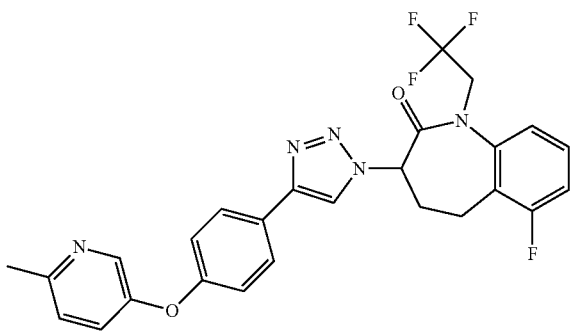 [SMILES: Cc1ccc(Oc2ccc(-c3cn(C4CCc5c(F)cccc5N(CC(F)(F)F)C4=O)nn3)cc2)cn1]

Prepared as for 6-fluoro-3-(4-{4-[(2-methylpyridin-3-yl)oxy]phenyl}-1H-1,2,3-triazol-1-yl)-1-(2,2,2-trifluoroethyl)-1,3,4,5-tetrahydro-2H-1-benzazepin-2-one, using 5-hydroxy-2-methylpyridine.

$^1$H NMR (600 MHz, CDCl$_3$) δ 8.61 (dd, J=4.5, 1.5, 2H), 8.13 (s, 1H), 7.77 (d, J=8.7, 2H), 7.43-7.32 (m, 3H), 7.16-7.08 (m, 2H), 7.03-6.97 (m, 2H), 5.55 (dd, J=11.4, 8.4, 1H), 5.10-4.98 (m, 1H), 4.01 (dd, J=15.5, 8.1, 1H), 3.35-3.29 (m, 1H), 2.68 (ddd, J=29.3, 10.2, 6.9, 4H), 2.02 (s, 2H).

MS calculated 512.2 (MH$^+$), exp 512.0 (MH$^+$).

Example 114

6-fluoro-3-{4-[4-(pyrimidin-5-yloxy)phenyl]-1H-1,2,3-triazol-1-yl}-1-(2,2,2-trifluoroethyl)-1,3,4,5-tetrahydro-2H-1-benzazepin-2-one

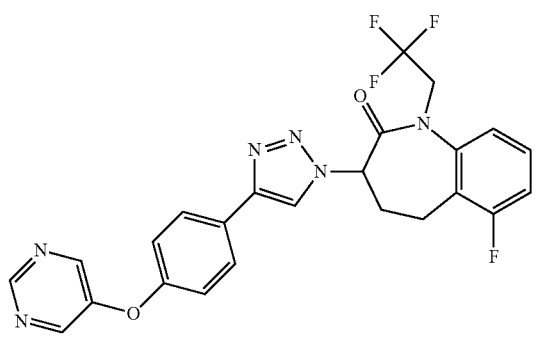 [SMILES: O=C1C(n2cc(-c3ccc(Oc4cncnc4)cc3)nn2)CCc2c(F)cccc2N1CC(F)(F)F]

Prepared as for 6-fluoro-3-(4-{4-[(2-methylpyridin-3-yl)oxy]phenyl-1H-1,2,3-triazol-1-yl}-1-(2,2,2-trifluoroethyl)-1,3,4,5-tetrahydro-2H-1-benzazepin-2-one, using 5-hydroxypyrimidine.

$^1$H NMR (600 MHz, CDCl3) δ 8.98 (s, 1H), 8.50 (s, 2H), 8.21 (s, 1H), 7.88 (d, J=8.6, 2H), 7.47-7.31 (m, 1H), 7.12 (dd, J=16.3, 8.5, 3H), 5.65-5.44 (m, 1H), 5.28 (s, 1H), 5.09 (td, J=17.0, 8.4, 1H), 4.02 (dt, J=16.0, 8.1, 1H), 3.33 (dd, J=11.8, 3.1, 1H), 2.87-2.52 (m, 3H).

MS calculated 499.1 (MH$^+$), exp 499.0 (MH$^+$).

Example 115

3-(4-{4-[(2,6-dimethylpyridin-4-yl)oxy]phenyl}-1H-1,2,3-triazol-1-yl)-6-fluoro-1-(2,2,2-trifluoroethyl)-1,3,4,5-tetrahydro-2H-1-benzazepin-2-one

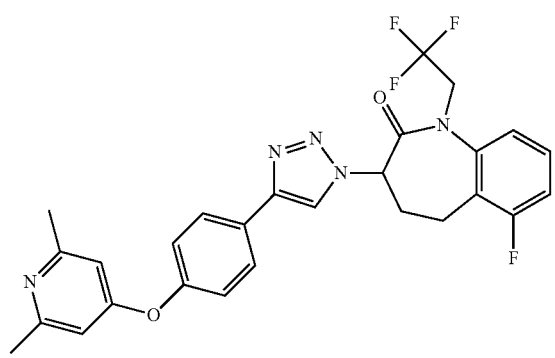 [SMILES: Cc1cc(Oc2ccc(-c3cn(C4CCc5c(F)cccc5N(CC(F)(F)F)C4=O)nn3)cc2)cc(C)n1]

Prepared as for 6-fluoro-3-(4-{4-[(2-methylpyridin-3-yl)oxy]phenyl}-1H-1,2,3-triazol-1-yl)-1-(2,2,2-trifluoroethyl)-1,3,4,5-tetrahydro-2H-1-benzazepin-2-one, using 2,6-dimethyl-4-hydroxypyridine.

¹H NMR (600 MHz, CDCl3) δ 8.31 (s, 1H), 8.17 (s, 1H), 7.80 (d, J=8.6, 2H), 7.39 (dd, J=14.3, 8.2, 1H), 7.24 (s, 4H), 7.12 (dd, J=15.6, 8.1, 3H), 7.02 (d, J=8.7, 2H), 5.56 (dd, J=11.0, 8.7, 1H), 5.09 (dd, J=15.4, 8.7, 1H), 4.06 (ddd, J=23.7, 14.9, 7.7, 2H), 3.40-3.23 (m, 1H), 2.67 (dd, J=11.1, 7.6, 3H), 2.02 (s, 2H).

MS calculated 526.2 (MH⁺), exp 526.1 (MH⁺).

Example 116

6-fluoro-3-(4-{4-[(1-methyl-1H-pyrazol-5-yl)oxy]phenyl}-1H-1,2,3-triazol-1-yl)-1-(2,2,2-trifluoroethyl)-1,3,4,5-tetrahydro-2H-1-benzazepin-2-one

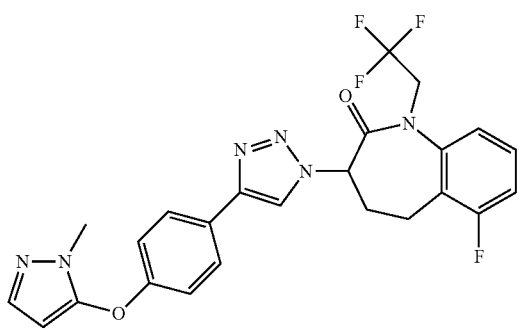 [SMILES: Cn1nccc1Oc1ccc(-c2cn(C3CCc4c(F)cccc4N(CC(F)(F)F)C3=O)nn2)cc1]

Prepared as for 6-fluoro-3-(4-{4-[(2-methylpyridin-3-yl)oxy]phenyl}-1H-1,2,3-triazol-1-yl)-1-(2,2,2-trifluoroethyl)-1,3,4,5-tetrahydro-2H-1-benzazepin-2-one, using 5-hydroxy-1-methyl-1H-pyrazole.

¹H NMR (600 MHz, CDCl3) δ 8.25 (s, 1H), 7.93 (d, J=8.5, 2H), 7.49-7.31 (m, 2H), 7.32-7.18 (m, 3H), 7.13 (dd, J=16.4, 8.2, 2H), 5.71-5.45 (m, 2H), 5.08 (dq, J=17.5, 8.7, 1H), 3.47 (d, J=5.2, 1H), 3.38-3.19 (m, 3H), 2.86-2.55 (m, 3H).

MS calculated 501.2 (MH⁺), exp 501.0 (MH⁺).

Example 117

6-Fluoro-3-[4-(2-methyl-pyridin-4-ylethynyl)-1,2,3-triazol-1-yl]-1-(2,2,2-trifluoro-ethyl)-1,3,4,5-tetrahydro-1-benzazepin-2-one

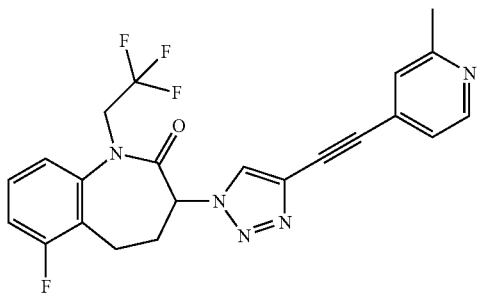 [SMILES: Cc1cc(C#Cc2cn(C3CCc4c(F)cccc4N(CC(F)(F)F)C3=O)nn2)ccn1]

Triethylsilanyl-propynal (500 mg, 2.97 mmol) and potassium carbonate (821 mg, 5.94 mmol) were placed in a 25-mL flask under nitrogen and methanol (20 ml) was added. To the yellowish suspension was added (1-diazo-2-oxo-propyl)-phosphoric acid dimethyl ester (0.5 ml, 3.20 mmol) via syringe. The reaction mixture was stirred at room temperature for 16 h. The solvent was evaporated, water added and the reaction mixture extracted with dichloromethane (3×10 mL). The solvent was evaporated and the crude material used without purification.

To the snide material was added 3-azido-6-fluoro-1-(2,2,2-trifluoroethyl)-1,3,4,5-tetrahydro-2H-1-benzazepin-2-one (100 mg, 0.33 mmol) in a 50-mL flask. Ethanol (20 mL), water (5 mL), and sodium ascorbate (39.3 mg, 0.199 mmol) as well as copper(II) sulfate solution (1M, 0.165 ml, 0.165 mmol) were added. Precipitation occurred and the yellow suspension was stirred for 16 h at room temperature. The volatiles were removed and the solid dispersed in MeOH/TFA. The crude material was purified by preparative HPLC Reverse phase (C-18), eluting with Acetonitrile/Water+0.1% TFA, to give 3-(4-triethylsilanylethynyl-1,2,3-triazol-1-yl)-1-(2,2,2-trifluoro-ethyl)-1,3,4,5-tetrahydro-1-benzazepin-2-one (containing some des-silyl compound) after solvent evaporation.

THF (5 ml) as well as TBAF (1M in THF, 0.5 mL, 0.500 mmol) were added. The brownish solution was stirred for 3 h at room temperature and LCMS indicated formation of 3-(4-Ethynyl-1,2,3-triazol-1-yl)-1-(2,2,2-trifluoro-ethyl)-1,3,4,5-tetrahydro-1-benzazepin-2-one. The solvent was evaporated and the residue was purified by preparative HPLC Reverse phase (C-18), eluting with Acetonitrile/Water+0.1% TFA to give no separation. All fractions were collected and the solvents evaporated. After extraction with dichloromethane a brownish oil was obtained, which contained the desired alkyne as well as TBAF. The material was carried on to the final transformation without further purification.

Triethyl amine (0.030 ml, 0.213 mmol), 4-bromo-2-methylpyridine (19 mg, 0.111 mmol), bis(triphenylphosphino)palladium dichloride (6 mg, 8.55 μmol), and DMF (2 ml) were added to the 25-mL flask containing the crude 3-(4-Ethynyl-1,2,3-triazol-1-yl)-1-(2,2,2-trifluoro-ethyl)-1,3,4,5-tetrahydro-1-benzazepin-2-one and the resulting brownish solution was degassed for 15 minutes by bubbling nitrogen through. Copper(I) iodide (1 mg, 5.25 μmol) was added and the mixture heated to 90° C. for 14 h. After cooling to room temperature the reaction mixture was passed through a silica gel pipette and the residue was purified by preparative HPLC Reverse phase (C-18), eluting with Acetonitrile/Water+0.1% TFA, to give the product as a colorless solid with some TBAF contamination. The residue was purified by column chromatography on silica gel (10 g prepacked) eluting with EtOAc/MeOH to give 3-[4-(2-Methyl-pyridin-4-ylethynyl)-1,2,3-triazol-1-yl]-1-(2,2,2-trifluoro-ethyl)-1,3,4,5-tetrahydro-1-benzazepin-2-one (11 mg) as a colorless solid.

LCMS (EI) calc'd for (C₂₃H₁₈F₄N₅O) [M+H]⁺, 444.1. found 444.1.

Example 118

3-{4-[4-(2-ethylpyridin-4-yl)-3-methoxyphenyl]-1H-1,2,3-triazol-1-yl}-1-(2,2,2-trifluoroethyl)-1,3,4,5-tetrahydro-2H-1-benzazepin-2-one

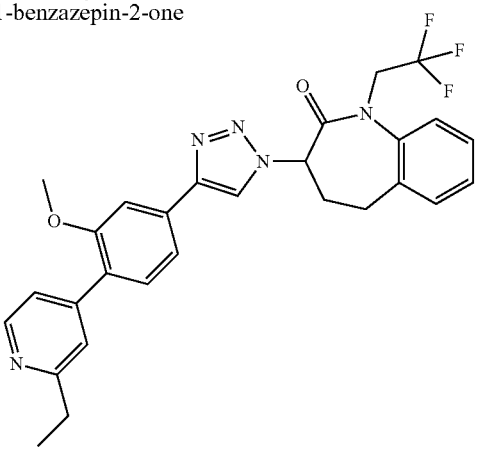

To a stirred suspension of 3-{4-[4-(2-chloropyridin-4-yl)-3-methoxyphenyl]-1H-1,2,3-triazol-1-yl}-1-(2,2,2-trifluo roethyl)-1,3,4,5-tetrahydro-2H-1-benzazepin-2-one (50 mg, 0.095 mmol), previously prepared, and ferric acetylacetonate (3.34 mg, 9.47 μmol) in THF (852 μl) and NMP (95 μl) at 0° C. was added ethyl magnesium bromide (1M in THF, 189 μl, 0.189 mmol). The reaction was held at 0° C. and stirred for 15 minutes. The reaction was quenched at 0° C. with a small addition of 1 mL of a saturated NH₄Cl aq. solution. The reaction was diluted with 50 mL of H₂O and was extracted with 3×50 mL portions of DCM. The combined organic layers were dried over anhydrous magnesium sulfate, filtered and concentrated in vacuo Analytically pure material was obtained by purification by preparative HPLC Reverse phase (C-18), eluting with acetonitrile/water+0.05% Formic Acid. Lyophilisation afforded 3-{4-[4-(2-ethylpyridin-4-yl)-3-methoxyphenyl]-1H-1,2,3-triazol-1-yl}-1-(2,2,2-trifluoroethyl)-1,3,4,5-tetrahydro-2H-1 benzazepin-2-one.

Calc'd for $C_{28}H_{26}F_3N_5O_2$ [M+1]⁺: 522. Found: 522.

Example 119

3-{4-[4-(2-isopropylpyridin-4-yl)-3-methoxyphenyl]-1H-1,2,3-triazol-1-yl}-1-(2,2,2-trifluoroethyl)-1,3,4,5-tetrahydro-2H-1-benzazepin-2-one

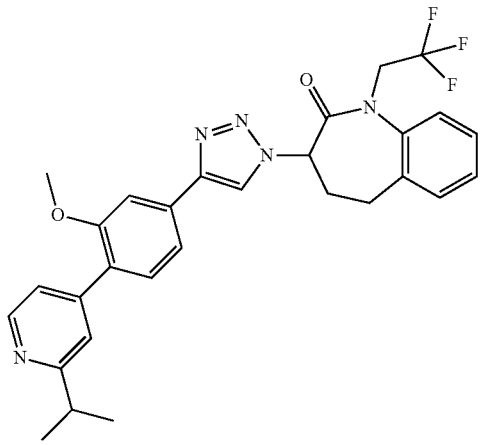 [SMILES: COc1cc(-c2cn(C3CCc4ccccc4N(CC(F)(F)F)C3=O)nn2)ccc1-c1ccnc(C(C)C)c1]

3-{4-[4-(2-Isopropylpyridin-4-yl)-3-methoxyphenyl]-1H-1,2,3-triazol-1-yl}-1-(2,2,2-trifluoroethyl)-1,3,4,5-tetrahydro-2H-1-benzazepin-2-one was prepared by using the same procedure described for 3-{4-[4-(2-ethylpyridin-4-yl)-3-methoxyphenyl]-1H-1,2,3-triazol-1-yl}-1-(2,2,2-trifluoroethyl)-1,3,4,5-tetrahydro-2H-1-benzazepin-2-one with isopropyl magnesium bromide (1M in THF, 189 μl, 0.189 mmol), and 3-{4-[4-(2-chloropyridin-4-yl)-3-methoxyphenyl]-1H-1,2,3-triazol-1-yl}-1-(2,2,2-trifluoroethyl)-1,3,4,5-tetrahydro-2H-1-benzazepin-2-one (50 mg, 0.095 mmol).

Calcd for $C_{29}H_{28}F_3N_5O_2$ [M+1]⁺: 536. Found: 536.

Example 120

6-fluoro-3-[4-(3-pyridin-3-ylphenyl)-1H-1,2,3-triazol-1-yl]-1-(2,2,2-trifluoroethyl)-1,3,4,5-tetrahydro-2H-1-benzazepin-2-one

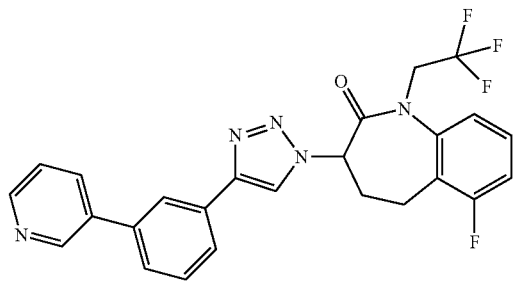 [SMILES: O=C1C(n2cc(-c3cccc(-c4cccnc4)c3)nn2)CCc2c(F)cccc2N1CC(F)(F)F]

3-[4-(3-Chlorophenyl)-1H-1,2,3-triazol-1-yl]-6-fluoro-1-(2,2,2-trifluoroethyl)-1,3,4,5-tetrahydro-2H-1-benzazepin-2-one (30 mg, 0.068 mmol), pyridin-3-ylboronic acid (12.67 mg, 0.103 mmol), palladium acetate (3.07 mg, 0.014 mmol), potassium phosphate tribasic (29.0 mg, 0.137 mmol), and S-Phos (8.42 mg, 0.021 mmol) were added to a microwave vial. The reactants were suspended in THF (414 μL) and H₂O (41 μL) and the vial sealed. The reaction mixture was irradiated at 120° C. in the microwave for 10 minutes, The completed reaction was filtered and concentrated in vacuo. Analytically pure material was obtained by purification by preparative HPLC Reverse phase (C-18), eluting with acetonitrile/water+0.05% Formic Acid. Lyophilisation afforded 6-fluoro-3-[4-(3-pyridin-3-ylphenyl)-1H-1,2,3-triazol-1-yl]-1-(2,2,2-trifluoroethyl)-1,3,4,5-tetrahydro-2H-1-benzazepin-2-one.

Calcd for $C_{25}H_{19}F_4N_5O$ [M+1]⁺: 482. Found: 482.

Example 121

6-fluoro-3-{4-[3-(pyridin-4-ylamino)phenyl]-1H-1,2,3-triazol-1-yl}-1-(2,2,2-trifluoroethyl)-1,3,4,5-tetrahydro-2H-1-benzazepin-2-one

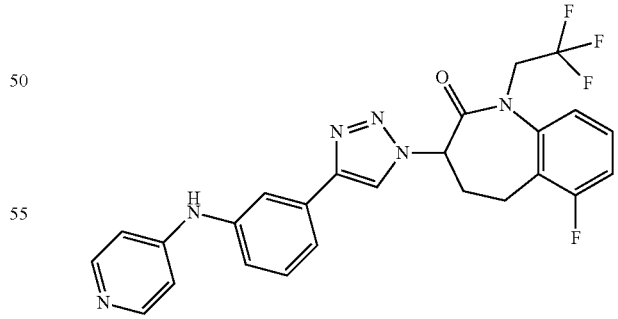

3-[4-(3-Chlorophenyl)-1H-1,2,3-triazol-1-yl]-6-fluoro-1-(2,2,2-trifluoroethyl)-1,3,4,5-tetrahydro-2H-1-benzazepin-2-one (20 mg, 0.046 mmol), pyridin-4-amine 6.39 mg, 0.068 mmol), palladium(II) acetate (2.047 mg, 9.12 μmol), Xantphos (7.91 mg, 0.014 mmol), and cesium carbonate (44.6 mg, 0.137 mmol) were combined and dissolved in dioxane (912 μl). The reaction was irradiated in the microwave at 180° C.

for 15 minutes. The completed reaction was filtered and concentrated in vacuo. Analytically pure material was obtained by purification by preparative HPLC Reverse phase (C-18), eluting with acetonitrile/water+0.05% formic acid. Lyophilisation afforded 6-fluoro-3-{4-[3-(pyridin-4-ylamino)phenyl]-1H-1,2,3-triazol-1-yl}-1-(2,2,2-trifluoroethyl)-1,3,4,5-tetrahydro-2H-1-benzazepin-2-one.

Calc'd for $C_{25}H_{20}F_4N_6O$ [M+1]$^+$: 497. Found: 497.

Example 122

(R) and (S)-6-fluoro-3-(4-[4-(2-methylpyridin-4-yl)phenyl]-1H-1,2,3-triazol-1-yl)trifluoroethyl)-1,3,4,5-tetrahydro-2H-1-benzazepin-2-one

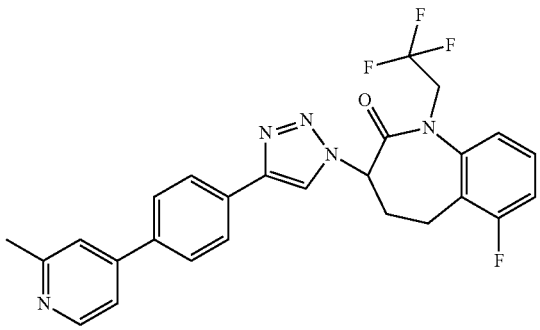

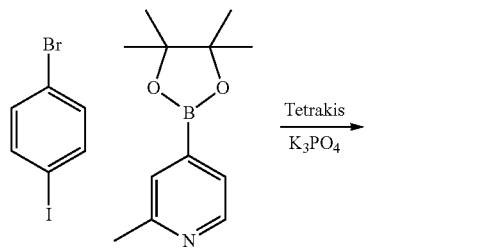

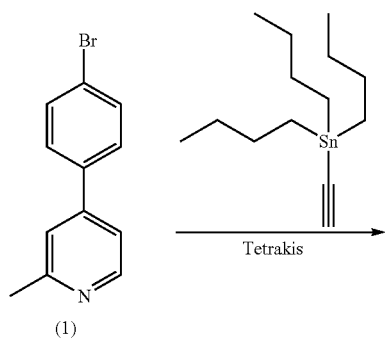

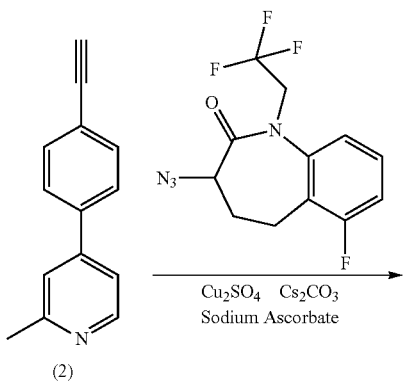

Step 1: 4-(4-bromophenyl)-2-methylpyridine (1)

1-Bromo-4-iodo-benzene (7.07 mmol), 2-methyl-4-boronic pinacole ester pyridine (14.14 mmol), potassium phosphate (28.3 mmol), and Pd(PPh$_3$)$_4$ (0.707 mmol) were added to 20.0 mL of degassed THF. The reaction was then refluxed for 17 hrs. The reaction was diluted with DCM and washed with saturated sodium bicarbonate, brine, dried with sodium sulfate, filtered and concentrated down. The product was loaded in a minimal amount of DCM and purified by normal phase (DCM:MeOH). Pure fractions were pooled and dried down to afford the product as a solid (75% pure, 32.1% yield). LC-ESMS observed [M+H]$^+$ 248.0 (calcd 248.0)

Step 2: 4-(4-ethynylphenyl-2-methylpyridine (2)

Tributyl(ethynyl)tin (1.2 mmol), Pd(PPh$_3$)$_4$ (0.055 mmol), and product 1 (1.091 mmol) were added to THF in a microwave vial. The vial was sealed and irradiated at 120° C. for 15 min. The reaction was diluted with DCM and washed with saturated sodium bicarbonate, brine, dried with sodium sulfate, filtered and concentrated down. The product was loaded in a minimal amount of DCM and purified by normal phase (Hex:EtOAc). Pure fractions were pooled and dried down to afford the product (93% pure, 37.4% yield). LC-ESMS observed [M+H]$^+$194.1 (calcd 194.1)

Step 3: (R) and (S)-6-fluoro-3-{-4-[4-(2-methylpyridin-4-yl)phenyl]-1H-1,2,3-triazol-1-yl}-1-(2,2,2-trifluoroethyl)-1,3,4,5-tetrahydro-2H-1-benzazepin-2-one Alkyne (0.802 mmol), azide (0.882 mmol), and sodium ascorbate (0.802 mmol) were added to 4.0 mL of 1:1 DMF:EtOH. Copper(II) sulfate pentahydrate (0.401 mmol) was dissolved in 0.5 mL of water. The copper solution was then added to the reaction flask and the reaction stirred at room temperature for 16 hrs. The reaction was diluted with DCM and washed with 2N NaOH, dried with sodium sulfate, filtered and concentrated down. The product was loaded in a minimal amount of DCM and purified by normal phase (DCM:MeOH). Pure fractions were pooled and dried down to afford the racemic product as a solid (>98% pure, 60.4% yield).

Resolution (of the free base): 45%/55% Isopropanol/CO2 (no other modifiers) Column: Chiral Technology AS-H 2.1× 25 cm, 5 uM; 220, 254 nm detection; enantiomer 1 (0.220 mmol), enantiomer 2 (0.220 mmol).

$^1$H-NMR (600 MHz, CDCl$_3$) 8-2.61 (3H, s), 2.72-2.64 (2H, m), 2.83-2.72 (1H, m), 3.37-3.29 (1H, m), 4.03 (1H, dq, J=16.2, 8.2), 5.09 (1H, dq, J=17.4, 8.7), 5.58 (1H, dd, J=11.0, 8.8), 7.12, (2H, dd, J=14.8, 8.2), 7.33 (1H, dd, J=5.2, 1.3), 7.44-7.36 (2H, m), 7.69 (2H, d, J=8.3), 7.94 (2H, d, J=8.4), 8.28 (1H, s), 8.53 (1H, d, J=5.2)

LC-ESMS observed [M+H]$^+$496.1 (calcd 496.2).

Example 123

(R) and (S)-6-fluoro-3-[4-(4-pyridazin-4-ylphenyl)-1H-1,2,3-triazol-1-yl]-1-(2,2,2-trifluoroethyl)-1,3,4,5-tetrahydro-2H-1-benzazepin-2-one

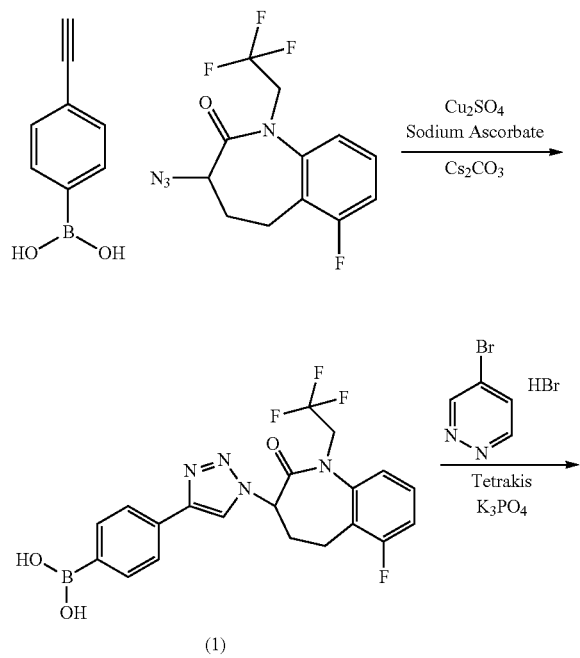

Step 1: (R) and (S)-(4-{1-[6-fluoro-2-oxo-1-(2,2,2-trifluoroethyl)-2,3,4,5-tetrahydro-1H-1-benzazepin-3-yl}-1H-1,2,3-triazol-4-yl]phenyl)boronic acid (1)

Alkyne (3.43 mmol), azide (3.77 mmol), and sodium ascorbate (3.43 mmol) were added to 10.0 mL of 1:1 DMF:EtOH. Copper(II) sulfate pentahydrate (1.71 mmol) was dissolved in 1.5 mL of water. The copper solution was then added to the reaction flask and the reaction stirred at room temperature for 16 hrs. The reaction was diluted with DCM and washed with 2N NaOH, dried with sodium sulfate, filtered and concentrated down. The product was loaded in a minimal amount of DCM and purified by normal phase (DCM:MeOH). Pure fractions were pooled and dried down to afford the racemic product as a solid (>95% pure, 74.9% yield). LC-ESMS observed [M+H]$^+$449.0 (calcd 449.1)

Step 2: (R) and (S)-6-fluoro-3-[4-(4-pyridazin-4-ylphenyl)-1H-1,2,3-triazol-1-yl]-1-(2,2,2-trifluoroethyl)-1,3,4,5-tetrahydro-2H-1-benzazepin-2-one Boronic acid (1.339 mmol), 4-bromopyridazine hydrobromide (2.68 mmol), potassium carbonate (5.36 mmol), and tetrakis (0.134 mmol) were added to degassed THF in a pressure vessel. It was then sealed and heated to 80° C. for 16 hrs. The reaction was diluted with DCM and washed with saturated sodium bicarbonate, brine, dried with sodium sulfate, filtered and concentrated down. The product was loaded in a minimal amount of DCM and purified by normal phase (DCM:MeOH). Pure fractions were pooled and dried down to afford the racemic product as a solid (>99% pure, 71.1% yield).

Resolution (of the free base): 40%/60% Methanol/CO2 (no other modifiers), Column: Chiral Technology OJ-H 2.1×25 cm, 5 uM; 220 nm detection; enantiomer 1 (0.365 mmol), enantiomer 2 (0.346 mmol).

$^1$H-NMR (600 MHz, CDCl$_3$) δ=2.69 (2H, ddd, J=12.8, 6.1, 3.6), 2.82-2.73 (1H, m), 3.38-3.29 (1H, m), 4.03 (1H, dq, J=16.2, 8.2), 5.09 (1H, dq, J=17.4, 8.7), 5.65-5.53 (1H, m), 7.17-7.07 (2H, m), 7.44-7.34 (1H, m), 7.67 (1H, dd, J=5.4, 2.5), 7.74 (2I-1, d, J=8.4), 8.01 (2I-1, d J=8.3), 8.32 (1H, s), 9.22 (1H, d, J=4.7), 9.49 (1H, d, =1.2).

LC-ESMS observed [M+H]$^+$483.0 (calcd 483.2).

Example 124

6-fluoro-1-(2,2,2-trifluoroethyl)-3-(4-{4-[2-(trifluoromethyl)pyridin-4-yl]phenyl}-1H-1,2,3-triazol-1-yl)-1,3,4,5-tetrahydro-2H-1-benzazepin-2-one

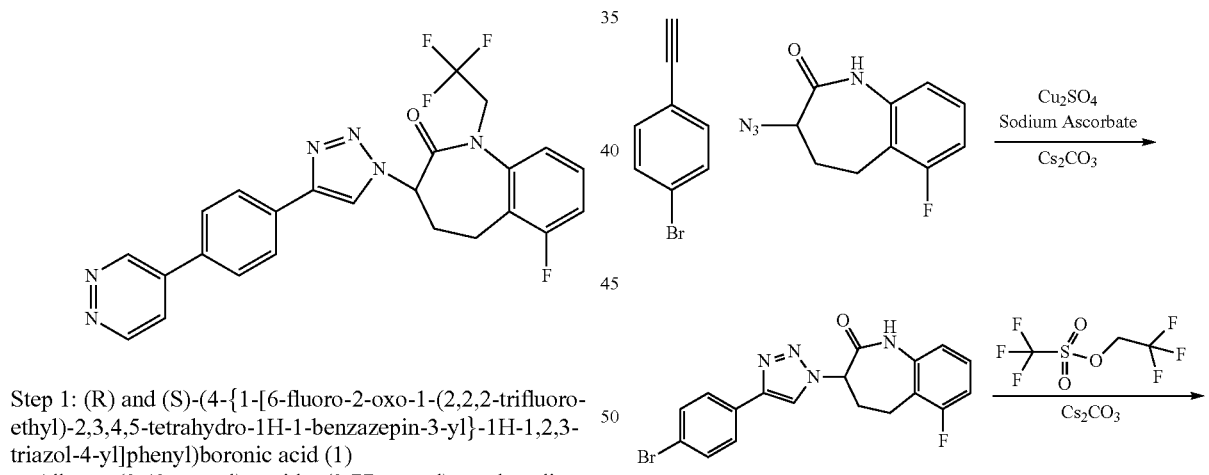

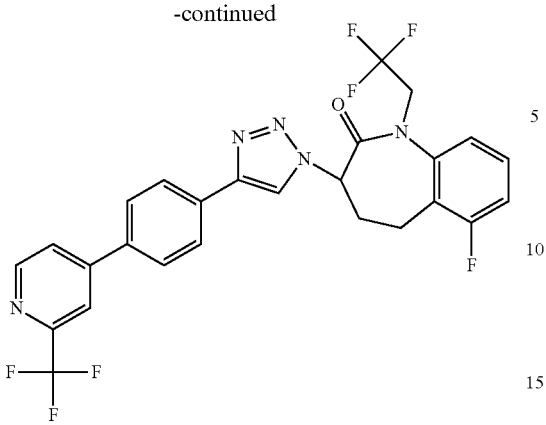

Step 1: (R) and (S)-3-[4-(4-bromophenyl)-1H-1,2,3-triazol-1-yl]-6-fluoro-1,3,4,5-tetrahydro-2H-1-benzazepin-2-one (1)

Alkyne (5.52 mmol), azide (6.08 mmol), and sodium ascorbate (5.52 mmol) were added to 10.0 mL of 1:1 DMF:EtOH. Copper(II) sulfate pentahydrate (2.76 mmol) was dissolved in 1.5 mL of water. The copper solution was then added to the reaction flask and the reaction stirred at room temperature for 16 hrs. The reaction was diluted with DCM and washed with 2N NaOH, dried with sodium sulfate, filtered and concentrated down. The product was loaded in a minimal amount of DCM and purified by normal phase (DCM:MeOH). Pure fractions were pooled and dried down to afford the racemic product as a solid (95% pure, 90.0% yield). LC-ESMS observed [M+H]$^+$ 402.9 (calcd 401.0)

Step 2: (R) and (S)-3-[4-(4-bromophenyl)-1H-1,2,3-triazol-1-yl]-6-fluoro-1-(2,2,2-trifluoroethyl)-1,3,4,5-tetrahydro-2H-1-benzazepin-2-one (2)

Bromide (5.23 mmol), 2,2,2-trifluoroethyl trifluoromethanesulfonate (5.76 mmol), and cesium carbonate (7.85 mmol) were added to THF and heated at 65° C. for 1 hr. Upon cooling, the reaction was diluted with DCM and washed with 2N NaOH, dried with sodium sulfate, filtered and concentrated down. The product was loaded in a minimal amount of DCM and purified by normal phase (DCM:MeOH). Pure fractions were pooled and dried down to afford the racemic product as a solid (99% pure, 71.2% yield). LC-ESMS observed [M+H]$^+$ 484.9 (calcd 483.1)

Step 3: (R) and (S)-6-fluoro-1-(2,2,2-trifluoroethyl)-3-(4-{4-[2-(trifluoromethyl)pyridin-4-yl]phenyl}-1H-1,2,3-triazol-1-yl)-1,3,4,5-tetrahydro-2H-1-benzazepin-2-one Bromide (0.414 mmol), boronic acid (0.828 mmol), potassium carbonate (1.655 mmol), and tetrakis (0.041 mmol) were added to 1.5 mL of degassed THF in a pressure vessel. It was then sealed and heated to 80° C. for 16 hrs. The reaction was diluted with DCM and washed with saturated sodium bicarbonate, brine, dried with sodium sulfate, filtered and concentrated down. The product was loaded in a minimal amount of DCM and purified by normal phase (DCM:MeOH). Pure fractions were pooled and dried down to afford the racemic product as a solid (>99% pure, 71.1% yield).

$^1$H-NMR (600 MHz, CDCl$_3$) δ=2.69 (2H, ddd, J=12.9, 6.2, 3.6), 2.78 (1H, dd, J=22.0, 13.4), 3.39-3.28 (1H, m), 4.07-3.97 (1H, m), 5.09 (1H, dq, J=17.4, 8.6), 5.64-5.53 (1H, m), 7.13 (2H, dd, J=14.6, 8.2), 7.40 (1H, dd, J=14.3, 8.3), 7.72 (3H, m), 7.92 (1H, s), 8.00 (2H, d, J=8.3), 8.31 (1H, s), 8.76 (11-1, d, J=5.1).

LC-ESMS observed [M+H]$^+$ 550.4 (calcd 550.2).

The invention claimed is:

1. A compound of formula I:

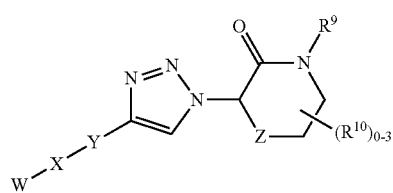

or a pharmaceutically acceptable salt or hydrate thereof; wherein:

W represents phenyl or 5- or 6-membered heteroaryl comprising up to 3 heteroatoms selected from N, O and S, wherein the phenyl or heteroaryl is optionally fused to a further 5- or 6-membered carbocyclic, or 5- or 6-membered heterocyclic ring, W optionally bearing up to 3 $R^1$ substituents; or when X is a bond W may represent CN and when X is CO W may represent a piperazin-1-yl or piperidin-1-yl ring;

each $R^1$ independently represents halogen, OH, amino, $CF_3$, $C_{1-4}$alkylamino, di($C_{1-4}$alkyl)amino, $C_{2-6}$acylamino, N—$C_{1-4}$alkoxycarbamoyl, $C_{1-6}$alkoxy, $C_{1-6}$alkylcarbonyl, or $C_{1-6}$alkyl which is optionally substituted with OH or $C_{1-4}$alkoxy;

X represents a bond, $(CH_2)_nO$, $(CH_2)_nNH$, CO or $(CH_2)_n$NHCO where each n is 0 or 1;

Y represents a phenyl or 5- or 6-membered heteroaryl ring which optionally bears up to 3 $R^2$ substituents; or when X is a bond and W is not CN, Y may represent C≡C or a $C_{3-6}$cycloalkyl ring; or when X is a bond or CO, Y may represent piperidin-4-yl;

or the moiety W-X-Y may represent a fused-ring system consisting of 2 or 3 fused rings selected from the group consisting of;

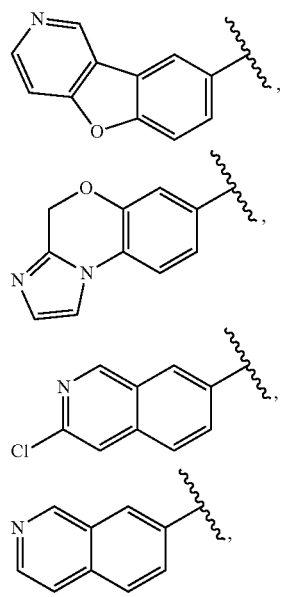

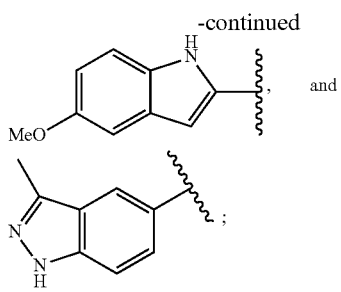

and

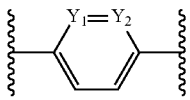

with the proviso that if X is a bond and W represents an imidazole, triazole or pyrazole ring which is linked to Y through N, then Y does not represent

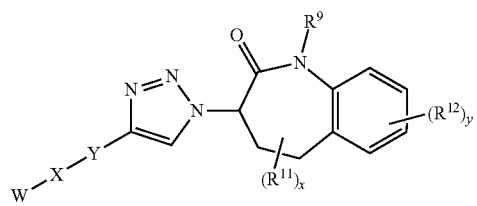

where Y1 and Y2 each independently represents N or $CR^2$;

each $R^2$ independently represents halogen, CN, OH, $C_{1-6}$alkyl, or $C_{1-6}$alkoxy, said alkyl and alkoxy optionally having up to 3 fluorine substituents or a cyclopropyl substituent;

Z represents $CH_2$, $CH_2$—$CH_2$, O, S, NH, $CH_2$—O, $CH_2$—S or $CH_2$—NH;

$R^9$ represent H, $C_{1-6}$alkyl, $C_{2-6}$alkenyl, polyfluoro$C_{1-4}$alkyl, $C_{3-6}$cycloalkyl, $C_{3-6}$cycloalkyl$C_{1-4}$alkyl, $C_{1-4}$alkoxy$C_{1-4}$alkyl, amino$C_{1-4}$alkyl, $C_{1-4}$alkylcarbonyl, polyfluoro$C_{1-4}$alkylcarbonyl, $C_{1-4}$alkylsulfonyl, phenyl, phenylsulfonyl, benzoyl, benzyl, naphthylmethyl or pyridylmethyl, where said phenyl and the aromatic portions of said phenylsulfonyl, benzoyl, benzyl, naphthylmethyl and pyridylmethyl optionally bear up to 3 substituents selected from halogen, $C_{1-4}$alkyl, $C_{1-4}$alkoxy and $CF_3$;

each $R^{10}$ independently represents halogen, OH, $C_{1-4}$alkyl, $C_{2-4}$alkenyl, polyfluoro$C_{1-4}$alkyl, $C_{3-6}$cycloalkyl, $C_{3-6}$cycloalkyl$C_{1-4}$alkyl, $C_{1-4}$alkoxy, $C_{1-4}$alkoxy$C_{1-4}$alkyl, polyfluoro$C_{1-4}$alkoxy, $C_{1-4}$alkylcarbonyl, polyfluoro$C_{1-4}$alkylcarbonyl, $C_{1-4}$alkoxycarbonyl, $C_{1-4}$alkylthio, $C_{1-4}$alkylsulfonyl, $SO_2NR_2$, $CONR_2$ or $NR_2$ where each R is independently H or $C_{1-4}$alkyl or the two R groups together with the nitrogen to which they are attached complete a ring selected from azetidine, pyrrolidine, piperidine, piperazine and morpholine; or phenyl or benzyl either of which optionally is substituted with halogen, $C_{1-4}$alkyl, $C_{1-4}$alkoxy or $CF_3$;

or two $R^{10}$ groups attached to adjacent ring positions optionally complete a fused benzene, naphthalene, cyclopentane, cyclohexane, pyridine, thiophene or furan ring which optionally bears up to 2 substituents independently selected from halogen, $NO_2$, CN, OH, phenyl, $C_{1-4}$alkyl, $C_{2-4}$alkenyl, polyfluoro$C_{1-4}$alkyl, $C_{3-4}$cycloalkyl, $C_{3-6}$cycloalkyl$C_{1-4}$alkyl, $C_{1-4}$alkoxy, $C_{1-4}$alkoxy$C_{1-4}$alkyl, polyfluoro$C_{1-4}$alkoxy, $C_{1-4}$alkylcarbonyl, polyfluoro$C_{1-4}$alkylcarbonyl, $C_{1-4}$alkoxycarbonyl, $C_{1-4}$alkylthio, $C_{1-4}$alkylsulfonyl, $SO_2NR_2$, $CONR_2$ or $NR_2$ where each R is independently H or $C_{1-4}$alkyl;

or two $R^{10}$ groups attached to non-adjacent ring positions optionally complete a $CH_2$ or $CH_2CH_2$ bridge.

2. A compound according to claim 1 of formula II:

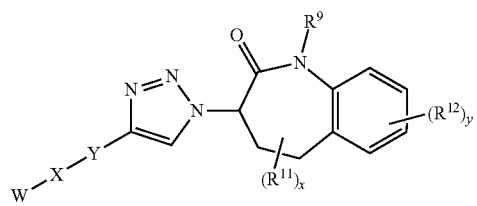

or a pharmaceutically acceptable salt or hydrate thereof; wherein x is 0, 1 or 2;

y is 0, 1 or 2;

$R^{11}$ represents methyl or phenyl with the proviso that x is not 2 when $R^{11}$ is phenyl; and each $R^{12}$ is independently selected from phenyl, $NO_2$ halogen, $C_{1-4}$alkyl, polyfluoro$C_{1-4}$alkyl, $C_{1-4}$alkoxy and polyfluoro$C_{1-4}$alkoxy with the provision that not more than one $R^{12}$ represents phenyl or $NO_2$.

3. A compound according to claim 2 or a pharmaceutically acceptable salt or hydrate thereof, wherein $R^9$ represents $CH_2CF_3$, x is 0, y is 0 or 1 and $R^{12}$ represents F.

4. A compound according to claim 1 or a pharmaceutically acceptable salt or hydrate thereof, wherein Y is ring selected from phenyl, pyridine, pyrimidine, thiophene, furan, thiazole and imidazole and optionally bears up to 2 $R^2$ substituents.

5. A compound according to claim 4 or a pharmaceutically acceptable salt or hydrate thereof, wherein each $R^2$ independently represents H, F or $C_{1-4}$alkoxy.

6. A compound according to claim 1 or a pharmaceutically acceptable salt or hydrate thereof, wherein W represents phenyl, naphthalene, tetrahydronaphthalene, quinoline, methylenedioxyphenyl, pyridine, pyridazine, pyrimidine, or a 5-membered heteroaryl selected from pyrrole, furan, thiophene, pyrazole, imidazole, oxazole, isoxazole, thiazole, isothiazole, triazole, oxadiazole or thiadiazole, and a benzo- or pyrido-fused analogue of said 5-membered heteroaryl, any of which optionally bears up to two $R^1$ substituents.

7. A compound according to claim 6 or a pharmaceutically acceptable salt or hydrate thereof, wherein W represents 4-pyridyl which optionally bears up to 2 substituents selected from F, Cl, $CF_3$, $C_{1-4}$alkyl, and $C_{1-4}$alkoxy, X is a bond, and Y represents 1,4-phenylene which optionally bears up to 2 substituents selected from F, Cl, $CF_3$, $C_{1-4}$alkyl, and $C_{1-4}$alkoxy.

8. A pharmaceutical composition comprising a compound according to claim 1 or a pharmaceutically acceptable salt or hydrate thereof, and a pharmaceutically acceptable carrier.

* * * * *